US009925262B2

(12) United States Patent
Zhou et al.

(10) Patent No.: US 9,925,262 B2
(45) Date of Patent: *Mar. 27, 2018

(54) KITS COMPRISING FORMULATIONS OF ANTI-C5 ANTIBODIES

(71) Applicant: Alexion Pharmaceuticals, Inc., New Haven, CT (US)

(72) Inventors: Xiao-Hong Zhou, Madison, CT (US); Yi Wang, Woodbridge, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/384,788

(22) Filed: Dec. 20, 2016

(65) Prior Publication Data

US 2017/0151328 A1    Jun. 1, 2017

Related U.S. Application Data

(60) Continuation of application No. 15/176,774, filed on Jun. 8, 2016, now Pat. No. 9,556,263, which is a continuation of application No. 15/096,747, filed on Apr. 12, 2016, now Pat. No. 9,409,980, which is a division of application No. 13/413,268, filed on Mar. 6, 2012, now Pat. No. 9,415,102.

(60) Provisional application No. 61/450,334, filed on Mar. 8, 2011.

(51) Int. Cl.
| | |
|---|---|
| *A61K 39/395* | (2006.01) |
| *C07K 16/18* | (2006.01) |
| *A61K 47/18* | (2017.01) |
| *A61K 47/22* | (2006.01) |
| *A61K 47/26* | (2006.01) |
| *A61K 9/08* | (2006.01) |
| *A61K 39/00* | (2006.01) |

(52) U.S. Cl.
CPC .......... *A61K 39/39591* (2013.01); *A61K 9/08* (2013.01); *A61K 39/3955* (2013.01); *A61K 47/183* (2013.01); *A61K 47/22* (2013.01); *A61K 47/26* (2013.01); *C07K 16/18* (2013.01); *A61K 2039/505* (2013.01); *C07K 2317/24* (2013.01); *C07K 2317/515* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,228,795 A | 10/1980 | Babington | |
| 5,614,370 A | 3/1997 | Konteatis et al. | |
| 5,728,844 A | 3/1998 | Muller et al. | |
| 5,871,734 A | 2/1999 | Lobb et al. | |
| 6,316,502 B1 | 11/2001 | Lai et al. | |
| 6,355,245 B1 | 3/2002 | Evans et al. | |
| 6,524,836 B2 | 2/2003 | Sheppard | |
| 6,740,655 B2 | 5/2004 | Magee et al. | |
| 6,905,688 B2 | 6/2005 | Rosen et al. | |
| 6,956,107 B2 | 10/2005 | Fung et al. | |
| 6,998,468 B2 | 2/2006 | Fung et al. | |
| 7,071,299 B2 | 7/2006 | West et al. | |
| 7,833,525 B2 | 11/2010 | Shenoy et al. | |
| 9,352,035 B2 | 5/2016 | Zhou et al. | |
| 9,409,980 B1 | 8/2016 | Zhou et al. | |
| 9,415,102 B2 | 8/2016 | Zhou et al. | |
| 9,447,176 B2 | 9/2016 | Rother et al. | |
| 9,556,263 B2 | 1/2017 | Zhou et al. | |
| 2001/0036650 A1 | 11/2001 | Li et al. | |
| 2002/0172677 A1 | 11/2002 | Lahn et al. | |
| 2002/0182260 A1 | 12/2002 | Mak et al. | |
| 2003/0124139 A1 | 7/2003 | Esikova et al. | |
| 2003/0171259 A1 | 9/2003 | Modi | |
| 2004/0014782 A1 | 1/2004 | Krause | |
| 2004/0115194 A1 | 6/2004 | Wang | |
| 2004/0219147 A1 | 11/2004 | Bell | |
| 2005/0053598 A1 | 3/2005 | Burke et al. | |
| 2005/0191298 A1 | 9/2005 | Bell et al. | |
| 2005/0271660 A1 | 12/2005 | Wang | |
| 2005/0282734 A1 | 12/2005 | Kadima et al. | |
| 2007/0173444 A1 | 7/2007 | Balu et al. | |
| 2008/0071063 A1 | 3/2008 | Allan et al. | |
| 2008/0193466 A1 | 8/2008 | Banerjee et al. | |

(Continued)

FOREIGN PATENT DOCUMENTS

| | | |
|---|---|---|
| CA | 2189015 A1 | 11/1995 |
| CA | 2198706 A1 | 3/1996 |

(Continued)

OTHER PUBLICATIONS

Varsano et al., "Generation of Complement C3 and Expression of Cell Membrane Complement Inhibitory Proteins by Human Bronchial Epithelium Cell Line,"Thorax 55:364-369 (2000).

Wang et al., "Amelioration of Luplike Autoimmune Disease in NZBIWF, Mice after Treatment with a Blocking Monoclonal Antibody Specific for Complement Component C5," Proc. Natl. Acad. Sci. USA 93:8563-8568 (1996).

Wang et al., "Anti-C5 Monoclonal Antibody Therapy Prevents Collagen-induced Arthritis and Ameliorates Established Disease," Proc. Natl. Acad. Sci. USA 92:8955-8959 (1995).

(Continued)

*Primary Examiner* — Phillip Gambel
(74) *Attorney, Agent, or Firm* — J. Darrell Fontenot, Esq.; Jane E. Remillard, Esq.; Jill Gorny Sloper, Esq.

(57) ABSTRACT

The present disclosure relates to, inter alia, stable aqueous solutions comprising a high concentration of an antibody that binds to human complement component C5 and methods for preparing the solutions. The disclosure also provides methods for treating or preventing complement-associated disorders (for example, age-related macular degeneration or rheumatoid arthritis) using the solutions. Also featured are therapeutic kits containing one or more of the solutions and a means for administering the solutions to a patient in need such a treatment.

13 Claims, 1 Drawing Sheet

(56) References Cited

U.S. PATENT DOCUMENTS

| | | |
|---|---|---|
| 2009/0060906 A1 | 3/2009 | Barry et al. |
| 2009/0175857 A1 | 7/2009 | Salfeld et al. |
| 2010/0027882 A1 | 2/2010 | Matsuoka |
| 2010/0104563 A1 | 4/2010 | Ghayer et al. |
| 2010/0111953 A1 | 5/2010 | Ruben et al. |
| 2010/0278822 A1 | 11/2010 | Fraunhofer et al. |
| 2012/0225056 A1 | 9/2012 | Rother et al. |
| 2012/0230982 A1 | 9/2012 | Zhou et al. |
| 2014/0056888 A1 | 2/2014 | Zhou et al. |
| 2016/0215044 A1 | 7/2016 | Zhou et al. |
| 2016/0272700 A1 | 9/2016 | Zhou et al. |
| 2016/0319004 A1 | 11/2016 | Rother et al. |
| 2016/0355579 A1 | 12/2016 | Rother et al. |
| 2016/0355580 A1 | 12/2016 | Rother et al. |
| 2017/0015740 A1 | 1/2017 | Rother et al. |

FOREIGN PATENT DOCUMENTS

| | | |
|---|---|---|
| EP | 0649468 A1 | 4/1995 |
| WO | 95/29697 A1 | 11/1995 |
| WO | 98/11066 A1 | 3/1998 |
| WO | 98/18827 A1 | 5/1998 |
| WO | 03/084524 A1 | 10/2003 |
| WO | 2004/022096 A1 | 3/2004 |
| WO | 2005/011614 A2 | 2/2005 |
| WO | 2006/122257 A2 | 11/2006 |

OTHER PUBLICATIONS

Whiss, PA, "Pexelizumab Alexion," Current Opinion Investig. Drugs, vol. 3(6):870-877 (2002). (abstract).

Wills-Karp et al., "Interleukin-13: Central Mediator of Allergic Asthma," Science 282:2258-2261 (1998).

Abe et al., "Contribution of Anaphylatoxin C5a to Late Airway Responses after Repeated Exposure of Antigen to Allergic Rats," The Journal of Immunology 167(8):4651-4660 (2001).

Abrahamsen et al., "Differential Mediator Release from Basophils of Allergic and Non-allergic Asthmatic Patients after Stimulation with Anti-IgE and C5a," Clinical and Experimental Allergy 31 :368-378 (2001).

Akatsu et al., "Distribution of Rat C5a Anaphylatoxin Receptor," Microbiol. Immunol. 46(12):863-874 (2002).

American Heritage College Dictionary, 3rd Edition. Houghton Mifflin Company, Boston, p. 1085 (1997).

Bjornson et al., "Complement is Activated in the Upper Respiratory Tract During Influenza Virus Infection," Am. Rev. Respir. Dis. 143:1062-1066 (1991).

Blease et al., "Chemokines and Their Role in Airway Hyper-reactivity," Respir. Res. 1 :54-61 (2000).

Boulet et al., "Airway Hyperresponsiveness, Inflammation, and Subepithelial Collagen Deposition in Recently Diagnosed vs. Long-standing Mild Asthma," American Journal of Respiratory and Critical Care Medicine 162:1308-1313 (2000).

Chakir et al., "Airway Remodeling-associated Mediators in Moderate to Severe Asthma: Effect ** of Steroids on TGF-f3, IL-11, IL-17, and Type I and Type III Collagen Expression," J. Allergy Clin. Immunol. 111 :1293-1298 (2003).

Chenoweth et al., "Demonstration of Specific C5a Receptor on Intact Human Polymorphonuclear Leukocytes," Proc. Natl. Acad. Sci. USA 75(8):3943-3947 (1978).

Chung, "Cytokines in Chronic Obstructive Pulmonary Disease," Eur. Respir. J. 18(34):50s-59s (2001).

Cieslewicz et al., "The Late, but not Early, Asthmatic Response is Dependent on IL-5 and Correlates with Eosinophil Infiltration," J. Clin. Invest. 104:301-308 (1999).

Collard et al., "Complement Activation Following Oxidative Stress," Molecular Immunology 36:941-948 (1999).

Czermak et al., "Complement, Cytokines, and Adhesion Molecule Expression in Inflammatory Reactions," Proceedings of the Association of American Physicians 110(5):306-312 (1998).

Desai et al., "Demonstration of C5 Cleaving Activity in Bronchoalveolar Fluids and Cells: A Mechanism of Acute and Chronic Alveolitis," Journal of Experimental Pathology 1(3):201-216 (1984).

Drouin et ai, "Expression of the Complement Anaphylatoxin C3a and C5a Receptors on Bronchial Epithelial and Smooth Muscle Cells in Models of Sepsis and Asthma," The Journal of Immunology 166:2025-2032 (2001).

Fitch et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass," Circulation 100:2499-2506(1999).

Frank, "Complement: A Brief Review," J. Allergy Clin. Immunol. 84(4,1 ):411-420 (1989).

Gerard et al., "Complement in Allergy and Asthma," Current Opinion in Immunology 14:705-708 (2002).

Glovsky et al., "Is Complement Activation a Factor in Bronchial Asthma?," Int. Arch. Allergy Immunol. 118:330-332 (1999).

Gonczi et al., "The Severity of Clinical Symptoms in Ragweed-allergic Patients is Related to the Extent of Ragweed-Induced Complement Activation in their Sera," Allergy 51 :1110-1114 (1997).

Hawlisch et al., "Teh Anaphylatoxins Bridge Innate and Adaptive Immune Responses in Allergic Asthma," Molecular Immunology 41 :123-131 (2004).

Hogaboam et al., "Mannose-binding Lectin Deficiency Alters the Development of Fungal: Asthma: Effects on Airway Response, Inflammation, and Cytokine Profile," Journal of Leukocyte Biology 75:805-814 (2004).

Holgate et al., "The Bronchial Epithelium as a Key Regulator of Airway Inflammation and Remodelling in Asthma," Clinical and Experimental Allergy 29:90-95 (1999).

Hopken et al., "Teh C5a Chemoattractant Receptor Mediates Mucosal Defence to Infection," Nature 383:86-89 (1996).

Humbles et al., "A role for the C3a anaphylatoxin receptor in the effector phase of asthma," Letters to Nature, vol. 406; pp. 998-1001 (2000).

Irvin et al., "Airways Hyperreactivity and Inflammation Produced by Aerosolization of Human C5A des arg 1-3," Am. Rev. Respir. Dis. 134:777-783 (1986).

Jagels et al., "C3a and C5a Enhance Granulocyte Adhesion to Endothelial and Epithelial Cell Monolayers: Epithelial and Endothelial Priming is Required for C3a-induced Eosinophil Adhesion," Immunopharmacology 46:209-222 (2000).

Kaplan, Mariana, "Eculizumab," Current Opinion in Investigational Drugs, vol. 3(7): 1017-1023 (2002).

Karp et al., "Identification of Complement Factor 5 as a Susceptibility Locus for Experimental Allergic Asthma," Nature Immunology 1( 3):221-226 (2000).

Kodani et al., "Intratracheal Administration of Anaphylatoxin C5a Potentiates Antigen-induced Pulmonary Reactions Through the Prolonged Production of Cysteinyl-leukotrienes," Immunopharmacology 49:263-274 (2000).

Krug et al., "Complement Factors C3a and C5a are Increased in Bronchoalveolar Lavage Fluid after Segmental Allergen Provocation in Subjects with Asthma," Am. J. Respir. Crit. Care Med. 164:1841-1843 (2001).

Larsen et al., "A Differential Effect of C5a and C5a des Arg inthe Induction of Pulmonary Inflammation," Am. J. Pathol. 100:179-192 (1980).

Lukacs et al., "Complement-dependent Immune Complex-induced Brochial Inflammation and Hyperactivity," Am. J. Physiol. Lunch Cell Mol. Physiol. 280:L512-L518 (2001).

Maruo et al., "Generation of Anaphylatoxins Through Proteolytic Processing of C3 and C5 by House dust Mite Protease," J. Allergy Clin. Immunol. 100:253-260 (1997).

Matis and Rollins, Complement-specific antiobodies: Designing novel anti-inflammatories, Nature Medicine, vol. 1 No. 8, (1995).

Mattos et al., "Matrix Metalloproteinase-9 Expression in Asthma," Chest 122:1543-1552 (2002).

Moongkarndi et al., "Immunological and functional properties of two monoclonal antibodies against human C5," Immunobiol. vol. 165, p. 323 (1983).

(56) References Cited

OTHER PUBLICATIONS

Moongkarndi et al., "Monoclonal antibodies against the fifth component of human complement," Immunobiol, vol. 162; p. 397(1982).
Mueller et al., "Humanized Porcine VCAM-Specific Monoclonal Antibodies With Chimeric** IgG2/G4 Constant Regions Block Human Leukocyte Binding to Porcine Endothelial Cells," Molecular Immunology, vol. 34(6), pp. 441-452 (1997).
Nagata et al., "Activation of Human Serum Complement with Allergens," J. Allergy Clin. Immunol.80:24-32 (1987).
Nagy et al., "The Development of Asthma in Children Infected with Chlamydia pneumoniae is Dependent on the Modifying Effect of Mannose-binding Lectin," J. Allergy Clin. Immunol. 112(4):729-734 (2003).
Neurogen Reports Phase Iia Clinical Trial Results for Oral Asthma Drug, Press Release dated (2004).
O'Byrne et al., "Reassessing the Th2 Cytokine Basis of Asthma," Trends in Pharmacological Sciences 25(5):244-248 (2004).
Peng et al., "Role of C5 in the Development of Airway Inflammation, Airway Hyperresponsiveness, and Ongoing Airway Response," The journal of Clinical Investigation 115(6):1590-1600(2005).
Peng, et al., "Contribution of complement component C5 in the development of airway inflammation, maintaining airway hyperresponsivenesss and sustaining an ongoing asthmatic attack," Mol. Immunol. 41(2-3):292 (2004).
Peng, et al., Blocking Intrapulmonary Activation of Complement Cascade on the Development of Airway Hyperresponsiveness: Utility in sight? J. Allergy & Clin. Immunol. 117(3):720 (2006).
Robbins et al., "Complement Activiation by Cigarette Smoke," L254-L259 (1990).
Taube et al., "Inhibition of Complement Activation Decreases Airway Inflammation and Hyperresponsiveness," Am. J. Respir. Crit. Car Med. 168:1333-1341 (2003).
Teran et al., "Identification of Neutrophil Chemotactic Factors in Bronchoalveolar Lavage Fluid of Asthmatic Patients," Clinical and Experimental Allergy 27:396-405 (1997).
Thomas et al., "Inhibition of Complement Activity by Humanized Anti-O5 Antibody and Single-Chain Fv.," Molecular Immunology, vol. 33(17/18):1389-1401 (1996).

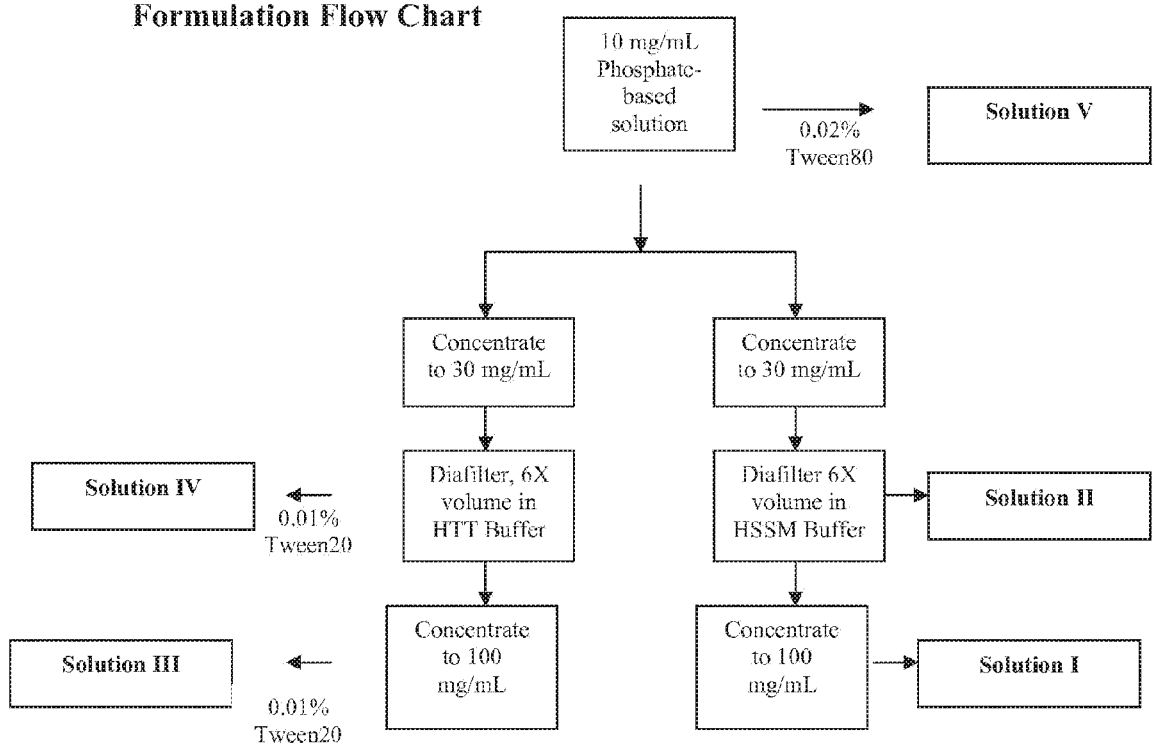

SEQUENCE LISTING

<160> NUMBER OF SEQ ID NOS: 13

<210> SEQ ID NO 1
<211> LENGTH: 1676

<212> TYPE: PRT
<213> ORGANISM: Homo sapiens

<400> SEQUENCE: 1

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
            85                  90                  95

Asn Pro Val Ser Tyr Val Tyr Leu Glu Val Val Ser Lys His Phe Ser
        100                 105                 110

Lys Ser Lys Arg Met Pro Ile Thr Tyr Asp Asn Gly Phe Leu Phe Ile
    115                 120                 125

His Thr Asp Lys Pro Val Tyr Thr Pro Asp Gln Ser Val Lys Val Arg
130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
            165                 170                 175

Ile Asp His Ile Gly Ile Ile Ser Phe Pro Asp Phe Lys Ile Pro Ser
        180                 185                 190

Asn Pro Arg Tyr Gly Met Trp Thr Ile Lys Ala Lys Tyr Lys Glu Asp
    195                 200                 205

Phe Ser Thr Thr Gly Thr Ala Tyr Phe Glu Val Lys Glu Tyr Val Leu
210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
            245                 250                 255

Asn Lys Val Val Thr Glu Ala Asp Val Tyr Ile Thr Phe Gly Ile Arg
        260                 265                 270

Glu Asp Leu Lys Asp Asp Gln Lys Glu Met Met Gln Thr Ala Met Gln
    275                 280                 285

Asn Thr Met Leu Ile Asn Gly Ile Ala Gln Val Thr Phe Asp Ser Glu
290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
            325                 330                 335

Ser Glu Glu Ala Glu Ile Pro Gly Ile Lys Tyr Val Leu Ser Pro Tyr
        340                 345                 350

Lys Leu Asn Leu Val Ala Thr Pro Leu Phe Leu Lys Pro Gly Ile Pro
    355                 360                 365

Tyr Pro Ile Lys Val Gln Val Lys Asp Ser Leu Asp Gln Leu Val Gly
370                 375                 380

Gly Val Pro Val Ile Leu Asn Ala Gln Thr Ile Asp Val Asn Gln Glu
385                 390                 395                 400
```

```
Thr Ser Asp Leu Asp Pro Ser Lys Ser Val Thr Arg Val Asp Asp Gly
            405                 410                 415
Val Ala Ser Phe Val Leu Asn Leu Pro Ser Gly Val Thr Val Leu Glu
        420                 425                 430
Phe Asn Val Lys Thr Asp Ala Pro Asp Leu Pro Glu Glu Asn Gln Ala
            435                 440                 445
Arg Glu Gly Tyr Arg Ala Ile Ala Tyr Ser Ser Leu Ser Gln Ser Tyr
        450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
            485                 490                 495
Thr His Tyr Asn Tyr Leu Ile Leu Ser Lys Gly Lys Ile Ile His Phe
        500                 505                 510
Gly Thr Arg Glu Lys Phe Ser Asp Ala Ser Tyr Gln Ser Ile Asn Ile
        515                 520                 525
Pro Val Thr Gln Asn Met Val Pro Ser Ser Arg Leu Leu Val Tyr Tyr
        530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
            580                 585                 590
Ala Thr Gly Met Asp Ser Trp Val Ala Leu Ala Ala Val Asp Ser Ala
        595                 600                 605
Val Tyr Gly Val Gln Arg Gly Ala Lys Lys Pro Leu Glu Arg Val Phe
        610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
            645                 650                 655
Ala Asn Ala Asp Asp Ser Gln Glu Asn Asp Glu Pro Cys Lys Glu Ile
        660                 665                 670
Leu Arg Pro Arg Arg Thr Leu Gln Lys Lys Ile Glu Glu Ile Ala Ala
        675                 680                 685
Lys Tyr Lys His Ser Val Val Lys Lys Cys Cys Tyr Asp Gly Ala Cys
        690                 695                 700
Val Asn Asn Asp Glu Thr Cys Glu Gln Arg Ala Ala Arg Ile Ser Leu
705                 710                 715                 720
Gly Pro Arg Cys Ile Lys Ala Phe Thr Glu Cys Cys Val Val Ala Ser
            725                 730                 735
Gln Leu Arg Ala Asn Ile Ser His Lys Asp Met Gln Leu Gly Arg Leu
        740                 745                 750
His Met Lys Thr Leu Leu Pro Val Ser Lys Pro Glu Ile Arg Ser Tyr
        755                 760                 765
Phe Pro Glu Ser Trp Leu Trp Glu Val His Leu Val Pro Arg Arg Lys
        770                 775                 780
Gln Leu Gln Phe Ala Leu Pro Asp Ser Leu Thr Thr Trp Glu Ile Gln
785                 790                 795                 800
Gly Ile Gly Ile Ser Asn Thr Gly Ile Cys Val Ala Asp Thr Val Lys
            805                 810                 815
```

```
Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
        850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
        930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu  Thr His Leu Pro Lys  Gly Ser Ala
            995                 1000                1005

Glu Ala Glu Leu Met Ser Val  Val Pro Val Phe Tyr  Val Phe His
    1010                1015                1020

Tyr Leu Glu Thr Gly Asn His  Trp Asn Ile Phe His  Ser Asp Pro
    1025                1030                1035

Leu Ile Glu Lys Gln Lys Leu  Lys Lys Lys Leu Lys  Glu Gly Met
    1040                1045                1050

Leu Ser  Ile Met Ser Tyr Arg  Asn Ala Asp Tyr Ser  Tyr Ser Val
    1055                1060                1065

Trp Lys  Gly Gly Ser Ala Ser  Thr Trp Leu Thr Ala  Phe Ala Leu
    1070                1075                1080

Arg Val  Leu Gly Gln Val Asn  Lys Tyr Val Glu Gln  Asn Gln Asn
    1085                1090                1095

Ser Ile  Cys Asn Ser Leu Leu  Trp Leu Val Glu Asn  Tyr Gln Leu
    1100                1105                1110

Asp Asn  Gly Ser Phe Lys Glu  Asn Ser Gln Tyr Gln  Pro Ile Lys
    1115                1120                1125

Leu Gln  Gly Thr Leu Pro Val  Glu Ala Arg Glu Asn  Ser Leu Tyr
    1130                1135                1140

Leu Thr  Ala Phe Thr Val Ile  Gly Ile Arg Lys Ala  Phe Asp Ile
    1145                1150                1155

Cys Pro  Leu Val Lys Ile Asp  Thr Ala Leu Ile Lys  Ala Asp Asn
    1160                1165                1170

Phe Leu  Leu Glu Asn Thr Leu  Pro Ala Gln Ser Thr  Phe Thr Leu
    1175                1180                1185

Ala Ile  Ser Ala Tyr Ala Leu  Ser Leu Gly Asp Lys  Thr His Pro
    1190                1195                1200

Gln Phe  Arg Ser Ile Val Ser  Ala Leu Lys Arg Glu  Ala Leu Val
    1205                1210                1215

Lys Gly  Asn Pro Pro Ile Tyr  Arg Phe Trp Lys Asp  Asn Leu Gln
```

-continued

|  | 1220 |  |  |  | 1225 |  |  |  | 1230 |  |
|---|---|---|---|---|---|---|---|---|---|---|

His Lys Asp Ser Ser Val Pro Asn Thr Gly Thr Ala Arg Met Val
    1235            1240            1245

Glu Thr Thr Ala Tyr Ala Leu Leu Thr Ser Leu Asn Leu Lys Asp
    1250            1255            1260

Ile Asn Tyr Val Asn Pro Val Ile Lys Trp Leu Ser Glu Glu Gln
    1265            1270            1275

Arg Tyr Gly Gly Gly Phe Tyr Ser Thr Gln Asp Thr Ile Asn Ala
    1280            1285            1290

Ile Glu Gly Leu Thr Glu Tyr Ser Leu Leu Val Lys Gln Leu Arg
    1295            1300            1305

Leu Ser Met Asp Ile Asp Val Ser Tyr Lys His Lys Gly Ala Leu
    1310            1315            1320

His Asn Tyr Lys Met Thr Asp Lys Asn Phe Leu Gly Arg Pro Val
    1325            1330            1335

Glu Val Leu Leu Asn Asp Asp Leu Ile Val Ser Thr Gly Phe Gly
    1340            1345            1350

Ser Gly Leu Ala Thr Val His Val Thr Thr Val His Lys Thr
    1355            1360            1365

Ser Thr Ser Glu Glu Val Cys Ser Phe Tyr Leu Lys Ile Asp Thr
    1370            1375            1380

Gln Asp Ile Glu Ala Ser His Tyr Arg Gly Tyr Gly Asn Ser Asp
    1385            1390            1395

Tyr Lys Arg Ile Val Ala Cys Ala Ser Tyr Lys Pro Ser Arg Glu
    1400            1405            1410

Glu Ser Ser Ser Gly Ser Ser His Ala Val Met Asp Ile Ser Leu
    1415            1420            1425

Pro Thr Gly Ile Ser Ala Asn Glu Glu Asp Leu Lys Ala Leu Val
    1430            1435            1440

Glu Gly Val Asp Gln Leu Phe Thr Asp Tyr Gln Ile Lys Asp Gly
    1445            1450            1455

His Val Ile Leu Gln Leu Asn Ser Ile Pro Ser Ser Asp Phe Leu
    1460            1465            1470

Cys Val Arg Phe Arg Ile Phe Glu Leu Phe Glu Val Gly Phe Leu
    1475            1480            1485

Ser Pro Ala Thr Phe Thr Val Tyr Glu Tyr His Arg Pro Asp Lys
    1490            1495            1500

Gln Cys Thr Met Phe Tyr Ser Thr Ser Asn Ile Lys Ile Gln Lys
    1505            1510            1515

Val Cys Glu Gly Ala Ala Cys Lys Cys Val Glu Ala Asp Cys Gly
    1520            1525            1530

Gln Met Gln Glu Glu Leu Asp Leu Thr Ile Ser Ala Glu Thr Arg
    1535            1540            1545

Lys Gln Thr Ala Cys Lys Pro Glu Ile Ala Tyr Ala Tyr Lys Val
    1550            1555            1560

Ser Ile Thr Ser Ile Thr Val Glu Asn Val Phe Val Lys Tyr Lys
    1565            1570            1575

Ala Thr Leu Leu Asp Ile Tyr Lys Thr Gly Glu Ala Val Ala Glu
    1580            1585            1590

Lys Asp Ser Glu Ile Thr Phe Ile Lys Lys Val Thr Cys Thr Asn
    1595            1600            1605

Ala Glu Leu Val Lys Gly Arg Gln Tyr Leu Ile Met Gly Lys Glu
    1610            1615            1620

```
Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 2
<211> LENGTH: 1658
<212> TYPE: PRT
<213> ORGANISM: Homo sapiens

<400> SEQUENCE: 2

Gln Glu Gln Thr Tyr Val Ile Ser Ala Pro Lys Ile Phe Arg Val Gly
1               5                   10                  15

Ala Ser Glu Asn Ile Val Ile Gln Val Tyr Gly Tyr Thr Glu Ala Phe
                20                  25                  30

Asp Ala Thr Ile Ser Ile Lys Ser Tyr Pro Asp Lys Lys Phe Ser Tyr
            35                  40                  45

Ser Ser Gly His Val His Leu Ser Ser Glu Asn Lys Phe Gln Asn Ser
        50                  55                  60

Ala Ile Leu Thr Ile Gln Pro Lys Gln Leu Pro Gly Gly Gln Asn Pro
65                  70                  75                  80

Val Ser Tyr Val Tyr Leu Glu Val Val Ser Lys His Phe Ser Lys Ser
                85                  90                  95

Lys Arg Met Pro Ile Thr Tyr Asp Asn Gly Phe Leu Phe Ile His Thr
                100                 105                 110

Asp Lys Pro Val Tyr Thr Pro Asp Gln Ser Val Lys Val Arg Val Tyr
            115                 120                 125

Ser Leu Asn Asp Asp Leu Lys Pro Ala Lys Arg Glu Thr Val Leu Thr
        130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
                180                 185                 190

Thr Thr Gly Thr Ala Tyr Phe Glu Val Lys Glu Tyr Val Leu Pro His
            195                 200                 205

Phe Ser Val Ser Ile Glu Pro Glu Tyr Asn Phe Ile Gly Tyr Lys Asn
        210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
                260                 265                 270

Met Leu Ile Asn Gly Ile Ala Gln Val Thr Phe Asp Ser Glu Thr Ala
            275                 280                 285

Val Lys Glu Leu Ser Tyr Tyr Ser Leu Glu Asp Leu Asn Asn Lys Tyr
        290                 295                 300

Leu Tyr Ile Ala Val Thr Val Ile Glu Ser Thr Gly Gly Phe Ser Glu
```

```
            305                 310                 315                 320
        Glu Ala Glu Ile Pro Gly Ile Lys Tyr Val Leu Ser Pro Tyr Lys Leu
                            325                 330                 335
        Asn Leu Val Ala Thr Pro Leu Phe Leu Lys Pro Gly Ile Pro Tyr Pro
                            340                 345                 350
        Ile Lys Val Gln Val Lys Asp Ser Leu Asp Gln Leu Val Gly Gly Val
                            355                 360                 365
        Pro Val Ile Leu Asn Ala Gln Thr Ile Asp Val Asn Gln Glu Thr Ser
                    370                 375                 380
        Asp Leu Asp Pro Ser Lys Ser Val Thr Arg Val Asp Asp Gly Val Ala
        385                 390                 395                 400
        Ser Phe Val Leu Asn Leu Pro Ser Gly Val Thr Val Leu Glu Phe Asn
                            405                 410                 415
        Val Lys Thr Asp Ala Pro Asp Leu Pro Glu Glu Asn Gln Ala Arg Glu
                            420                 425                 430
        Gly Tyr Arg Ala Ile Ala Tyr Ser Ser Leu Ser Gln Ser Tyr Leu Tyr
                            435                 440                 445
        Ile Asp Trp Thr Asp Asn His Lys Ala Leu Leu Val Gly Glu His Leu
                    450                 455                 460
        Asn Ile Ile Val Thr Pro Lys Ser Pro Tyr Ile Asp Lys Ile Thr His
        465                 470                 475                 480
        Tyr Asn Tyr Leu Ile Leu Ser Lys Gly Lys Ile Ile His Phe Gly Thr
                            485                 490                 495
        Arg Glu Lys Phe Ser Asp Ala Ser Tyr Gln Ser Ile Asn Ile Pro Val
                            500                 505                 510
        Thr Gln Asn Met Val Pro Ser Ser Arg Leu Leu Val Tyr Tyr Ile Val
                            515                 520                 525
        Thr Gly Glu Gln Thr Ala Glu Leu Val Ser Asp Ser Val Trp Leu Asn
                    530                 535                 540
        Ile Glu Glu Lys Cys Gly Asn Gln Leu Gln Val His Leu Ser Pro Asp
        545                 550                 555                 560
        Ala Asp Ala Tyr Ser Pro Gly Gln Thr Val Ser Leu Asn Met Ala Thr
                            565                 570                 575
        Gly Met Asp Ser Trp Val Ala Leu Ala Ala Val Asp Ser Ala Val Tyr
                            580                 585                 590
        Gly Val Gln Arg Gly Ala Lys Lys Pro Leu Glu Arg Val Phe Gln Phe
                            595                 600                 605
        Leu Glu Lys Ser Asp Leu Gly Cys Gly Ala Gly Gly Leu Asn Asn
                    610                 615                 620
        Ala Asn Val Phe His Leu Ala Gly Leu Thr Phe Leu Thr Asn Ala Asn
        625                 630                 635                 640
        Ala Asp Asp Ser Gln Glu Asn Asp Glu Pro Cys Lys Glu Ile Leu Arg
                            645                 650                 655
        Pro Arg Arg Thr Leu Gln Lys Lys Ile Glu Glu Ile Ala Ala Lys Tyr
                            660                 665                 670
        Lys His Ser Val Val Lys Lys Cys Cys Tyr Asp Gly Ala Cys Val Asn
                            675                 680                 685
        Asn Asp Glu Thr Cys Glu Gln Arg Ala Ala Arg Ile Ser Leu Gly Pro
                    690                 695                 700
        Arg Cys Ile Lys Ala Phe Thr Glu Cys Cys Val Val Ala Ser Gln Leu
        705                 710                 715                 720
        Arg Ala Asn Ile Ser His Lys Asp Met Gln Leu Gly Arg Leu His Met
                            725                 730                 735
```

```
Lys Thr Leu Leu Pro Val Ser Lys Pro Glu Ile Arg Ser Tyr Phe Pro
            740                 745                 750

Glu Ser Trp Leu Trp Glu Val His Leu Val Pro Arg Lys Gln Leu
            755                 760                 765

Gln Phe Ala Leu Pro Asp Ser Leu Thr Thr Trp Glu Ile Gln Gly Ile
770                 775                 780

Gly Ile Ser Asn Thr Gly Ile Cys Val Ala Asp Thr Val Lys Ala Lys
785                 790                 795                 800

Val Phe Lys Asp Val Phe Leu Glu Met Asn Ile Pro Tyr Ser Val Val
            805                 810                 815

Arg Gly Glu Gln Ile Gln Leu Lys Gly Thr Val Tyr Asn Tyr Arg Thr
            820                 825                 830

Ser Gly Met Gln Phe Cys Val Lys Met Ser Ala Val Glu Gly Ile Cys
            835                 840                 845

Thr Ser Glu Ser Pro Val Ile Asp His Gln Gly Thr Lys Ser Ser Lys
850                 855                 860

Cys Val Arg Gln Lys Val Glu Gly Ser Ser His Leu Val Thr Phe
865                 870                 875                 880

Thr Val Leu Pro Leu Glu Ile Gly Leu His Asn Ile Asn Phe Ser Leu
            885                 890                 895

Glu Thr Trp Phe Gly Lys Glu Ile Leu Val Lys Thr Leu Arg Val Val
            900                 905                 910

Pro Glu Gly Val Lys Arg Glu Ser Tyr Ser Gly Val Thr Leu Asp Pro
            915                 920                 925

Arg Gly Ile Tyr Gly Thr Ile Ser Arg Arg Lys Glu Phe Pro Tyr Arg
            930                 935                 940

Ile Pro Leu Asp Leu Val Pro Lys Thr Glu Ile Lys Arg Ile Leu Ser
945                 950                 955                 960

Val Lys Gly Leu Leu Val Gly Glu Ile Leu Ser Ala Val Leu Ser Gln
            965                 970                 975

Glu Gly Ile Asn Ile Leu Thr His Leu Pro Lys Gly Ser Ala Glu Ala
            980                 985                 990

Glu Leu Met Ser Val Val Pro Val Phe Tyr Val Phe His Tyr Leu Glu
            995                 1000                1005

Thr Gly Asn His Trp Asn Ile Phe His Ser Asp Pro Leu Ile Glu
    1010                1015                1020

Lys Gln Lys Leu Lys Lys Lys Leu Lys Glu Gly Met Leu Ser Ile
    1025                1030                1035

Met Ser Tyr Arg Asn Ala Asp Tyr Ser Tyr Ser Val Trp Lys Gly
    1040                1045                1050

Gly Ser Ala Ser Thr Trp Leu Thr Ala Phe Ala Leu Arg Val Leu
    1055                1060                1065

Gly Gln Val Asn Lys Tyr Val Glu Gln Asn Gln Asn Ser Ile Cys
    1070                1075                1080

Asn Ser Leu Leu Trp Leu Val Glu Asn Tyr Gln Leu Asp Asn Gly
    1085                1090                1095

Ser Phe Lys Glu Asn Ser Gln Tyr Gln Pro Ile Lys Leu Gln Gly
    1100                1105                1110

Thr Leu Pro Val Glu Ala Arg Glu Asn Ser Leu Tyr Leu Thr Ala
    1115                1120                1125

Phe Thr Val Ile Gly Ile Arg Lys Ala Phe Asp Ile Cys Pro Leu
    1130                1135                1140
```

-continued

Val Lys Ile Asp Thr Ala Leu Ile Lys Ala Asp Asn Phe Leu Leu
1145                1150                1155

Glu Asn Thr Leu Pro Ala Gln Ser Thr Phe Thr Leu Ala Ile Ser
1160                1165                1170

Ala Tyr Ala Leu Ser Leu Gly Asp Lys Thr His Pro Gln Phe Arg
1175                1180                1185

Ser Ile Val Ser Ala Leu Lys Arg Glu Ala Leu Val Lys Gly Asn
1190                1195                1200

Pro Pro Ile Tyr Arg Phe Trp Lys Asp Asn Leu Gln His Lys Asp
1205                1210                1215

Ser Ser Val Pro Asn Thr Gly Thr Ala Arg Met Val Glu Thr Thr
1220                1225                1230

Ala Tyr Ala Leu Leu Thr Ser Leu Asn Leu Lys Asp Ile Asn Tyr
1235                1240                1245

Val Asn Pro Val Ile Lys Trp Leu Ser Glu Glu Gln Arg Tyr Gly
1250                1255                1260

Gly Gly Phe Tyr Ser Thr Gln Asp Thr Ile Asn Ala Ile Glu Gly
1265                1270                1275

Leu Thr Glu Tyr Ser Leu Leu Val Lys Gln Leu Arg Leu Ser Met
1280                1285                1290

Asp Ile Asp Val Ser Tyr Lys His Lys Gly Ala Leu His Asn Tyr
1295                1300                1305

Lys Met Thr Asp Lys Asn Phe Leu Gly Arg Pro Val Glu Val Leu
1310                1315                1320

Leu Asn Asp Asp Leu Ile Val Ser Thr Gly Phe Gly Ser Gly Leu
1325                1330                1335

Ala Thr Val His Val Thr Thr Val Val His Lys Thr Ser Thr Ser
1340                1345                1350

Glu Glu Val Cys Ser Phe Tyr Leu Lys Ile Asp Thr Gln Asp Ile
1355                1360                1365

Glu Ala Ser His Tyr Arg Gly Tyr Gly Asn Ser Asp Tyr Lys Arg
1370                1375                1380

Ile Val Ala Cys Ala Ser Tyr Lys Pro Ser Arg Glu Glu Ser Ser
1385                1390                1395

Ser Gly Ser Ser His Ala Val Met Asp Ile Ser Leu Pro Thr Gly
1400                1405                1410

Ile Ser Ala Asn Glu Glu Asp Leu Lys Ala Leu Val Glu Gly Val
1415                1420                1425

Asp Gln Leu Phe Thr Asp Tyr Gln Ile Lys Asp Gly His Val Ile
1430                1435                1440

Leu Gln Leu Asn Ser Ile Pro Ser Ser Asp Phe Leu Cys Val Arg
1445                1450                1455

Phe Arg Ile Phe Glu Leu Phe Glu Val Gly Phe Leu Ser Pro Ala
1460                1465                1470

Thr Phe Thr Val Tyr Glu Tyr His Arg Pro Asp Lys Gln Cys Thr
1475                1480                1485

Met Phe Tyr Ser Thr Ser Asn Ile Lys Ile Gln Lys Val Cys Glu
1490                1495                1500

Gly Ala Ala Cys Lys Cys Val Glu Ala Asp Cys Gly Gln Met Gln
1505                1510                1515

Glu Glu Leu Asp Leu Thr Ile Ser Ala Glu Thr Arg Lys Gln Thr
1520                1525                1530

Ala Cys Lys Pro Glu Ile Ala Tyr Ala Tyr Lys Val Ser Ile Thr

-continued

```
           1535                1540                1545

Ser Ile Thr Val Glu Asn Val Phe Val Lys Tyr Lys Ala Thr Leu
    1550                1555                1560

Leu Asp Ile Tyr Lys Thr Gly Glu Ala Val Ala Glu Lys Asp Ser
    1565                1570                1575

Glu Ile Thr Phe Ile Lys Lys Val Thr Cys Thr Asn Ala Glu Leu
    1580                1585                1590

Val Lys Gly Arg Gln Tyr Leu Ile Met Gly Lys Glu Ala Leu Gln
    1595                1600                1605

Ile Lys Tyr Asn Phe Ser Phe Arg Tyr Ile Tyr Pro Leu Asp Ser
    1610                1615                1620

Leu Thr Trp Ile Glu Tyr Trp Pro Arg Asp Thr Thr Cys Ser Ser
    1625                1630                1635

Cys Gln Ala Phe Leu Ala Asn Leu Asp Glu Phe Ala Glu Asp Ile
    1640                1645                1650

Phe Leu Asn Gly Cys
    1655

<210> SEQ ID NO 3
<211> LENGTH: 999
<212> TYPE: PRT
<213> ORGANISM: Homo sapiens

<400> SEQUENCE: 3

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
                20                  25                  30

Thr Cys Glu Gln Arg Ala Ala Arg Ile Ser Leu Gly Pro Arg Cys Ile
            35                  40                  45

Lys Ala Phe Thr Glu Cys Cys Val Val Ala Ser Gln Leu Arg Ala Asn
        50                  55                  60

Ile Ser His Lys Asp Met Gln Leu Gly Arg Leu His Met Lys Thr Leu
65                  70                  75                  80

Leu Pro Val Ser Lys Pro Glu Ile Arg Ser Tyr Phe Pro Glu Ser Trp
                85                  90                  95

Leu Trp Glu Val His Leu Val Pro Arg Arg Lys Gln Leu Gln Phe Ala
            100                 105                 110

Leu Pro Asp Ser Leu Thr Thr Trp Glu Ile Gln Gly Ile Gly Ile Ser
        115                 120                 125

Asn Thr Gly Ile Cys Val Ala Asp Thr Val Lys Ala Lys Val Phe Lys
    130                 135                 140

Asp Val Phe Leu Glu Met Asn Ile Pro Tyr Ser Val Val Arg Gly Glu
145                 150                 155                 160

Gln Ile Gln Leu Lys Gly Thr Val Tyr Asn Tyr Arg Thr Ser Gly Met
                165                 170                 175

Gln Phe Cys Val Lys Met Ser Ala Val Glu Gly Ile Cys Thr Ser Glu
            180                 185                 190

Ser Pro Val Ile Asp His Gln Gly Thr Lys Ser Ser Lys Cys Val Arg
        195                 200                 205

Gln Lys Val Glu Gly Ser Ser Ser His Leu Val Thr Phe Thr Val Leu
    210                 215                 220

Pro Leu Glu Ile Gly Leu His Asn Ile Asn Phe Ser Leu Glu Thr Trp
225                 230                 235                 240
```

```
Phe Gly Lys Glu Ile Leu Val Lys Thr Leu Arg Val Pro Glu Gly
                245                 250                 255

Val Lys Arg Glu Ser Tyr Ser Gly Val Thr Leu Asp Pro Arg Gly Ile
            260                 265                 270

Tyr Gly Thr Ile Ser Arg Arg Lys Glu Phe Pro Tyr Arg Ile Pro Leu
        275                 280                 285

Asp Leu Val Pro Lys Thr Glu Ile Lys Arg Ile Leu Ser Val Lys Gly
    290                 295                 300

Leu Leu Val Gly Glu Ile Leu Ser Ala Val Leu Ser Gln Glu Gly Ile
305                 310                 315                 320

Asn Ile Leu Thr His Leu Pro Lys Gly Ser Ala Glu Ala Glu Leu Met
                325                 330                 335

Ser Val Val Pro Val Phe Tyr Val Phe His Tyr Leu Glu Thr Gly Asn
            340                 345                 350

His Trp Asn Ile Phe His Ser Asp Pro Leu Ile Glu Lys Gln Lys Leu
        355                 360                 365

Lys Lys Lys Leu Lys Glu Gly Met Leu Ser Ile Met Ser Tyr Arg Asn
    370                 375                 380

Ala Asp Tyr Ser Tyr Ser Val Trp Lys Gly Gly Ser Ala Ser Thr Trp
385                 390                 395                 400

Leu Thr Ala Phe Ala Leu Arg Val Leu Gly Gln Val Asn Lys Tyr Val
                405                 410                 415

Glu Gln Asn Gln Asn Ser Ile Cys Asn Ser Leu Leu Trp Leu Val Glu
            420                 425                 430

Asn Tyr Gln Leu Asp Asn Gly Ser Phe Lys Glu Asn Ser Gln Tyr Gln
        435                 440                 445

Pro Ile Lys Leu Gln Gly Thr Leu Pro Val Glu Ala Arg Glu Asn Ser
    450                 455                 460

Leu Tyr Leu Thr Ala Phe Thr Val Ile Gly Ile Arg Lys Ala Phe Asp
465                 470                 475                 480

Ile Cys Pro Leu Val Lys Ile Asp Thr Ala Leu Ile Lys Ala Asp Asn
                485                 490                 495

Phe Leu Leu Glu Asn Thr Leu Pro Ala Gln Ser Thr Phe Thr Leu Ala
            500                 505                 510

Ile Ser Ala Tyr Ala Leu Ser Leu Gly Asp Lys Thr His Pro Gln Phe
        515                 520                 525

Arg Ser Ile Val Ser Ala Leu Lys Arg Glu Ala Leu Val Lys Gly Asn
    530                 535                 540

Pro Pro Ile Tyr Arg Phe Trp Lys Asp Asn Leu Gln His Lys Asp Ser
545                 550                 555                 560

Ser Val Pro Asn Thr Gly Thr Ala Arg Met Val Glu Thr Thr Ala Tyr
                565                 570                 575

Ala Leu Leu Thr Ser Leu Asn Leu Lys Asp Ile Asn Tyr Val Asn Pro
            580                 585                 590

Val Ile Lys Trp Leu Ser Glu Glu Gln Arg Tyr Gly Gly Gly Phe Tyr
        595                 600                 605

Ser Thr Gln Asp Thr Ile Asn Ala Ile Glu Gly Leu Thr Glu Tyr Ser
    610                 615                 620

Leu Leu Val Lys Gln Leu Arg Leu Ser Met Asp Ile Asp Val Ser Tyr
625                 630                 635                 640

Lys His Lys Gly Ala Leu His Asn Tyr Lys Met Thr Asp Lys Asn Phe
                645                 650                 655

Leu Gly Arg Pro Val Glu Val Leu Leu Asn Asp Asp Leu Ile Val Ser
```

```
                    660                 665                 670
Thr Gly Phe Gly Ser Gly Leu Ala Thr Val His Val Thr Val Val
                675                 680                 685
His Lys Thr Ser Thr Ser Glu Glu Val Cys Ser Phe Tyr Leu Lys Ile
            690                 695                 700
Asp Thr Gln Asp Ile Glu Ala Ser His Tyr Arg Gly Tyr Gly Asn Ser
705                 710                 715                 720
Asp Tyr Lys Arg Ile Val Ala Cys Ala Ser Tyr Lys Pro Ser Arg Glu
                725                 730                 735
Glu Ser Ser Ser Gly Ser Ser His Ala Val Met Asp Ile Ser Leu Pro
                740                 745                 750
Thr Gly Ile Ser Ala Asn Glu Glu Asp Leu Lys Ala Leu Val Glu Gly
                755                 760                 765
Val Asp Gln Leu Phe Thr Asp Tyr Gln Ile Lys Asp Gly His Val Ile
                770                 775                 780
Leu Gln Leu Asn Ser Ile Pro Ser Ser Asp Phe Leu Cys Val Arg Phe
785                 790                 795                 800
Arg Ile Phe Glu Leu Phe Glu Val Gly Phe Leu Ser Pro Ala Thr Phe
                805                 810                 815
Thr Val Tyr Glu Tyr His Arg Pro Asp Lys Gln Cys Thr Met Phe Tyr
                820                 825                 830
Ser Thr Ser Asn Ile Lys Ile Gln Lys Val Cys Glu Gly Ala Ala Cys
            835                 840                 845
Lys Cys Val Glu Ala Asp Cys Gly Gln Met Gln Glu Glu Leu Asp Leu
        850                 855                 860
Thr Ile Ser Ala Glu Thr Arg Lys Gln Thr Ala Cys Lys Pro Glu Ile
865                 870                 875                 880
Ala Tyr Ala Tyr Lys Val Ser Ile Thr Ser Ile Thr Val Glu Asn Val
                885                 890                 895
Phe Val Lys Tyr Lys Ala Thr Leu Leu Asp Ile Tyr Lys Thr Gly Glu
                900                 905                 910
Ala Val Ala Glu Lys Asp Ser Glu Ile Thr Phe Ile Lys Lys Val Thr
            915                 920                 925
Cys Thr Asn Ala Glu Leu Val Lys Gly Arg Gln Tyr Leu Ile Met Gly
        930                 935                 940
Lys Glu Ala Leu Gln Ile Lys Tyr Asn Phe Ser Phe Arg Tyr Ile Tyr
945                 950                 955                 960
Pro Leu Asp Ser Leu Thr Trp Ile Glu Tyr Trp Pro Arg Asp Thr Thr
                965                 970                 975
Cys Ser Ser Cys Gln Ala Phe Leu Ala Asn Leu Asp Glu Phe Ala Glu
                980                 985                 990
Asp Ile Phe Leu Asn Gly Cys
        995

<210> SEQ ID NO 4
<211> LENGTH: 655
<212> TYPE: PRT
<213> ORGANISM: Homo sapiens

<400> SEQUENCE: 4

Gln Glu Gln Thr Tyr Val Ile Ser Ala Pro Lys Ile Phe Arg Val Gly
1               5                   10                  15
Ala Ser Glu Asn Ile Val Ile Gln Val Tyr Gly Tyr Thr Glu Ala Phe
            20                  25                  30
```

```
Asp Ala Thr Ile Ser Ile Lys Ser Tyr Pro Asp Lys Lys Phe Ser Tyr
            35                  40                  45

Ser Ser Gly His Val His Leu Ser Ser Glu Asn Lys Phe Gln Asn Ser
 50                  55                  60

Ala Ile Leu Thr Ile Gln Pro Lys Gln Leu Pro Gly Gly Gln Asn Pro
 65                  70                  75                  80

Val Ser Tyr Val Tyr Leu Glu Val Val Ser Lys His Phe Ser Lys Ser
                 85                  90                  95

Lys Arg Met Pro Ile Thr Tyr Asp Asn Gly Phe Leu Phe Ile His Thr
            100                 105                 110

Asp Lys Pro Val Tyr Thr Pro Asp Gln Ser Val Lys Val Arg Val Tyr
            115                 120                 125

Ser Leu Asn Asp Asp Leu Lys Pro Ala Lys Arg Glu Thr Val Leu Thr
130                 135                 140

Phe Ile Asp Pro Glu Gly Ser Glu Val Asp Met Val Glu Glu Ile Asp
145                 150                 155                 160

His Ile Gly Ile Ile Ser Phe Pro Asp Phe Lys Ile Pro Ser Asn Pro
                165                 170                 175

Arg Tyr Gly Met Trp Thr Ile Lys Ala Lys Tyr Lys Glu Asp Phe Ser
            180                 185                 190

Thr Thr Gly Thr Ala Tyr Phe Glu Val Lys Glu Tyr Val Leu Pro His
        195                 200                 205

Phe Ser Val Ser Ile Glu Pro Glu Tyr Asn Phe Ile Gly Tyr Lys Asn
    210                 215                 220

Phe Lys Asn Phe Glu Ile Thr Ile Lys Ala Arg Tyr Phe Tyr Asn Lys
225                 230                 235                 240

Val Val Thr Glu Ala Asp Val Tyr Ile Thr Phe Gly Ile Arg Glu Asp
                245                 250                 255

Leu Lys Asp Asp Gln Lys Glu Met Met Gln Thr Ala Met Gln Asn Thr
            260                 265                 270

Met Leu Ile Asn Gly Ile Ala Gln Val Thr Phe Asp Ser Glu Thr Ala
        275                 280                 285

Val Lys Glu Leu Ser Tyr Tyr Ser Leu Glu Asp Leu Asn Asn Lys Tyr
    290                 295                 300

Leu Tyr Ile Ala Val Thr Val Ile Glu Ser Thr Gly Gly Phe Ser Glu
305                 310                 315                 320

Glu Ala Glu Ile Pro Gly Ile Lys Tyr Val Leu Ser Pro Tyr Lys Leu
                325                 330                 335

Asn Leu Val Ala Thr Pro Leu Phe Leu Lys Pro Gly Ile Pro Tyr Pro
            340                 345                 350

Ile Lys Val Gln Val Lys Asp Ser Leu Asp Gln Leu Val Gly Gly Val
        355                 360                 365

Pro Val Ile Leu Asn Ala Gln Thr Ile Asp Val Asn Gln Glu Thr Ser
    370                 375                 380

Asp Leu Asp Pro Ser Lys Ser Val Thr Arg Val Asp Asp Gly Val Ala
385                 390                 395                 400

Ser Phe Val Leu Asn Leu Pro Ser Gly Val Thr Val Leu Glu Phe Asn
                405                 410                 415

Val Lys Thr Asp Ala Pro Asp Leu Pro Glu Glu Asn Gln Ala Arg Glu
            420                 425                 430

Gly Tyr Arg Ala Ile Ala Tyr Ser Ser Leu Ser Gln Ser Tyr Leu Tyr
        435                 440                 445

Ile Asp Trp Thr Asp Asn His Lys Ala Leu Leu Val Gly Glu His Leu
```

```
                  450                 455                 460
Asn Ile Ile Val Thr Pro Lys Ser Pro Tyr Ile Asp Lys Ile Thr His
465                 470                 475                 480

Tyr Asn Tyr Leu Ile Leu Ser Lys Gly Lys Ile Ile His Phe Gly Thr
                    485                 490                 495

Arg Glu Lys Phe Ser Asp Ala Ser Tyr Gln Ser Ile Asn Ile Pro Val
                500                 505                 510

Thr Gln Asn Met Val Pro Ser Ser Arg Leu Leu Val Tyr Tyr Ile Val
            515                 520                 525

Thr Gly Glu Gln Thr Ala Glu Leu Val Ser Asp Ser Val Trp Leu Asn
        530                 535                 540

Ile Glu Glu Lys Cys Gly Asn Gln Leu Gln Val His Leu Ser Pro Asp
545                 550                 555                 560

Ala Asp Ala Tyr Ser Pro Gly Gln Thr Val Ser Leu Asn Met Ala Thr
                    565                 570                 575

Gly Met Asp Ser Trp Val Ala Leu Ala Ala Val Asp Ser Ala Val Tyr
                580                 585                 590

Gly Val Gln Arg Gly Ala Lys Lys Pro Leu Glu Arg Val Phe Gln Phe
            595                 600                 605

Leu Glu Lys Ser Asp Leu Gly Cys Gly Ala Gly Gly Gly Leu Asn Asn
        610                 615                 620

Ala Asn Val Phe His Leu Ala Gly Leu Thr Phe Leu Thr Asn Ala Asn
625                 630                 635                 640

Ala Asp Asp Ser Gln Glu Asn Asp Glu Pro Cys Lys Glu Ile Leu
                    645                 650                 655

<210> SEQ ID NO 5
<211> LENGTH: 21
<212> TYPE: PRT
<213> ORGANISM: Homo sapiens

<400> SEQUENCE: 5

Val Ile Asp His Gln Gly Thr Lys Ser Ser Lys Cys Val Arg Gln Lys
1               5                   10                  15

Val Glu Gly Ser Ser
            20

<210> SEQ ID NO 6
<211> LENGTH: 5
<212> TYPE: PRT
<213> ORGANISM: Homo sapiens

<400> SEQUENCE: 6

Lys Ser Ser Lys Cys
1               5

<210> SEQ ID NO 7
<211> LENGTH: 127
<212> TYPE: PRT
<213> ORGANISM: Homo sapiens

<400> SEQUENCE: 7

Asn Phe Ser Leu Glu Thr Trp Phe Gly Lys Glu Ile Leu Val Lys Thr
1               5                   10                  15

Leu Arg Val Val Pro Glu Gly Val Lys Arg Glu Ser Tyr Ser Gly Val
            20                  25                  30

Thr Leu Asp Pro Arg Gly Ile Tyr Gly Thr Ile Ser Arg Arg Lys Glu
        35                  40                  45
```

```
Phe Pro Tyr Arg Ile Pro Leu Asp Leu Val Pro Lys Thr Glu Ile Lys
    50                  55                  60

Arg Ile Leu Ser Val Lys Gly Leu Leu Val Gly Glu Ile Leu Ser Ala
65                  70                  75                  80

Val Leu Ser Gln Glu Gly Ile Asn Ile Leu Thr His Leu Pro Lys Gly
                    85                  90                  95

Ser Ala Glu Ala Glu Leu Met Ser Val Val Pro Val Phe Tyr Val Phe
                100                 105                 110

His Tyr Leu Glu Thr Gly Asn His Trp Asn Ile Phe His Ser Asp
                115                 120                 125

<210> SEQ ID NO 8
<211> LENGTH: 200
<212> TYPE: PRT
<213> ORGANISM: Homo sapiens

<400> SEQUENCE: 8

Ser Glu Ser Pro Val Ile Asp His Gln Gly Thr Lys Ser Ser Lys Cys
1               5                   10                  15

Val Arg Gln Lys Val Glu Gly Ser Ser Ser His Leu Val Thr Phe Thr
                20                  25                  30

Val Leu Pro Leu Glu Ile Gly Leu His Asn Ile Asn Phe Ser Leu Glu
                35                  40                  45

Thr Trp Phe Gly Lys Glu Ile Leu Val Lys Thr Leu Arg Val Val Pro
    50                  55                  60

Glu Gly Val Lys Arg Glu Ser Tyr Ser Gly Val Thr Leu Asp Pro Arg
65                  70                  75                  80

Gly Ile Tyr Gly Thr Ile Ser Arg Arg Lys Glu Phe Pro Tyr Arg Ile
                85                  90                  95

Pro Leu Asp Leu Val Pro Lys Thr Glu Ile Lys Arg Ile Leu Ser Val
                100                 105                 110

Lys Gly Leu Leu Val Gly Glu Ile Leu Ser Ala Val Leu Ser Gln Glu
                115                 120                 125

Gly Ile Asn Ile Leu Thr His Leu Pro Lys Gly Ser Ala Glu Ala Glu
130                 135                 140

Leu Met Ser Val Val Pro Val Phe Tyr Val Phe His Tyr Leu Glu Thr
145                 150                 155                 160

Gly Asn His Trp Asn Ile Phe His Ser Asp Pro Leu Ile Glu Lys Gln
                165                 170                 175

Lys Leu Lys Lys Lys Leu Lys Gly Met Leu Ser Ile Met Ser Tyr
                180                 185                 190

Arg Asn Ala Asp Tyr Ser Tyr Ser
        195                 200

<210> SEQ ID NO 9
<211> LENGTH: 30
<212> TYPE: PRT
<213> ORGANISM: Homo sapiens

<400> SEQUENCE: 9

Ser His Lys Asp Met Gln Leu Gly Arg Leu His Met Lys Thr Leu Leu
1               5                   10                  15

Pro Val Ser Lys Pro Glu Ile Arg Ser Tyr Phe Pro Glu Ser
                20                  25                  30

<210> SEQ ID NO 10
```

```
<211> LENGTH: 325
<212> TYPE: PRT
<213> ORGANISM: Homo sapiens

<400> SEQUENCE: 10

Ser His Lys Asp Met Gln Leu Gly Arg Leu His Met Lys Thr Leu Leu
1               5                   10                  15

Pro Val Ser Lys Pro Glu Ile Arg Ser Tyr Phe Pro Glu Ser Trp Leu
            20                  25                  30

Trp Glu Val His Leu Val Pro Arg Arg Lys Gln Leu Gln Phe Ala Leu
        35                  40                  45

Pro Asp Ser Leu Thr Thr Trp Glu Ile Gln Gly Ile Gly Ile Ser Asn
50                  55                  60

Thr Gly Ile Cys Val Ala Asp Thr Val Lys Ala Lys Val Phe Lys Asp
65                  70                  75                  80

Val Phe Leu Glu Met Asn Ile Pro Tyr Ser Val Val Arg Gly Glu Gln
                85                  90                  95

Ile Gln Leu Lys Gly Thr Val Tyr Asn Tyr Arg Thr Ser Gly Met Gln
            100                 105                 110

Phe Cys Val Lys Met Ser Ala Val Glu Gly Ile Cys Thr Ser Glu Ser
        115                 120                 125

Pro Val Ile Asp His Gln Gly Thr Lys Ser Ser Lys Cys Val Arg Gln
130                 135                 140

Lys Val Glu Gly Ser Ser Ser His Leu Val Thr Phe Thr Val Leu Pro
145                 150                 155                 160

Leu Glu Ile Gly Leu His Asn Ile Asn Phe Ser Leu Glu Thr Trp Phe
                165                 170                 175

Gly Lys Glu Ile Leu Val Lys Thr Leu Arg Val Val Pro Glu Gly Val
            180                 185                 190

Lys Arg Glu Ser Tyr Ser Gly Val Thr Leu Asp Pro Arg Gly Ile Tyr
        195                 200                 205

Gly Thr Ile Ser Arg Arg Lys Glu Phe Pro Tyr Arg Ile Pro Leu Asp
210                 215                 220

Leu Val Pro Lys Thr Glu Ile Lys Arg Ile Leu Ser Val Lys Gly Leu
225                 230                 235                 240

Leu Val Gly Glu Ile Leu Ser Ala Val Leu Ser Gln Glu Gly Ile Asn
                245                 250                 255

Ile Leu Thr His Leu Pro Lys Gly Ser Ala Glu Ala Glu Leu Met Ser
            260                 265                 270

Val Val Pro Val Phe Tyr Val Phe His Tyr Leu Glu Thr Gly Asn His
        275                 280                 285

Trp Asn Ile Phe His Ser Asp Pro Leu Ile Glu Lys Gln Lys Leu Lys
290                 295                 300

Lys Lys Leu Lys Glu Gly Met Leu Ser Ile Met Ser Tyr Arg Asn Ala
305                 310                 315                 320

Asp Tyr Ser Tyr Ser
                325

<210> SEQ ID NO 11
<211> LENGTH: 17
<212> TYPE: PRT
<213> ORGANISM: Homo sapiens

<400> SEQUENCE: 11

Asp His Gln Gly Thr Lys Ser Ser Lys Cys Val Arg Gln Lys Val Glu
1               5                   10                  15
```

```
Gly

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60
```

```
Lys Asp Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Tyr Phe Phe Gly Ser Ser Pro Asn Trp Tyr Phe Asp Val Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Cys Ser Arg Ser Thr Ser Glu Ser Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
            195                 200                 205
His Lys Pro Ser Asn Thr Lys Val Asp Lys Thr Val Glu Arg Lys Cys
210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
            435                 440                 445
```

KITS COMPRISING FORMULATIONS OF ANTI-C5 ANTIBODIES

RELATED APPLICATIONS

This application is a continuation of U.S. application Ser. No. 15/176,774, filed Jun. 8, 2016, (now U.S. Pat. No. 9,556,263), which is a continuation of U.S. application Ser. No. 15/096,747, filed Apr. 12, 2016, (now U.S. Pat. No. 9,409,980), which is a divisional of U.S. application Ser. No. 13/413,268, filed Mar. 6, 2012, (now U.S. Pat. No. 9,415,102), which claims the benefit of priority to U.S. Provisional Application Ser. No. 61/450,334, filed Mar. 8, 2011. The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Dec. 20, 2016, is named AXJ_160CP2DVCN2_SL.txt, and is 56,233 bytes in size.

TECHNICAL FIELD

The field of the invention is medicine, immunology, molecular biology, and protein chemistry.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

The complement cascade can progress via the classical pathway (CP), the lectin pathway, or the alternative pathway (AP). The lectin pathway is typically initiated with binding of mannose-binding lectin (MBL) to high mannose substrates. The AP can be antibody independent, and can be initiated by certain molecules on pathogen surfaces. The CP is typically initiated by antibody recognition of, and binding to, an antigenic site on a target cell. These pathways converge at the C3 convertase—the point where complement component C3 is cleaved by an active protease to yield C3a and C3b.

The AP C3 convertase is initiated by the spontaneous hydrolysis of complement component C3, which is abundant in the plasma in the blood. This process, also known as "tickover," occurs through the spontaneous cleavage of a thioester bond in C3 to form C3i or C3($H_2O$). Tickover is facilitated by the presence of surfaces that support the binding of activated C3 and/or have neutral or positive charge characteristics (e.g., bacterial cell surfaces). This formation of C3($H_2O$) allows for the binding of plasma protein Factor B, which in turn allows Factor D to cleave Factor B into Ba and Bb. The Bb fragment remains bound to C3 to form a complex containing C3($H_2O$)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to thus form the surface-bound AP C3 convertase complex containing C3b, Bb. (See, e.g., Müller-Eberhard (1988) *Ann Rev Biochem* 57:321-347.)

The AP C5 convertase—(C3b)$_2$,Bb—is formed upon addition of a second C3b monomer to the AP C3 convertase. (See, e.g., Medicus et al. (1976) *J Exp Med* 144:1076-1093 and Fearon et al. (1975) *J Exp Med* 142:856-863.) The role of the second C3b molecule is to bind C5 and present it for cleavage by Bb. (See, e.g., Isenman et al. (1980) *J Immunol* 124:326-331.) The AP C3 and C5 convertases are stabilized by the addition of the trimeric protein properdin as described in, e.g., Medicus et al. (1976), supra. However, properdin binding is not required to form a functioning alternative pathway C3 or C5 convertase. See, e.g., Schreiber et al. (1978) *Proc Natl Acad Sci USA* 75: 3948-3952 and Sissons et al. (1980) *Proc Natl Acad Sci USA* 77: 559-562.

The CP C3 convertase is formed upon interaction of complement component C1, which is a complex of C1q, C1r, and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to thereby generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase—C4b,C2a,C3b—is formed upon addition of a C3b monomer to the CP C3 convertase. See, e.g., Miller-Eberhard (1988), supra and Cooper et al. (1970) *J Exp Med* 132:775-793.

In addition to its role in C3 and C5 convertases, C3b also functions as an opsonin through its interaction with complement receptors present on the surfaces of antigen-presenting cells such as macrophages and dendritic cells. The opsonic function of C3b is generally considered to be one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5, which is a 190 kDa beta globulin found in normal human serum at approximately 75 μg/ml (0.4 μM). C5 is glycosylated, with about 1.5-3 percent of its mass attributed to carbohydrate. Mature C5 is a heterodimer of a 999 amino acid 115 kDa alpha chain that is disulfide linked to a 655 amino acid 75 kDa beta chain. C5 is synthesized as a single chain precursor protein product of a single copy gene (Haviland et al. (1991) *J Immunol* 146:362-368). The cDNA sequence of the transcript of this gene predicts a secreted pro-C5 precursor of 1658 amino acids along with an 18 amino acid leader sequence (see, e.g., U.S. Pat. No. 6,355,245).

The pro-C5 precursor is cleaved after amino acids 655 and 659, to yield the beta chain as an amino terminal fragment (amino acid residues +1 to 655 of the above sequence) and the alpha chain as a carboxyl terminal fragment (amino acid residues 660 to 1658 of the above sequence), with four amino acids (amino acid residues 656-659 of the above sequence) deleted between the two.

C5a is cleaved from the alpha chain of C5 by either alternative or classical C5 convertase as an amino terminal fragment comprising the first 74 amino acids of the alpha chain (i.e., amino acid residues 660-733 of the above sequence). Approximately 20 percent of the 11 kDa mass of C5a is attributed to carbohydrate. The cleavage site for convertase action is at, or immediately adjacent to, amino acid residue 733 of the above sequence. A compound that would bind at, or adjacent, to this cleavage site would have the potential to block access of the C5 convertase enzymes to the cleavage site and thereby act as a complement inhibitor. A compound that binds to C5 at a site distal to the cleavage site could also have the potential to block C5 cleavage, for example, by way of steric hindrance-mediated inhibition of the interaction between C5 and the C5 convertase. A compound, in a mechanism of action consistent with that of the tick saliva complement inhibitor OmCI, may also prevent C5 cleavage by reducing flexibility of the C345C domain of the alpha chain of C5, which reduces access of the C5 convertase to the cleavage site of C5. See, e.g., Fredslund et al. (2008) *Nat Immunol* 9(7):753-760.

C5 can also be activated by means other than C5 convertase activity. Limited trypsin digestion (see, e.g., Minta and Man (1997) *J Immunol* 119:1597-1602 and Wetsel and Kolb (1982) *J Immunol* 128:2209-2216) and acid treatment (Yamamoto and Gewurz (1978) *J Immunol* 120:2008 and Damerau et al. (1989) *Molec Immunol* 26:1133-1142) can also cleave C5 and produce active C5b.

Cleavage of C5 releases C5a, a potent anaphylatoxin and chemotactic factor, and leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

The first step in the formation of the terminal complement complex involves the combination of C5b with C6, C7, and C8 to form the C5b-8 complex at the surface of the target cell. Upon the binding of the C5b-8 complex with several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

C5a receptors are found on the surfaces of bronchial and alveolar epithelial cells and bronchial smooth muscle cells. C5a receptors have also been found on eosinophils, mast cells, monocytes, neutrophils, and activated lymphocytes.

While a properly functioning complement system provides a robust defense against infecting microbes, inappropriate regulation or activation of complement has been implicated in the pathogenesis of a variety of disorders including, e.g., rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis. (See, e.g., Holers et al. (2008) *Immunological Reviews* 223:300-316.) Inhibition of complement (e.g., inhibition of: terminal complement formation, C5 cleavage, or complement activation) has been demonstrated to be effective in treating several complement-associated disorders both in animal models and in humans. See, e.g., Rother et al. (2007) *Nature Biotechnology* 25(11):1256-1264; Wang et al. (1996) *Proc Natl Acad Sci USA* 93:8563-8568; Wang et al. (1995) *Proc Natl Acad Sci USA* 92:8955-8959; Rinder et al. (1995) *J Clin Invest* 96:1564-1572; Kroshus et al. (1995) *Transplantation* 60:1194-1202; Homeister et al. (1993) *J Immunol* 150:1055-1064; Weisman et al. (1990) *Science* 249:146-151; Amsterdam et al. (1995) *Am J Physiol* 268: H448-H457; and Rabinovici et al. (1992) *J Immunol* 149: 1744 1750.

SUMMARY

This disclosure relates to stable, highly-concentrated liquid formulations of antibodies as well as methods for making and using the formulations. The disclosure provides, among other things, formulation conditions suitable for maintaining over considerable time the physical and functional stability of an anti-C5 antibody (e.g., eculizumab) in high concentration solutions. For example, the disclosure provides formulation conditions capable of maintaining an anti-C5 antibody in predominantly monomeric form for up to 2 years at 2° C. to 8° C., even when the antibody is maintained in solutions at concentrations of approximately 100 mg/mL. In addition, as described herein and exemplified in the working examples, such formulations also minimize aggregation, fragmentation, or degradation of an anti-C5 antibody within the highly-concentrated solutions. For example, the disclosure provides formulation conditions capable of maintaining for two years an anti-C5 antibody in a highly-concentrated form with no detectable antibody fragmentation or degradation products (as determined using size exclusion chromatography-high performance liquid chromatography (SEC-HPLC)) and no more than 2% aggregate. Also provided herein are conditions suitable for formulating solutions of an anti-C5 antibody such as eculizumab at greater than 200 mg/mL.

The benefits of stable, highly-concentrated aqueous solutions of an anti-C5 antibody are numerous. First, for therapeutic applications which require the antibody to be administered to a patient in a small volume, therapeutic efficacy often turns on the amount of antibody that can be administered in that small volume. In the absence of the ability to formulate an anti-C5 antibody to high concentrations, use of, for example, subcutaneous, intravitreal, and/or intraarticular delivery routes would often be precluded. Relatedly, highly-concentrated antibody formulations allow for more patient choice regarding the route of administration. For therapeutic applications that require frequent and/or chronic administration, self-delivery or -administration is made possible by high concentration formulations and can be more appealing to patients than intravenous infusion. For example, high concentration formulations of an anti-C5 antibody can allow a patient to self-administer the antibody by, e.g., subcutaneous injection. Therefore, the ability to formulate the antibody at high concentrations can increase compliance of administration by providing an easy home administration alternative to patients with complement-associated disorders.

Furthermore, methods for producing the aqueous solutions described herein do not require a lyophilization step, nor do the featured high concentration aqueous solutions need to be reconstituted from lyophilized material. The instantly featured high concentration antibody solutions provide several advantages over reconstituted lyophilized antibody formulations. First, medical practitioners must locally reconstitute lyophilized antibody solutions aseptically, which increases the opportunity for microbial contamination of the solution prior to administration. In addition, reconstitution requires considerable care to be certain that all of the solids contained in the reconstitution vessel are properly dissolved in solution. The high concentration aqueous solutions provided herein thus provide the medical practitioner, caregiver, and/or patient with a fast, easy, safe, and efficient means for delivering a therapeutic antibody to a patient in need thereof.

Other benefits of high concentration formulations include, e.g., manufacturing cost savings from decreasing bulk storage space and/or the number of product fills. In addition, the ability to produce a product having a longer shelf-life will ultimately require fewer production runs, which ultimately reduces cost for the manufacturer and consumer of the highly-concentrated therapeutic antibody.

In one aspect, the disclosure features an aqueous solution comprising an anti-C5 antibody at a concentration of 40 mg/mL to 200 mg/mL. In another aspect, the disclosure features an aqueous solution comprising an anti-C5 antibody at a concentration of greater than 200 mg/mL. Additional exemplary concentrations, including fixed concentrations as well as exemplary ranges of concentrations, are provided herein.

In some embodiments, any of the solutions described herein comprise at least one buffering agent at a concentration of 10 mM to 300 mM, inclusive. In some embodiments, any of the solutions described herein comprise at least one buffering agent at a concentration of 10 mM to 200 mM, inclusive. In some embodiments, the at least one buffering agent is present in the solution at a concentration of at least, or equal to, 20 mM. In some embodiments, the at least one buffering agent is present in the solution at a concentration of at least, or equal to, 50 mM. In some embodiments, the at least one buffering agent is an amino acid. The amino acid can be, e.g., one selected from the group consisting of histidine (e.g., L-histidine), serine (e.g., L-serine), and glycine (e.g., L-glycine). In some embodiments, any of the solutions described herein comprise two or more buffering agents. The two or more buffering agents can be, e.g., histidine and serine. In some embodiments, the two or more buffering agents are histidine and glycine.

In some embodiments, any of the solutions described herein comprise at least one carbohydrate excipient at a concentration of 0.1 to 5%. In some embodiments, the at least one carbohydrate excipient is present in the solution at a concentration of at least, or equal to, 1.5%. In some embodiments, the at least one carbohydrate excipient is present in the solution at a concentration of at least, or equal to, 3%. The at least one carbohydrate excipient can be, e.g., one selected from the group consisting of sorbitol and mannitol. In some embodiments, any of the solutions described herein comprise two or more carbohydrate excipients. At least two of the excipients can be, e.g., sorbitol and mannitol.

In some embodiments, any of the solutions described herein comprise a formulation that comprises, or consists of, the following composition: (i) at least 20 mM histidine; at least 50 mM glycine; at least 3% (w/v) sorbitol; and at least 1.5% (w/v) mannitol; (ii) 20 mM histidine; 50 mM glycine; 3% (w/v) sorbitol; and 1.5% (w/v) mannitol; (iii) at least 20 mM histidine; at least 50 mM serine; at least 3% (w/v) sorbitol; and at least 1.5% (w/v) mannitol; or (iv) at least 20 mM histidine; at least 50 mM serine; at least 2.5% (w/v) sorbitol; and at least 1.5% (w/v) mannitol. Additional exemplary formulations are set forth herein.

In some embodiments, any of the solutions described herein comprise a surfactant. The surfactant can be, e.g., polysorbate 20 or polysorbate 80. The concentration of the surfactant in the solution can be, e.g., between 0.001% to 0.02%, inclusive.

In some embodiments, any of the solutions described herein can have a pH between 6.5 and 7.5.

In some embodiments, any of the solutions described herein are sterile solutions.

In some embodiments of any of the solutions described herein, the anti-C5 antibody is eculizumab.

In some embodiments of any of the solutions described herein, the anti-C5 antibody remains at least 95 (e.g., at least 96, 97, 98, or 99) % monomeric during storage at 2° C. to 8° C. for at least six months as determined by SEC-HPLC. In some embodiments of any of the solutions described herein, the anti-C5 antibody remains at least 95 (e.g., at least 96, 97, 98, or 99) % monomeric during storage at 2° C. to 8° C. for at least one year as determined by SEC-HPLC. In some embodiments of any of the solutions described herein, the anti-C5 antibody remains at least 95 (e.g., at least 96, 97, 98, or 99) % monomeric during storage at 2° C. to 8° C. for at least six months as determined by SEC-HPLC. In some embodiments of any of the solutions described herein, the anti-C5 antibody remains at least 95 (e.g., at least 96, 97, 98, or 99) % monomeric during storage at 2° C. to 8° C. for at least one year as determined by SEC-HPLC. In some embodiments of any of the solutions described herein, the anti-C5 antibody remains at least 95 (e.g., at least 96, 97, 98, or 99) % monomeric during storage at 2° C. to 8° C. for at least 18 months as determined by SEC-HPLC. In some embodiments of any of the solutions described herein, the anti-C5 antibody remains at least 95 (e.g., at least 96, 97, 98, or 99) % monomeric during storage at 2° C. to 8° C. for at least two years as determined by SEC-HPLC.

In some embodiments of any of the solutions described herein, less than 2% of the anti-C5 antibody in the solution is aggregated as determined by SEC-HPLC. In some embodiments of any of the solutions described herein, less than 1% of the anti-C5 antibody in the solution is aggregated as determined by SEC-HPLC.

In some embodiments of any of the solutions described herein, less than 1% of the anti-C5 antibody in the solution is fragmented as determined by SEC-HPLC. In some embodiments of any of the solutions described herein, less than 0.5% of the anti-C5 antibody in the solution is fragmented as determined by SEC-HPLC. In some embodiments of any of the solutions described herein, during storage at 2° C. to 8° C. for at least six months the anti-C5 antibody retains at least 80 (e.g., at least 81, 82, 83, 84, 85, 86, 87, 88, 89, 90, 91, 92, 93, 94, 95, 96, 97, 98, or 99) % of its C5-binding activity, as compared to a reference anti-C5 antibody corresponding to the anti-C5 antibody prior to storage. In some embodiments of any of the solutions described herein, during storage at 2° C. to 8° C. for at least one year the anti-C5 antibody retains at least 80 (e.g., at least 81, 82, 83, 84, 85, 86, 87, 88, 89, 90, 91, 92, 93, 94, 95, 96, 97, 98, or 99) % of its C5-binding activity, as compared to a reference anti-C5 antibody corresponding to the anti-C5 antibody prior to storage. In some embodiments of any of the solutions described herein, during storage at 2° C. to 8° C. for at least 18 months the anti-C5 antibody retains at least 80 (e.g., at least 81, 82, 83, 84, 85, 86, 87, 88, 89, 90, 91, 92, 93, 94, 95, 96, 97, 98, or 99) % of its C5-binding activity, as compared to a reference anti-C5 antibody corresponding to the anti-C5 antibody prior to storage. In some embodiments of any of the solutions described herein, during storage at 2° C. to 8° C. for at least two years the anti-C5 antibody retains at least 80 (e.g., at least 81, 82, 83, 84, 85, 86, 87, 88, 89, 90, 91, 92, 93, 94, 95, 96, 97, 98, or 99) % of its C5-binding activity, as compared to a reference anti-C5 antibody corresponding to the anti-C5 antibody prior to storage. In some embodiments of any of the solutions described herein, during storage at 2° C. to 8° C. for at least six months the anti-C5 antibody retains at least 80 (e.g., at least 81, 82, 83, 84, 85, 86, 87, 88, 89, 90, 91, 92, 93, 94, 95, 96, 97, 98, or 99) % of its ability to inhibit hemolysis, as compared to a reference anti-C5 antibody corresponding to the anti-C5 antibody prior to storage. In some embodiments of any of the solutions described herein, during storage at 2° C. to 8° C. for at least one year the anti-C5 antibody retains at least 80 (e.g., at least 81, 82, 83, 84, 85, 86, 87, 88, 89, 90, 91, 92, 93, 94, 95, 96, 97, 98, or 99) % of its ability to inhibit hemolysis, as compared to a reference anti-C5 antibody corresponding to the anti-C5 antibody prior to storage. In some embodiments of any of the solutions described herein, during storage at 2° C. to 8° C. for at least 18 months the anti-C5 antibody retains at least 80 (e.g., at least 81, 82, 83, 84, 85, 86, 87, 88, 89, 90, 91, 92, 93, 94, 95, 96, 97, 98, or 99) % of its ability to inhibit hemolysis, as compared to a reference anti-C5 antibody corresponding to the anti-C5 antibody prior to storage. In some embodiments of any of the solutions described herein, during storage at 2° C. to 8° C. for at least two years the anti-C5 antibody retains at least 80 (e.g., at least 81, 82, 83, 84, 85, 86, 87, 88, 89, 90, 91, 92, 93, 94, 95, 96, 97, 98, or 99) % of its ability to inhibit hemolysis, as compared to a reference anti-C5 antibody corresponding to the anti-C5 antibody prior to storage.

In another aspect, the disclosure features an aqueous solution comprising an anti-C5 antibody at a concentration of 100±20 (e.g., 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120) mg/mL; 20±5 (e.g., 15, 16, 17, 18, 19, 20, 21, 22, 23, 24, or 25) mM L-histidine; 50±15 (e.g., 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65) mM L-serine; 3±1 (e.g., 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4) % sorbitol; and 1.5±0.5 (e.g., 1, 1.1, 1.2, 1.3, 1.4, 1.5, 1.6, 1.7, 1.8, 1.9, or 2) % mannitol, wherein the solution has a pH of 7.1±0.5 (e.g., 6.6, 6.7, 6.8, 6.9, 7, 7.1, 7.2, 7.3, 7.4, 7.5, or 7.6).

In yet another aspect, the disclosure features a method for producing a concentrated antibody solution comprising greater than (or equal to) 100 mg/mL of an anti-C5 antibody. The method comprises: providing a first aqueous solution comprising an anti-C5 antibody, the first aqueous solution having a first formulation and comprising no more than 50 (e.g., no more than 49, 48, 47, 46, 45, 44, 43, 42, 41, 40, 39, 38, 37, 36, 35, 34, 33, 32, or 31) mg/mL of the anti-C5 antibody; subjecting the first aqueous solution to diafiltration to thereby produce a second aqueous solution, wherein the second aqueous solution has a second formulation as a result of the diafiltration; and concentrating the second aqueous solution to produce a concentrated antibody solution comprising greater than (or equal to) 100 mg/mL of the anti-C5 antibody. In some embodiments, the first aqueous solution comprises greater than 30 mg/mL, but no more than 50 mg/mL, of the anti-C5 antibody. In some embodiments, the first aqueous solution comprises greater than 35 mg/mL, but no more than 50 mg/mL, of the anti-C5 antibody. In some embodiments, the first aqueous solution comprises greater than 35 mg/mL, but no more than 45 mg/mL, of the anti-C5 antibody. In some embodiments, the anti-C5 antibody is not lyophilized prior to or following the diafiltration or concentrating.

In some embodiments of any of the methods, the first formulation is a phosphate buffer-based formulation. The first formulation can comprise, e.g.: at least 20 mM sodium phosphate and at least 80 mM sodium chloride.

In some embodiments of any of the above methods, the second formulation comprises: at least 20 mM histidine; at least 50 mM serine; at least 2.5% (w/v) sorbitol; and at least 1.5% (w/v) mannitol.

In some embodiments of any of the above methods, the concentrating comprises tangential flow filtration and/or use of a stir cell.

In some embodiments of any of the above methods, more than one round of diafiltration is performed. In some embodiments, at least two rounds of diafiltration are performed. In some embodiments, at least four rounds of diafiltration are performed. In some embodiments of any of the above methods, the diafiltration comprises continuous addition of a buffer having the second formulation.

In some embodiments of any of the above methods, the concentrated antibody solution comprises greater than (or equal to) 105 (e.g., greater than, or equal to, 106, 107, 108, 109, 110, 115, 120, 125, 130, 135, 140, 145, 150, 155, 160, 165, 170, 175, 180, 185, 190, 195, 200, 205, or 208) mg/mL of the anti-C5 antibody.

In some embodiments of any of the above methods, at least 80 (e.g., at least 81, 82, 83, 84, 85, 86, 87, 88, 89, 90, 91, 92, 93, 94, 95, 96, 97, 98, or 99) % of the anti-C5 antibody present in the first aqueous solution is recovered in the high concentration aqueous solution. In some embodiments of any of the above methods, at least 90% of the anti-C5 antibody present in the first aqueous solution is recovered in the high concentration aqueous solution.

In some embodiments of any of the above methods, the anti-C5 antibody is eculizumab.

In yet another aspect, the disclosure features an aqueous solution comprising an anti-C5 antibody at a concentration of greater than 100 mg/mL produced by any of the above methods.

In another aspect, the disclosure features a kit comprising: (i) any of the solutions described herein; and (ii) a means for delivering the solution to a patient in need thereof.

In some embodiments of any of the kits described herein, the means is suitable for subcutaneous delivery of the solution to the patient. In some embodiments of any of the kits described herein, the means is suitable for delivery of the solution to the eye. In some embodiments of any of the kits described herein, the means is suitable for intraarticular delivery of the solution to the patient.

In some embodiments of any of the kits described herein, the means is a syringe or a double-barreled syringe. In some embodiments of any of the kits described herein, the means is: (a) a transscleral patch comprising the solution; or (b) a contact lens comprising the solution or partially coated in the solution.

In some embodiments of any of the kits described herein, the means is suitable for intrapulmonary delivery of the solution to the patient. For example, the means can be an inhaler or a nebulizer.

In some embodiments of any of the kits described herein, the solution is formulated for aerosol administration or nebulized administration to the patient.

In some embodiments, any of the kits described herein further comprise at least one additional active agent for use in treating a complement-associated disorder in a subject. Such agents are recited herein.

In yet another aspect, the disclosure features a kit comprising one or more containers, wherein each container comprises an aqueous solution described herein and wherein each container comprises at least one pharmaceutical unit dosage form of the anti-C5 antibody. In some embodiments, each container comprises between 0.05 mg to 10 mg of the anti-C5 antibody. In some embodiments, the kit comprises between about 1 mg and 100 mg of the anti-C5 antibody.

In some embodiments of any of the kits described herein, each container has a volume of 0.01 mL to 1 mL, inclusive. In some embodiments of any of the kits described herein, at least one container comprises an aqueous solution suitable for intravitreal injection to a patient, intraarticular injection to a patient, intramuscular injection to a patient, subcutaneous injection to a patient, and/or intrapulmonary administration to a patient. For example, a kit described herein can comprise at least one container comprising an aqueous solution suitable for use with a nebulizer or inhaler.

In another aspect, the disclosure features a pre-filled syringe comprising any of the aqueous solutions described herein. In some embodiments, the solution is formulated for intraocular, intravitreal, and/or intraarticular administration. In some embodiments, the solution is formulated for intramuscular or subcutaneous administration.

In some embodiments, any of the pre-filled syringes described herein comprise at least one pharmaceutical unit dosage form of the anti-C5 antibody in the solution. Each pharmaceutical unit dosage form can have, e.g., a volume of between 0.02 mL to 0.1 mL, inclusive. In some embodiments, the pharmaceutical unit dosage form has a volume of no more than 0.05 mL.

In some embodiments, any of the pre-filled syringes described herein comprise between 0.05 mg to 10 mg of the anti-C5 antibody. In some embodiments, the syringe comprises between about 1 mg and 100 mg of the anti-C5 antibody.

In yet another aspect, the disclosure features a method for treating a patient afflicted with a complement-associated disorder. The method comprises administering to a patient afflicted with a complement-associated disorder a therapeutically effective amount of any of the aqueous solutions described herein to thereby treat the complement-associated disorder. In some embodiments, the methods can be performed using any of the kits or pre-filled syringes described herein. In some embodiments, the method can further comprise, prior to administering the aqueous solution to the patient, determining that the patient is afflicted with the complement-associated disorder.

In some embodiments, the complement-associated disorder is a complement-associated disorder of the eye. For example, the complement-associated disorder of the eye can be age-related macular degeneration (AMD), a diabetes-associated ocular disorder, or central retinal vein occlusion. In some embodiments, the complement-associated disorder of the eye is wet AMD. In some embodiments, the disorder is dry AMD. In such embodiments, the aqueous solution can be administered to the patient by way of intravitreal injection. In such embodiments, the aqueous solution can be administered to the patient by way of a transscleral patch or as an eye drop (for example, the solution can be formulated for use as an eye drop).

In some embodiments, the complement-associated disorder is rheumatoid arthritis. In such embodiments, e.g., the aqueous solution can be administered to the patient by way of intraarticular injection. In some embodiments, the aqueous solution can be administered by way of intravenous or subcutaneous injection.

In some embodiments, the complement-associated disorder is a pulmonary disorder. The pulmonary disorder can be selected from the group consisting of, e.g., asthma, chronic obstructive pulmonary disease, acute respiratory distress syndrome, pulmonary fibrosis, $\alpha$-1 anti-trypsin deficiency, emphysema, bronchiectasis, bronchiolitis obliterans, sarcoidosis, a collagen vascular disorder, and bronchitis. In such embodiments, the aqueous solution can be delivered to the patient by way of intrapulmonary administration, e.g., through the use of a nebulizer or an inhaler.

In some embodiments, the complement-associated disorder is selected from the group consisting of ischemia-reperfusion injury, atypical hemolytic uremic syndrome, thrombotic thrombocytopenic purpura, paroxysmal nocturnal hemoglobinuria, dense deposit disease, age-related macular degeneration, spontaneous fetal loss, Pauci-immune vasculitis, epidermolysis bullosa, recurrent fetal loss, multiple sclerosis, traumatic brain injury, myasthenia gravis, cold agglutinin disease, dermatomyositis, Degos' disease, Graves' disease, Hashimoto's thyroiditis, type I diabetes, psoriasis, pemphigus, autoimmune hemolytic anemia, idiopathic thrombocytopenic purpura, Goodpasture syndrome, multifocal motor neuropathy, neuromyelitis optica, antiphospholipid syndrome, and catastrophic antiphospholipid syndrome.

In some embodiments, any of the therapeutic methods described herein further comprise administering to the patient one or more additional therapeutic agents for (a) treating a complement-associated disorder or (b) ameliorating one or more symptoms associated with the complement-associated disorder.

In yet another embodiment, the disclosure features an aqueous solution comprising an anti-C5 antibody at a concentration of at least 40 mg/mL. The anti-C5 antibody in the solution remains at least 97% monomeric during storage at 2° C. to 8° C. for at least six months as determined by SEC-HPLC. In some embodiments, the concentration of the anti-C5 antibody in the solution is at least 50 (e.g., at least 55, 60, 65, 70, 75, 80, 85, 90, 95, 100, 110, 120, 130, 140, 150, 160, 170, 180, 190, or 200) mg/mL. In some embodiments, the concentration of the anti-C5 antibody in the solution is greater than 200 mg/mL. The antibody can be, e.g., eculizumab.

In another aspect, the disclosure features an aqueous solution comprising an anti-C5 antibody at a concentration of greater than 40 mg/mL with the proviso that the solution is not formulated as follows: 20 mM histidine, 50 mM glycine, 3% (w/v) sorbitol, 1.5% (w/v) mannitol, 0.001% to 0.02% Tween 80, and a pH of 6 to 8 (e.g., with a physiologic osmolality). In some embodiments, the concentration of the anti-C5 antibody in the solution is at least 50 (e.g., at least 55, 60, 65, 70, 75, 80, 85, 90, 95, 100, 110, 120, 130, 140, 150, 160, 170, 180, 190, or 200) mg/mL. In some embodiments, the concentration of the anti-C5 antibody in the solution is greater than 200 mg/mL. The antibody can be, e.g., eculizumab.

In some embodiments of the aqueous solutions described above, the anti-C5 antibody remains at least 98% monomeric during storage at 2° C. to 8° C. for at least one year (e.g., at least 13, 14, 15, 16, 17, 18, 19, 20, 21, 22, 23, or 24 months) as determined by SEC-HPLC.

In some embodiments of the aqueous solutions described above, less than 2 (e.g., less than 1.9, 1.8, 1.7, 1.6, 1.5, 1.4, 1.3, 1.2, 1.1, 1.0, 0.9, 0.8, 0.7, 0.6, 0.5, 0.4, 0.3, or 0.2) % of the anti-C5 antibody in the solution is aggregated as determined by SEC-HPLC.

In some embodiments of the aqueous solutions described above, less than 0.5 (e.g., less than 0.4, 0.3, 0.2, or 0.1) % of the anti-C5 antibody in the solution is fragmented as determined by SEC-HPLC.

In some embodiments of the aqueous solutions described above, during storage at 2° C. to 8° C. for at least six (e.g., at least seven, eight, nine, 10, 11, 12, 13, 14, 15, 16, 17, 18, 19, 20, 21, 22, 23, or 24) months the anti-C5 antibody retains at least 90 (e.g., at least 91, 92, 93, 94, 95, 96, 97, 98, or 99) % of its C5-binding activity, as compared to a reference anti-C5 antibody corresponding to the anti-C5 antibody prior to storage. Suitable methods for evaluating the binding activity of a sample of a stored solution containing a specified concentration of anti-C5 antibody are known in the art and described herein.

In some embodiments of the aqueous solutions described above, during storage at 2° C. to 8° C. for at least six (e.g., at least seven, eight, nine, 10, 11, 12, 13, 14, 15, 16, 17, 18, 19, 20, 21, 22, 23, or 24) months the anti-C5 antibody retains at least 90 (e.g., at least 91, 92, 93, 94, 95, 96, 97, 98, or 99) % of its ability to inhibit hemolysis, as compared to a reference anti-C5 antibody corresponding to the anti-C5 antibody prior to storage. Suitable methods for evaluating the ability of a sample of a stored solution containing a specified concentration of anti-C5 antibody to inhibit hemolysis are known in the art and described herein.

In some embodiments of the aqueous solutions described above, the solutions can be sterile. In some embodiments of any of the aqueous solutions described above, the solutions can comprise: at least 20 mM histidine; at least 50 mM serine; at least 3% (w/v) sorbitol; and at least 1.5% (w/v) mannitol. In some embodiments of the aqueous solutions described above, the solutions can comprise: at least 20 mM histidine; at least 50 mM serine; at least 2.5% (w/v) sorbitol; and at least 1.5% (w/v) mannitol. In some embodiments of any of the aqueous solutions described above, the solutions can contain: 20 mM histidine; 50 mM serine; 3% (w/v) sorbitol; and 1.5% (w/v) mannitol.

In some embodiments of the aqueous solutions described above, the solution can comprise a surfactant such as, for example, polysorbate 20 or polysorbate 80. The concentration of the surfactant in the solution can be, e.g., between 0.001% to 0.02%, inclusive.

In some embodiments of the aqueous solutions described above, the pH of the solution can be, for example, between 6.5 and 7.5, inclusive.

As used throughout the present disclosure, the term "antibody" refers to a whole antibody (e.g., IgM, IgG, IgA, IgD, or IgE) molecule as well as antigen-binding fragments thereof, which fragments can be generated by any one of a variety of methods that are known in the art and described herein. The term "antibody" includes a polyclonal antibody, a monoclonal antibody, a chimerized or chimeric antibody, a humanized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody. "Antibody fragments," "antigen-binding fragments," or similar terms refer to a fragment of an antibody that retains the ability to bind to an antigen (e.g., human complement component C5 or a biologically active fragment thereof such as C5a or C5b), e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, diabodies (Poljak (1994) *Structure* 2(12):1121-1123; Hudson et al. (1999) *J Immunol Methods* 23(1-2):177-189, the disclosures of both of which are incorporated herein by reference in their entirety), minibodies, single domain or nanobodies (Huang et al. (2010) *Expert Rev Mol Diagn* 10(6):777-785; Smolarek et al. (2010) *Cell Mol Life Sci* 67(19):3371-3387), and intrabodies (Huston et al. (2001) *Hum Antibodies* 10(3-4):127-142; Wheeler et al. (2003) *Mol Ther* 8(3):355-366; Stocks (2004) *Drug Discov Today* 9(22):960-966, the disclosures of each of which are incorporated herein by reference in their entirety) that bind to human C5 protein are embraced by the definition of "antigen-binding fragment" and can be incorporated into the compositions and used in the methods described herein.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating a complement-associated disorder, will be apparent from the following description, the examples, and from the claims.

BRIEF DESCRIPTION OF THE DRAWINGS

FIG. 1 is a flow chart depicting the formulation scheme for preparing five different solutions of eculizumab. A detailed description of the particular composition of solu-

DETAILED DESCRIPTION

The disclosure features stable, aqueous solutions containing a high concentration of an antibody that binds to human complement component C5. The solutions can be used in a variety of therapeutic applications such as methods for treating or preventing complement-associated disorders. While in no way intended to be limiting, exemplary solutions, formulations, therapeutic kits, and methods for making and using any of the foregoing are elaborated on below and are exemplified in the working Examples.

Highly-Concentrated Antibody Solutions

The disclosure provides aqueous solutions comprising a high concentration of an antibody that binds to human complement component C5 [hereinafter an "anti-C5 antibody" or an "anti-human C5 antibody"] such as eculizumab. Such solutions are sometimes referred to herein as "high concentration antibody solutions." As used herein, a "high concentration" of an anti-C5 antibody in an aqueous solution is a concentration of the antibody that is at least, equal to, or greater than, 40 (e.g., at least, equal to, or greater than, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, or 290) mg/mL. In some embodiments, the anti-C5 antibody is present in the solution at a concentration of more than 200 (e.g., more than 200, 205, 210, 215, 220, 225, 230, 235, 240, 245, 250, 255, 260, 265, 270, 275, 280, 285, or 290) mg/mL. In some embodiments, the antibody is present in the solution at a concentration of, e.g., 40 mg/mL to 200 mg/mL, 50 mg/mL to 200 mg/mL, 60 mg/mL to 200 mg/mL, 70 mg/mL to 200 mg/mL, 80 mg/mL to 200 mg/mL, 90 mg/mL to 200 mg/mL, 100 mg/mL to 200 mg/mL, 110 mg/mL to 200 mg/mL, 120 mg/mL to 200 mg/mL, 130 mg/mL to 200 mg/mL, 140 mg/mL to 200 mg/mL, 150 mg/mL to 200 mg/mL, 40 mg/mL to 100 mg/mL, 50 mg/mL to 100 mg/mL, 60 mg/mL to 100 mg/mL, 70 mg/mL to 100 mg/mL, 80 mg/mL to 100 mg/mL, 90 mg/mL to 100 mg/mL, 40 mg/mL to 150 mg/mL, 50 mg/mL to 150 mg/mL, 60 mg/mL to 150 mg/mL, 70 mg/mL to 150 mg/mL, 80 mg/mL to 150 mg/mL, 90 mg/mL to 150 mg/mL, 100 mg/mL to 150 mg/mL, 110 mg/mL to 150 mg/mL, 120 mg/mL to 150 mg/mL, 40 mg/mL to 50 mg/mL, 40 mg/mL to 250 mg/mL, 50 mg/mL to 250 mg/mL, 60 mg/mL to 250 mg/mL, 70 mg/mL to 250 mg/mL, 80 mg/mL to 250 mg/mL, 90 mg/mL to 250 mg/mL, 100 mg/mL to 250 mg/mL, 110 mg/mL to 250 mg/mL, 120 mg/mL to 250 mg/mL, 130 mg/mL to 250 mg/mL, 140 mg/mL to 250 mg/mL, 150 mg/mL to 250 mg/mL, 160 mg/mL to 250 mg/mL, 170 mg/mL to 250 mg/mL, 180 mg/mL to 250 mg/mL, 190 mg/mL to 250 mg/mL, 200 mg/mL to 250 mg/mL, greater than 200 mg/mL (e.g., at least 201 mg/mL) to 250 mg/mL, or greater than 200 mg/mL (e.g., 201 mg/mL or greater) to 300 mg/mL.

In some embodiments, the anti-C5 antibody binds to an epitope in the human pro-C5 precursor protein. For example, the anti-C5 antibody can bind to an epitope in the human complement component C5 protein comprising, or consisting of, the amino acid sequence depicted in SEQ ID NO:1 (NCBI Accession No. AAA51925 and Haviland et al., supra).

An "epitope" refers to the site on a protein (e.g., a human complement component C5 protein) that is bound by an antibody. "Overlapping epitopes" include at least one (e.g., two, three, four, five, or six) common amino acid residue(s).

In some embodiments, the anti-C5 antibody binds to an epitope in the human pro-C5 precursor protein lacking the leader sequence. For example, the anti-C5 antibody can bind to an epitope in the human complement component C5 protein comprising, or consisting of, the amino acid sequence depicted in SEQ ID NO:2, which is a human C5 protein lacking the amino terminal leader sequence.

In some embodiments, the anti-C5 antibody can bind to an epitope in the alpha chain of the human complement component C5 protein. For example, the anti-C5 antibody can bind to an epitope within, or overlapping with, a protein having the amino acid sequence depicted in SEQ ID NO:3, which is the human complement component C5 alpha chain protein. Antibodies that bind to the alpha chain of C5 are described in, for example, Ames et al. (1994) *J Immunol* 152:4572-4581.

In some embodiments, the anti-C5 antibody can bind to an epitope in the beta chain of the human complement component C5 protein. For example, the anti-C5 antibody can bind to an epitope within, or overlapping with, a protein having the amino acid sequence depicted in SEQ ID NO:4, which is the human complement component C5 beta chain protein. Antibodies that bind to the C5 beta chain are described in, e.g., Moongkarndi et al. (1982) *Immunobiol* 162:397; Moongkarndi et al. (1983) *Immunobiol* 165:323; and Mollnes et al. (1988) *Scand J Immunol* 28:307-312.

In some embodiments, the anti-C5 antibody can bind to an epitope within, or overlapping with, an antigenic peptide fragment of a human complement component C5 protein. For example, the anti-C5 antibody can bind to an epitope within, or overlapping with, an antigen peptide fragment of a human complement component C5 protein, the fragment containing, or consisting of, the following amino acid sequence:

```
                                          (SEQ ID NO: 5)
VIDHQGTKSSKCVRQKVEGSS
or
                                          (SEQ ID NO: 6)
KSSKC.
```

In some embodiments, the anti-C5 antibody can bind to an epitope within, or overlapping with, a fragment of a human complement component C5 protein, the fragment containing, or consisting of, any one of the following amino acid sequences (which are exemplary antigenic fragments of SEQ ID NO:1):

```
                                          (SEQ ID NO: 7)
NFSLETWFGKEILVKTLRVVPEGVKRESYSGVTLDPRGIYGTISKRKEF

PYRIPLDLVPKTEIKRILSVKGLLVGEILSAVLSQEGINILTHPKGSAE

AELMSVVPVFYVFHYLETGNHWNIFHSD;

(SEQ ID NO: 8)
SESPVIDHQGTKSSKCVRQKVEGSSSHLVTFTVPLEIGLHGNINFSLET

WFGKEILVKTLRVVPEGVKRESYSGVTLDPRGIYGTISRRKKEFPYRIP

LDLNPKTEIKRILSVKGLLVGEILSAVLSQEGINILTHLPKGSAEAELM

SVVPVFYVFHYLETGNHWNIFHSDPLIEKQKLKKKLKEGMLSIMSYRNA

DYSYS;
```

-continued (SEQ ID NO: 9)
SHKDMQLGRLHMKTLLPVSKPEIRSYFPES;

(SEQ ID NO: 10)
SHKDMQLGRLHMKTLLPVSKPEIRSYFPESWLWEVHLVPRRKQLQFALP

DSLTTWEIQGIGISNTGICVADTVKAKVFKDVFLEMNIPYSVVRGEQIQ

LKGTVYNYRTSGMQFCVKMSAVEGICTSESPVIDHQGTKSSKCVRQKVE

GSSSHLVTFTVLPLEIGLHNINESLETWFGKEILVKTLRVVPEGVKRES

YSGVTLDPRGIYGTISRRKEFPYRIPLDLVPKTEIKRILSVKGLLVGEI

LSAVLSQEGINILTHLPKGSAEAELMSVVPVFYVFHYLETGNHWNIFHS

DPLIEKQKLKKKLKEGMLSIMSYRNADYSYS;
and (SEQ ID NO: 11)
DHQGTKSSKCVRQKVEG.

Additional exemplary antigenic fragments of human complement component C5 are disclosed in, e.g., U.S. Pat. No. 6,355,245, the disclosure of which is incorporated herein by reference.

In some embodiments, the anti-C5 antibody specifically binds to a human complement component C5 protein (e.g., the human C5 protein having the amino acid sequence depicted in SEQ ID NO:1). The terms "specific binding" or "specifically binds" refer to two molecules forming a complex (e.g., a complex between an antibody and a complement component C5 protein) that is relatively stable under physiologic conditions. Typically, binding is considered specific when the association constant ($K_a$) is higher than $10^6$ $M^{-1}$. Thus, an antibody can specifically bind to a C5 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) $M^{-1}$. Examples of antibodies that specifically bind to a human complement component C5 protein are described in, e.g., U.S. Pat. No. http://patft.uspto.gov/netacgi/nph-Parser?Sect1=PTO1&Sect2=HITOFF&d=PALL&p=1&u=%2Fnetahtml%2FPTO%2Fsrchnum.htm&r=1&f=G&l=50&s1=6355245.PN&OS=PN/6355245&RS=PN/6355245-h0↓h0http://patft.uspto.gov/netacgi/nph-Parser?Sect1=PTO1&Sect2=HITOFF&d=PALL&p=1&u=%2Fnetahtml%2FPTO%2Fsrchnum.htm&r=1&f=G&l=50&s1=6355245.PN&OS=PN/6355245&RS=PN/6355245-h2↓h26,355,245, the disclosure of which is incorporated herein by reference in its entirety.

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore™ system; Pharmacia Biosensor AB, Uppsala, Sweden and Piscataway, N.J.), or enzyme-linked immunosorbent assays (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627. See also, U.S. Pat. No. 6,355,245.

In some embodiments, the anti-C5 antibody can cross-block binding of another antibody that binds to an epitope within, or overlapping with, a human complement component C5 protein. In some embodiments, the anti-C5 antibody can crossblock binding of an antibody that binds to an epitope within, or overlapping with, a peptide fragment of a human complement component C5 protein. The peptide fragment can be a fragment of a human complement component C5 protein having the amino acid sequence depicted in any one of SEQ ID NOS:1-11. For example, the peptide fragment can contain, or consist of, the following amino acid sequence:

(SEQ ID No: 5)
VIDHQGTKSSKCVRQKVEGSS.

As used herein, the term "crossblocking antibody" refers to an antibody that lowers the amount of binding of anti-C5 antibody to an epitope on a complement component C5 protein relative to the amount of binding of the anti-C5 antibody to the epitope in the absence of the antibody. Suitable methods for determining whether a first antibody crossblocks binding of a second antibody to an epitope are known in the art. For example, crossblocking antibodies can be identified by comparing the binding of the 5G1.1 anti-C5 monoclonal antibody (produced by the hybridoma cell line ATCC designation HB-11625; see U.S. Pat. No. 6,355,245) in the presence and absence of a test antibody. Decreased binding of the 5G1.1 antibody in the presence of the test antibody as compared to binding of the 5G1.1 antibody in the absence of the test antibody indicates the test antibody is a crossblocking antibody.

Methods for identifying the epitope to which a particular antibody (e.g., an anti-C5 antibody) binds are also known in the art. For example, the binding epitope of an anti-C5 antibody can be identified by measuring the binding of the antibody to several (e.g., three, four, five, six, seven, eight, nine, 10, 15, 20, or 30 or more) overlapping peptide fragments of a complement component C5 protein (e.g., several overlapping fragments of a protein having the amino acid sequence depicted in any one of SEQ ID NOs:1-11). Each of the different overlapping peptides is then bound to a unique address on a solid support, e.g., separate wells of a multi-well assay plate. Next, the anti-C5 antibody is interrogated by contacting it to each of the peptides in the assay plate for an amount of time and under conditions that allow for the antibody to bind to its epitope. Unbound anti-C5 antibody is removed by washing each of the wells. Next, a detectably-labeled secondary antibody that binds to the anti-C5 antibody, if present in a well of the plate, is contacted to each of the wells, and unbound secondary antibody is removed by washing steps. The presence or amount of the detectable signal produced by the detectably-labeled secondary antibody in a well is an indication that the anti-C5 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore™ chromatographic techniques (see, e.g., Pharmacia BIAtechnology Handbook, "Epitope Mapping," Section 6.3.2, (May 1994); and Johne et al. (1993) *J Immunol Methods* 160:191-8).

The anti-C5 antibodies described herein can have activity in blocking the generation or activity of the C5a and/or C5b active fragments of a complement component C5 protein (e.g., a human C5 protein). Through this blocking effect, the anti-C5 antibodies inhibit, e.g., the proinflammatory effects of C5a and the generation of the C5b-9 membrane attack complex (MAC) at the surface of a cell. Anti-C5 antibodies that have the ability to block the generation of C5a are described in, e.g., Moongkarndi et al. (1982) *Immunobiol* 162:397 and Moongkarndi et al. (1983) *Immunobiol* 165:323.

Inhibition of complement component C5 can also reduce the cell-lysing ability of complement in a subject's body fluids. Such reductions of the cell-lysing ability of complement present can be measured by methods well known in the art such as, for example, by a conventional hemolytic assay such as the hemolysis assay described by Kabat and Mayer (eds), "Experimental Immunochemistry, 2$^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

In some embodiments, an anti-C5 antibody, or antigen-binding fragment thereof, can reduce the ability of a C5 protein to bind to human complement component C3b (e.g., C3b present in an AP or CP C5 convertase complex) by greater than 50 (e.g., greater than 55, 60, 65, 70, 75, 80, 85, 90, or 95 or more) %. In some embodiments, upon binding to a C5 protein, the anti-C5 antibody or antigen-binding fragment thereof can reduce the ability of the C5 protein to bind to complement component C4b (e.g., C4b present in a CP C5 convertase) by greater than 50 (e.g., greater than 55, 60, 65, 70, 75, 80, 85, 90, or 95 or more) %. Methods for determining whether an antibody can block the generation or activity of the C5a and/or C5b active fragments of a complement component C5 protein, or binding to complement component C4b or C3b, are known in the art and described in, e.g., U.S. Pat. No. http://patft.uspto.gov/netacgi/nph-Parser?Sect1=PTO1&Sect2=HITOFF&d=PALL&p=1&u=%2Fnetahtml%2FPTO%2Fsrc
hnum.htm&r=1&f=G&l=50&s1=6355245.PN&OS=PN/6355245&RS=PN/6355245-h0;h0http://patft.uspto.gov/netacgi/nph-Parser?Sect1=PTO1&Sect2=HITOFF&d=PALL&p=1&u=%2Fnetahtml%2FPTO%2Fsrc
hnum.htm&r=1&f=G&l=50&s1=6355245.PN&OS=PN/6355245&RS=PN/6355245-h2;h6,355,245 and Wurzner et al. (1991) *Complement Inflamm* 8:328-340. (See also below.)

In some embodiments, an anti-C5 antibody binds to an amino-terminal region of the alpha chain of a complement component C5 protein, but does not bind to free C5a. Epitopes for an anti-C5 antibody within the amino-terminal region of the alpha chain include, e.g., epitopes within the human sequence VIDHQGTKSSKCVRQKVEGSS (SEQ ID NO:5).

In some embodiments, the composition comprises, and/or the antibody is, eculizumab (Soliris®; Alexion Pharmaceuticals, Inc., Cheshire, Conn.) or a biologically-active fragment thereof. (See, e.g., Kaplan (2002) *Curr Opin Investig Drugs* 3(7):1017-23; Hill (2005) *Clin Adv Hematol Oncol* 3(11):849-50; and Rother et al. (2007) *Nature Biotechnology* 25(11):1256-1488.) The amino acid sequence of the light chain of eculizumab is as follows:

(SEQ ID NO: 12)
DIQMTQSPSSLSASVGDRVTITCGASENIYGALNWYQQKPGKAPKLLIY

GATNLADGVPSRFSGSGSGTDFTLTISSLQPEDFATYYCQNVLNTPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

The amino acid sequence of the heavy chain of eculizumab is as follows:

(SEQ ID NO: 13)
QVQLVQSGAEVKKPGASVKVSGKASGYIFSNYWIQWVRQAPGQGLEWMGE

ILPGSGSTEYTENFKDRVTMTRDTSTSTVYMELSSLRSEDTAVYYCARYF

FGSSPNWYFDVWGQGTLVTVSSASTKGPSVFPLAPCSRSTSESTAALGCL

VKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKD

TLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK.

As described herein and exemplified in the working examples, the featured aqueous solutions provide the anti-C5 antibody formulated therein with marked stability—both physical/chemical stability as well as functional stability. For example, the formulations described herein are capable of maintaining the structural integrity of an anti-C5 antibody present at high concentrations in a solution. That is, an anti-C5 antibody in a featured aqueous buffer can remain predominantly monomeric after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at approximately 2° C. to 8° C. (e.g., storage at, e.g., 1, 2, 3, 4, 5, 6, 7, 8, 9, or 10° C.). As exemplified in the working examples described herein, the inventors provide formulations suitable for maintaining an anti-C5 antibody at approximately 30 mg/mL or approximately 100 mg/mL in predominantly monomeric form for up to two years at approximately 2° C. to 8° C. As used herein, an anti-C5 antibody formulated at a high concentration in a featured aqueous solution is "predominantly monomeric," or in "predominantly monomeric form," if the antibody present in the solution is at least 95 (e.g., at least 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, or 99.9 or greater) % monomeric, e.g., as determined using size exclusion chromatography high performance liquid chromatography (SEC-HPLC). That is: less than 5 (e.g., less than 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody in the solution is oligomeric, aggregated, and/or fragmented. As used herein, antibody fragmentation refers to improperly assembled constituents or degradation products of a whole antibody having a lower molecular weight than the whole antibody. Such fragmentation forms include, but are not limited to, a free monomeric heavy chain polypeptide, a dimeric heavy chain polypeptide (e.g., disulfide-linked heavy chain polypeptide), a dimeric heavy chain polypeptide bound to one light chain polypeptide, a monomeric heavy chain polypeptide bound to one light chain polypeptide, or further degradation product(s) or fragment(s) of a light chain or heavy chain polypeptide. In some embodiments, less than 2 (e.g., less than 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody is aggregated after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. In some embodiments, less than 1 (e.g., less than 0.9, 0.8, 0.7, 0.6, 0.5, 0.4, 0.3, 0.2, or 0.1) % of the antibody is fragmented after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. Methods for determining the amount of monomeric antibody, as well as the amount of oligomeric, aggregated, or fragmented forms of the anti-C5 antibody present in solution are described herein and exemplified in the working examples. For example, a skilled artisan can determine the percentage of whole, fragmented, unfolded intermediates, and/or aggregated antibody species present in a given solution using, e.g., size exclusion chromatography high-performance liquid chromatography (SEC-HPLC), static light scattering (SLS), Fourier transform infrared spectroscopy (FTIR), circular dichroism (CD), urea-induced protein unfolding techniques, intrinsic tryptophan fluorescence, non-reducing sodium dodecyl sulfate polyacrylamide gel electrophoresis (SDS-PAGE), and differential scanning calorimetry (DSC). In the working examples described herein, the inventors exemplify the use of, among others, SEC-HPLC and SDS-PAGE to determine the physical state of the anti-C5 antibodies in solution.

In some embodiments, the formulation conditions described herein are capable of maintaining the anti-C5 antibody in at least 95 (e.g., at least 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, or 99.9 or greater) % monomeric form when stored for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at approximately −20° C. (e.g., −20±5° C.). The percentage of monomeric form of the antibody in solution can be determined using SEC-HPLC. That is: less than 5 (e.g., less than 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody in the solution can become oligomeric, aggregated, and/or fragmented, when the aqueous solution is stored for at least one month at −20° C. As described above, in some embodiments, less than 2 (e.g., less than 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1) % of the antibody is aggregated after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at approximately −20° C. In some embodiments, less than 1 (e.g., less than 0.9, 0.8, 0.7, 0.6, 0.5, 0.4, 0.3, 0.2, or 0.1) % of the antibody is fragmented after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at −20° C.

As described herein and exemplified in the working examples, the anti-C5 antibody containing solutions featured herein can retain at least 90 (e.g., 91, 92, 93, 94, 95, 96, 97, 98, 99, or even 100) % of their biological/functional activity (e.g., ability to bind to human C5) after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. Antibody present in a featured solution can retain, in some embodiments, at least 90 (e.g., 91, 92, 93, 94, 95, 96, 97, 98, 99, or even 100) % of its activity to inhibit hemolysis after storage for at least one month (e.g., at least two months, three months, four months, five months, six months, seven months, eight months, nine months, 10 months, 11 months, 12 months, 13 months, 14 months, 15 months, 16 months, 17 months, 18 months, 19 months, 20 months, 21 months, 22 months, 23 months, 24 months, or more) at 2° C. to 8° C. Suitable hemolytic assay methods for determining whether an antibody in a featured solution retains its activity are described herein and known in the art, e.g., in vitro hemolytic assays using avian or porcine erythrocytes. Suitable methods for evaluating the ability of an antibody preparation to bind to human complement component C5 are known in the art and described herein.

In some embodiments, any of the aqueous solutions described herein can contain one or more common excipients and/or additives such as buffering agents, sugars or saccharides, salts, and surfactants. Additionally or alternatively, the solutions can further contain one or more solubilizers, diluents, binders, stabilizers, salts, lipophilic solvents, amino acids, chelators, or preservatives.

The solutions described herein can also include a buffering or pH-adjusting agent. In some embodiments, any of the aqueous solutions described herein can have, or can be adjusted to have, a neutral pH. As used herein, "neutral pH" is a pH that is between, and inclusive of, 7 and 8. Accordingly, as used herein neutral pH is inclusive of particular pH values such as 7, 7.1, 7.2, 7.3, 7.4, 7.5, 7.6, 7.7, 7.8, 7.9, and 8.0. In some embodiments, neutral pH is at least pH 7 (e.g., at least pH 7.1, 7.2, 7.3, 7.4, 7.5, 7.6, 7.7, 7.7 or 7.9), but less than pH 8 (e.g., less than pH 7.9, 7.8, 7.7, 7.6, 7.5, 7.4, 7.3, 7.2, or 7.1). That is, in some embodiments neutral pH can be, e.g., at least pH 7, but less than pH 7.5. In some embodiments, neutral pH can be between pH 7 and pH 7.5. In some embodiments, neutral pH can be between pH 7 and pH 7.2.

In some embodiments, neutral pH can be, e.g., pH 7. One of skill in the art will also appreciate that human blood (such as human blood from a healthy patient) has a neutral pH as defined herein, e.g., the pH of human blood is approximately pH 7.35 to pH 7.45. See, e.g., Boron and Boulpaep (2003) "Medical physiology: a cellular and molecular approach," W.B. Saunders, New York (ISBN:0721632564). In some embodiments, the pH of a highly-concentrated antibody solution described herein is between approximately 6.4 and 7.5, inclusive (e.g., approximately 6.2, 6.3, 6.4, 6.5, 6.6, 6.7, 6.8, 6.9, 7, 7.1, 7.2, 7.3, 7.4, 7.5, 7.6, or 7.7).

Buffering agents useful in the aqueous solutions described herein include, e.g., salts of citric acid, ascorbic acid, gluconic acid, carbonic acid, tartaric acid, succinic acid, acetic acid, or phthalic acid. In some embodiments, the buffer is a Tris-based or phosphate buffer.

In some embodiments, the aqueous solutions described herein can include one or more amino acids, which can, among other things, provide buffering capacity. Suitable amino acids for use in the solutions featured herein include, e.g., histidine, glycine, and serine. In some embodiments, the featured solutions do not include a free amino acid as a buffering agent. In some embodiments, the featured solutions include but one free amino acid (e.g., histidine) as a buffering agent. In some embodiments, the featured solutions can include two or more (e.g., two, three, four, five, six, or seven or more) different amino acids as buffering agents, e.g., serine and histidine.

The buffering agents are generally used at concentrations between approximately 1 mM and 200 mM, depending, in part, on the buffering capacity required. In some embodiments, an aqueous solution described herein can include a buffering agent at a concentration of less than, or approximately, 300 (e.g., less than, or approximately, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10) mM. In some embodiments, an aqueous solution described herein contains a buffering agent at a concentration of at least 10 (e.g., at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, or 300 or more) mM. In some embodiments, an aqueous solution described herein can include a buffering agent at a concentration of between about 10 mM to 50 mM, 15 mM to 50 mM, 20 mM to 50 mM, 25 mM to 50 mM, 30 mM to 50 mM, 40 mM to 50 mM, 10 mM to 100 mM, 15 mM to 100 mM, 20 mM to 100 mM, 25 mM to 100 mM, 30 mM to 100 mM, 40 mM to 100 mM, 10 mM to 150 mM, 15 mM to 150 mM, 20 mM to 150 mM, 25 mM to 150 mM, 30 mM to 150 mM, 40 mM to 150 mM, 50 mM to 100 mM, 60 mM to 100 mM, 70 mM to 100 mM, 80 mM to 100 mM, 50 mM to 150 mM, 60 mM to 150 mM, 70 mM to 150 mM, 80 mM to 150 mM, 90 mM to 150 mM, 100 mM to 150 mM, 10 mM to 200 mM, 15 mM to 200 mM, 20 mM to 200 mM, 25 mM to 200 mM, 30 mM to 200 mM, 40 mM to 200 mM, 50 mM to 200 mM, 60 mM to 200 mM, 70 mM to 200 mM, 80 mM to 200 mM, 90 mM to 200 mM, 100 mM to 200 mM, 150 mM to 200 mM, 10 mM to 250 mM, 15 mM to 250 mM, 20 mM to 250 mM, 25 mM to 250 mM, 30 mM to 250 mM, 40 mM to 250 mM, 50 mM to 250 mM, 60 mM to 250 mM, 70 mM to 250 mM, 80 mM to 250 mM, 90 mM to 250 mM, 100 mM to 250 mM, 150 mM to 250 mM, or 200 mM to 250 mM. It is understood that in embodiments where a featured solution contains two or more (e.g., at least two, three, four, five, six, seven, eight, nine, or 10 or more) different buffering agents, each of the two or more buffering agents can independently be present at, e.g., one of the above described concentrations.

In some embodiments, any of the aqueous solutions described herein can contain a salt, e.g., sodium chloride, potassium chloride, or magnesium chloride. In some embodiments, an aqueous solution described herein contains a salt at a concentration of at least 10 (e.g., at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, or 300 or more) mM. In some embodiments, an aqueous solution described herein can include a salt at a concentration of less than, or approximately, 200 (e.g., less than, or approximately, 190, 180, 170, 160, 150, 140, 130, 120, 110, 100, 90, 80, 70, 60, 50, 40, 30, 25, 20, 15, or 10) mM. In some embodiments, an aqueous solution described herein can include a salt at a concentration of between about 10 mM to 50 mM, 15 mM to 50 mM, 20 mM to 50 mM, 25 mM to 50 mM, 30 mM to 50 mM, 40 mM to 50 mM, 10 mM to 100 mM, 15 mM to 100 mM, 20 mM to 100 mM, 25 mM to 100 mM, 30 mM to 100 mM, 40 mM to 100 mM, 10 mM to 150 mM, 15 mM to 150 mM, 20 mM to 150 mM, 25 mM to 150 mM, 30 mM to 150 mM, 40 mM to 150 mM, 50 mM to 100 mM, 60 mM to 100 mM, 70 mM to 100 mM, 80 mM to 100 mM, 50 mM to 150 mM, 60 mM to 150 mM, 70 mM to 150 mM, 80 mM to 150 mM, 90 mM to 150 mM, 100 mM to 150 mM, 10 mM to 200 mM, 15 mM to 200 mM, 20 mM to 200 mM, 25 mM to 200 mM, 30 mM to 200 mM, 40 mM to 200 mM, 50 mM to 200 mM, 60 mM to 200 mM, 70 mM to 200 mM, 80 mM to 200 mM, 90 mM to 200 mM, 100 mM to 200 mM, 150 mM to 200 mM, 10 mM to 250 mM, 15 mM to 250 mM, 20 mM to 250 mM, 25 mM to 250 mM, 30 mM to 250 mM, 40 mM to 250 mM, 50 mM to 250 mM, 60 mM to 250 mM, 70 mM to 250 mM, 80 mM to 250 mM, 90 mM to 250 mM, 100 mM to 250 mM, 150 mM to 250 mM, or 200 mM to 250 mM. It is understood that in embodiments where a featured solution contains two or more (e.g., at least two, three, four, five, six, seven, eight, nine, or 10 or more) different salts, each of the two or more salts can independently be present at, e.g., one of the above described concentrations.

In some embodiments, any of the aqueous solutions described herein can contain a carbohydrate excipient. Suitable carbohydrate excipients are described in, e.g., Katakam and Banga (1995) *J Pharm Pharmacol* 47(2):103-107; Andya et al. (2003) *AAPS Pharm Sci* 5(2: Article 10; and Shire (2009) "Current Trends in Monoclonal Antibody Development and Manufacturing," Volume 11, Springer, 354 pages. Carbohydrate excipients suitable for use in the solutions described herein include, without limitation, monosaccharides such as fructose, maltose, galactose, glucose, D-mannose, and sorbose; disaccharides such as lactose, sucrose, trehalose, and cellobiose; polysaccharides such as maltodextrins, dextrans, and starches; and sugar alcohols such as mannitol, xylitol, maltitol, lactitol, and sorbitol. In some embodiments, a carbohydrate excipient is present in a solution featured herein at a concentration of at least, or approximately, 0.5 (e.g., at least, or approximately, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.25, 3.5, 3.75, 4, 4.25, 4.5, 4.75, 5, 5.5, 6, 6.5, 7, 7.5, 8, 8.5, 9, 9.5, 10, or more) %. In embodiments where a featured solution contains two or more (e.g., at least two, three, four, five, six, seven, eight, nine, or 10 or more) different carbohydrate excipients (e.g., sorbitol and mannitol), each excipient can, independently, be present at any of the above-described concentrations.

In some embodiments, an aqueous solution described herein can contain a surfactant such as an anionic, cationic, or nonionic surfactant. Pharmaceutically-acceptable surfactants include, without limitation: polysorbates: Triton™ (e.g., Triton™ 20 or Triton™ 80), sodium octyl glycoside; lauryl-, myristyl-, linoleyl-, or stearylsulfobetaine; lauryl-, myristyl-, linoleyl- or stearyl-sarcosine; linoleyl-, myristyl-, or cetylbetaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and polyethyl glycol, polypropyl glycol, and copolymers of ethylene and propylene glycol. In some embodiments, the aqueous solutions described herein contain a surfactant (e.g., any of the pharmaceutically-acceptable surfactants described herein or known in the art) at a concentration of at least, or approximately, 0.001 (e.g., at least, or approximately, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 or more) %. In some embodiments, an aqueous solution described herein contains no more than 0.2 (e.g., no more than 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001) % of a pharmaceutically-acceptable surfactant.

In some embodiments, an aqueous solution described herein can be formulated to comprise the following elements: 20 mM histidine, 50 mM serine, 3% sorbitol, and 1.5% mannitol. In some embodiments, this solution is formulated at pH 7. In some embodiments, the aqueous solution can consist of the foregoing elements along with an anti-C5 antibody (e.g., any one of the anti-C5 antibodies described herein) at any of the high concentrations described herein.

In some embodiments, an aqueous solution described herein can comprise, or consist of: (i) an anti-C5 antibody (e.g., eculizumab) at a concentration of at least, or approximately, 80 (e.g., at least, or approximately, 85, 90, 95, 100, 105, 110, 115, 120, 125, 130, 135, 140, 145, 150, 155, 160, 165, 170, 175, 180, 185, 190, 195, 200, 210, 220, 230, 240, or 250 or more) mg/mL; (ii) at least, or approximately, 10 (e.g., at least, or approximately, 15 or 20 or more) mM histidine; (ii) at least, or approximately, 10 (e.g., at least, or approximately, 15, 20, 25, 30, 35, 40, 45, or 50 or more) mM serine; (iv) at least, or approximately, 1 (e.g., at least, or approximately, 1.5, 2, 2.5, or 3 or more) % sorbitol; and (v) at least 0.5 (e.g., at least, or approximately, 0.75, 1, 1.25, or 1.5 or more) % mannitol, wherein the solution is formulated at neutral pH (e.g., a pH of approximately 7).

In some embodiments, an aqueous solution described herein can comprise, or consist of: (i) eculizumab at a concentration of at least, or approximately 100 mg/mL; (ii) at least, or approximately, 20 mM histidine; (ii) at least, or approximately, 50 mM serine; (iv) at least, or approximately, 3% sorbitol; and (v) at least, or approximately, 1.5% mannitol, wherein the solution is formulated at a pH of approximately 7.

In some embodiments, an aqueous solution described herein can be formulated to comprise the following elements: 10 mM histidine HCl, 10% alpha-trehalose dihydrate, and 0.01% polysorbate 20. In some embodiments, this solution is formulated at pH 7. In some embodiments, the aqueous solution can consist of the foregoing elements along with an anti-C5 antibody (e.g., any one of the anti-C5 antibodies described herein) at any of the high concentrations described herein.

In some embodiments, the aqueous solutions described herein do not contain the following elements at the recited concentrations and pH: 20 mM histidine; 50 nM glycine; 3% (w/v) sorbitol; 1.5% (w/v) mannitol; 0.001% to 0.02% Tween 80; and a pH of 6 to 8. In some embodiments, an aqueous solution described herein does not contain trehalose (e.g., alpha-trehalose). In some embodiments, an aqueous solution described herein is not a phosphate-based buffer (e.g., phosphate buffered saline). For example, in some embodiments, the solution does not contain sodium phosphate. In some embodiments, the aqueous solutions described herein do not contain the following elements at the recited concentrations: 10 mM sodium phosphate, 150 mM sodium chloride, 0.001% to 0.02% Tween 80, and at a pH of 6 to 8.

In some embodiments, any of the aqueous solutions described herein are isotonic with respect to human blood. In some embodiments, a solution described herein has an osmotic pressure of between approximately 270 mOsm/kg and 328 mOsm/kg, e.g., approximately, 270 mOsm/kg, 275 mOsm/kg, 280 mOsm/kg, 285 mOsm/kg, 290 mOsm/kg, 295 mOsm/kg, 300 mOsm/kg, 305 mOsm/kg, 310 mOsm/kg, 315 mOsm/kg, 320 mOsm/kg, 325 mOsm/kg, or 328 mOsm/kg. In some embodiments, a solution described herein has an osmotic pressure that is at least or greater than 250 (e.g., at least, or greater than, 255, 260, 265, 270, 275, 280, 285, 290, 295, 300, 305, 310, 315, 320, 325, or 327) mOsm/kg, but not more than, or less than, 350 (e.g., not more than, or less than, 345, 340, 335, 327, 325, 320, 315, 310, 305, or 300) mOsm/kg. In some embodiments, the solutions described herein can contain, or be formulated with, one or more tonicity agents useful for maintaining or modulating the osmotic pressure of a solution. For example, a solution described herein can contain one or more amino acids, certain pharmaceutically-acceptable salts, or sugars.

The aqueous solutions described herein can be sterile, pharmaceutical-grade compositions, e.g., for administration to a subject for the treatment or prevention of a complement-associated disorder. The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). Suitable formulation methods for the high concentration antibody solutions described herein are exemplified in the working examples.

In some embodiments, a high concentration antibody solution described herein can be formulated for delivery to the eye. As used herein, the term "eye" refers to any and all anatomical tissues and structures associated with an eye. In some embodiments, an aqueous solution described herein can be administered locally, for example, by way of topical application or intravitreal injection. For example, in some embodiments, solution can be formulated for administration by way of an eye dropper.

In some embodiments, a sterile, aqueous solution contains, e.g., additional ingredients such as, but not limited to, preservatives, buffers, tonicity agents, antioxidants and stabilizers, nonionic wetting or clarifying agents, and viscosity-increasing agents. Suitable preservatives for use in such a solution include benzalkonium chloride, benzethonium chloride, chlorobutanol, thimerosal and the like. Suitable buffers include, e.g., boric acid, sodium and potassium bicarbonate, sodium and potassium borates, sodium and potassium carbonate, sodium acetate, and sodium biphosphate, in amounts sufficient to maintain the pH at between about pH 6 and pH 8 (see above for suitable pH ranges). Suitable tonicity agents are dextran 40, dextran 70, dextrose, glycerin, potassium chloride, propylene glycol, and sodium chloride.

Suitable antioxidants and stabilizers include sodium bisulfite, sodium metabisulfite, sodium thiosulfite, and thiourea. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, and carboxymethylcellulose.

In some embodiments, a highly-concentrated antibody solution described herein can be formulated for administration to the eye, e.g., topical administration to the eye of the subject in need of treatment (e.g., a subject afflicted with AMD). For example, in some embodiments, a highly-concentrated antibody solution described herein can be formulated as an eye drop. In addition, a highly-concentrated antibody solution described herein can be formulated for use with any of a variety of devices developed for introducing therapeutic compounds into the vitreous cavity of the eye. For example, U.S. patent application publication no. 20020026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. Additional methods and devices (e.g., a transscleral patch and delivery via contact lenses) for delivery of a therapeutic agent to the eye are described in, e.g., Ambati and Adamis (2002) *Prog Retin Eye Res* 21(2):145-151; Ranta and Urtti (2006) *Adv Drug Delivery Rev* 58(11):1164-1181; Barocas and Balachandran (2008) *Expert Opin Drug Delivery*, 5(1): 1-10(10); Gulsen and Chauhan (2004) *Invest Ophthalmol Vis Sci* 45:2342-2347; Kim et al. (2007) *Ophthalmic Res* 39:244-254; and PCT publication no. WO 04/073551, the disclosures of which are incorporated herein by reference in their entirety.

In some embodiments, an antibody or antigen-binding fragment described herein can be formulated in a composition suitable for intrapulmonary administration (e.g., for administration via nebulization; see below) to a mammal such as a human. Methods for preparing such compositions are well known in the art and described in, e.g., U.S. patent application publication no. 20080202513; U.S. Pat. Nos. 7,112,341 and 6,019,968; and PCT application publication nos. WO 00/061178 and WO 06/122257, the disclosures of each of which are incorporated herein by reference in their entirety. Dry powder inhaler formulations and suitable systems for administration of the formulations are described in, e.g., U.S. patent application publication no. 20070235029, PCT Publication No. WO 00/69887; and U.S. Pat. No. 5,997,848.

Pulmonary drug delivery may be achieved by inhalation, and administration by inhalation herein may be oral and/or nasal. Examples of pharmaceutical devices for pulmonary delivery include metered dose inhalers and nebulizers. For example, an antibody or antigen-binding fragment thereof can be administered to the lungs of a subject by way of a nebulizer. Nebulizers use compressed air to deliver a compound as a liquefied aerosol or mist. A nebulizer can be, e.g., a jet nebulizer (e.g., air or liquid-jet nebulizers) or an ultrasonic nebulizer. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, the solutions provided herein are present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering the solution to a subject with as little pain as possible.

One medication delivery pen includes a vial holder into which a vial of insulin or other medication may be received. The vial holder is an elongate generally tubular structure with proximal and distal ends. The distal end of the vial holder includes mounting means for engaging a double-ended needle cannula. The proximal end also includes mounting means for engaging a pen body which includes a driver and dose setting apparatus. A disposable medication (e.g., a high concentration solution of an anti-C5 antibody) containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the stopper of the vial distally for a distance corresponding to the selected dose. The user of the pen mounts a double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above. Accordingly, a medication delivery pen generally has a drive mechanism for accurate dosing and ease of use.

A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. See U.S. Pat. No. 6,192,891.

In some embodiments, the needle of the pen device is disposable and the kits include one or more disposable replacement needles. Pen devices suitable for delivery of the any one of the presently featured antibody solutions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, Molly™, manufactured by Scandinavian Health Ltd.

The present disclosure also presents controlled-release or extended-release formulations suitable for chronic and/or self-administration of a medication. The various formulations can be administered to a patient in need of treatment with the medication as a bolus or by continuous infusion over a period of time.

In some embodiments, a high concentration anti-C5 antibody solution described herein is formulated for sustained-release, extended-release, timed-release, controlled-release, or continuous-release administration. In some embodiments, depot formulations are used to administer the antibody to the subject in need thereof. In this method, the antibody is formulated with one or more carriers providing a gradual release of active agent over a period of a number of hours or days. Such formulations are often based upon a degrading matrix which gradually disperses in the body to release the active agent.

In some embodiments, a highly-concentrated antibody solution described herein can be formulated with one or more additional active agents useful for treating or preventing a complement-associated disorder (e.g., an AP-associated disorder or a CP-associated disorder) in a subject. Additional agents for treating a complement-associated disorder in a subject will vary depending on the particular disorder being treated, but can include, without limitation, an antihypertensive (e.g., an angiotensin-converting enzyme inhibitor) [for use in treating, e.g., HELLP syndrome], an anticoagulant, a corticosteroid (e.g., prednisone), or an immunosuppressive agent (e.g., vincristine or cyclosporine A). Examples of anticoagulants include, e.g., warfarin (Coumadin), aspirin, heparin, phenindione, fondaparinux, idraparinux, and thrombin inhibitors (e.g., argatroban, lepirudin, bivalirudin, or dabigatran). An anti-C5 antibody described herein can also be formulated with a fibrinolytic agent (e.g., ancrod, $\epsilon$-aminocaproic acid, antiplasmin-$a_1$, prostacyclin, and defibrotide) for the treatment of a complement-associated disorder. In some embodiments, an anti-C5 antibody can be formulated with a lipid-lowering agent such as an inhibitor of hydroxymethylglutaryl CoA reductase. In some embodiments, an anti-C5 antibody can be formulated with, or for use with, an anti-CD20 agent such as rituximab (Rituxan™; Biogen Idec, Cambridge, Mass.). In some embodiments, e.g., for the treatment of RA, an anti-C5 antibody can be formulated with one or both of infliximab (Remicade®; Centocor, Inc.) and methotrexate (Rheumatrex®, Trexall®). In some embodiments, an anti-C5 antibody described herein can be formulated with a non-steroidal anti-inflammatory drug (NSAID). Many different NSAIDS are available, some over the counter including ibuprofen (Advil®, Motrin®, Nuprin®) and naproxen (Aleve®) and many others are available by prescription including meloxicam (Mobic®), etodolac (Lodine®), nabumetone (Relafen®), sulindac (Clinoril®), tolementin (Tolectin®), choline magnesium salicylate (Trilisate®), diclofenac (Cataflam®, Voltaren®, Arthrotec®), Diflunisal (Dolobid®), indomethacin (Indocin®), ketoprofen (Orudis®, Oruvail®), oxaprozin (Daypro®), and piroxicam (Feldene®). In some embodiments a C5-binding polypeptide can be formulated for use with an anti-hypertensive, an anti-seizure agent (e.g., magnesium sulfate), or an anti-thrombotic agent. Anti-hypertensives include, e.g., labetalol, hydralazine, nifedipine, calcium channel antagonists, nitroglycerin, or sodium nitroprusside. (See, e.g., Mihu et al. (2007) *J Gastrointestin Liver Dis* 16(4):419-424.) Anti-thrombotic agents include, e.g., heparin, antithrombin, prostacyclin, or low dose aspirin.

In some embodiments, a highly-concentrated antibody solution described herein can be formulated for administration with one or more additional therapeutic agents for use in treating a complement-associated disorder of the eye. Such additional therapeutic agents can be, e.g., bevacizumab or the Fab fragment of bevacizumab or ranibizumab, both sold by Roche Pharmaceuticals, Inc., and pegaptanib sodium (Mucogen®; Pfizer, Inc.). Such a kit can also, optionally, include instructions for administering the anti-C5 antibody to a subject.

In some embodiments, a highly-concentrated antibody solution described herein can be formulated with one or more additional therapeutic agents for use in treating a complement-associated pulmonary disorder such as, but not limited to, asthma, chronic obstructive pulmonary disease, acute respiratory distress syndrome, pulmonary fibrosis, $\alpha$-1 anti-trypsin deficiency, emphysema, bronchiectasis, bronchiolitis obliterans, sarcoidosis, a collagen vascular disorder, and bronchitis. Such additional therapeutic agents include, e.g., sympathomimetics (e.g., albuterol), antibiotics, deoxyribonucleases (e.g., Pulmozyme®), anticholinergic drugs, anti-IgE inhibitors (e.g., anti-IgE antibodies), and corticosteroids.

In some embodiments, a highly-concentrated antibody solution described herein can be formulated for administration to a subject along with intravenous gamma globulin therapy (IVIG), plasmapheresis, plasma replacement, or plasma exchange. In some embodiments, an anti-C5 antibody can be formulated for use before, during, or after a kidney transplant.

When a highly-concentrated antibody solution described herein is to be used in combination with a second active agent, the agents can be formulated separately or together. For example, the respective pharmaceutical compositions can be mixed, e.g., just prior to administration, and administered together or can be administered separately, e.g., at the same or different times (see below).

Methods for Preparing the Highly-Concentrated Antibody Solutions

The disclosure also provides exemplary methods for preparing a highly-concentrated antibody solution containing more than 100 mg/mL of an anti-C5 antibody. For example, as described herein and exemplified in the working examples, the inventors have identified improved methods for concentrating an anti-C5 antibody solution that results not only in a higher recovery of antibody from the process, but also a more concentrated final solution. That is, under this method the anti-C5 antibody eculizumab can be concentrated in solution up to 224 mg/mL with an 85% recovery of the antibody starting material.

The method requires a first aqueous solution comprising an anti-C5 antibody, the first aqueous solution having a first formulation and comprising, preferably, no more than 50 mg/mL of the anti-C5 antibody. In some embodiments, the first aqueous solution having a first formulation comprises no more than approximately 40 mg/mL of the anti-C5 antibody. In some embodiments, the provided solution contains between about 20 to about 50 (e.g., 21, 22, 23, 24, 25, 26, 27, 28, 29, 30, 31, 32, 33, 34, 35, 36, 37, 38, 39, 40, 41, 42, 43, 44, 45, 46, 47, 48, or 49) mg/mL of the anti-C5 antibody. In some embodiments, the provided solution contains less than 50 (e.g., less than 49, 48, 47, 46, 45, 44, 43, 42, 41, 40, 39, 38, 37, 36, 35, 34, 33, 32, 31, 30, 29, or 28) mg/mL of the anti-C5 antibody. The first formulation buffer can be, e.g., a phosphate-based buffer such as phosphate-buffered saline. Suitable phosphate-based buffers for use in these preparation methods are set forth in the working examples. In some embodiments, the first aqueous solution is initially concentrated to around 30 mg/mL to 50 mg/mL of the anti-C5 antibody. For example, the first aqueous solution can be concentrated to around 30 mg/mL to 40 mg/mL of the anti-C5 antibody using a tangential flow filter (TFF) or a stir cell. In some embodiments, the first aqueous solution is obtained by concentrating a "starting" solution having an anti-C5 antibody concentration of less than, or equal to, 15 (e.g., less than or equal to 14, 13, 12, 11, 10, 9, 8, 7, 6, 5, 4, 3, 2 or even 1) mg/mL. The formulation of the starting solution can be the same or can be different from the formulation of the first aqueous solution.

The method includes subjecting the first aqueous solution to diafiltration to thereby produce a second aqueous solution. Diafiltration is a membrane-based separation process useful for reducing, removing, or exchanging salts or other buffer components from a solution of interest. Diafiltration involves a buffering-exchanging process where a protein solution (e.g., the first solution containing the anti-C5 antibody) is placed onto a filter having a specified pore size, wherein pressure applied to the solution upon the column forces components of the solution that are smaller than the pores of the filter to pass through the filter. Higher molecular weight species, such as an anti-C5 antibody, that are unable to pass through the pores of the filter are retained (retentate). By applying a volume of a second buffer solution into the retentate container during the diafiltration process, the lower molecular weight buffer components can be exchanged resulting in a retentate having a different formulation than that of the first solution. Typically, a volume of the second buffer equal to volume of the retentate is applied in each "round" of diafiltration. For example, 5 mL of the first solution can placed on the filter and 5 mL of the second buffer is added to the first solution before or during the application of a pressure suitable to gently force the lower molecular weight components of the buffer (e.g., water, salts, etc.) through the filter. In such an example, pressure would be applied until the initial 10 mL volume was reduced to a 5 mL retentate. A second round of diafiltration could be performed wherein an additional 5 mL of the second buffer is applied to the retentate upon the filter. Pressure is applied to the solution on the filter until the 10 mL volume is reduced again to 5 mL. In some embodiments, diafiltration can involve the use of pressure and/or tangential flow to force low molecular weight molecules across a flat sheet membrane. In some embodiments, the diafiltration buffer can be added continuously during the process to maintain a constant retentate volume while the buffer is exchanged.

In some embodiments, one round of diafiltration will be performed. In some embodiments, two or more (e.g., three, four, five, six, seven, eight, nine, or 10 or more) rounds of diafiltration are performed. Following the one or more rounds of diafiltration, the original formulation of the first aqueous solution has been exchanged to a second formulation, thus resulting in a second aqueous solution. In some embodiments, the second formulation comprises: at least 20 mM histidine; at least 50 mM serine; at least 2.5% (w/v) sorbitol; and at least 1.5% (w/v) mannitol. Exemplary second formulations are described herein and exemplified in the working examples.

The methods can also include, following the diafiltration step, concentrating the second aqueous solution to produce a concentrated antibody solution comprising greater than 100 mg/mL of the anti-C5 antibody. In some embodiments, the concentration step is performed to produce a concentrated antibody solution having greater than 125 (e.g., 130, 135, 140, 145, 150, 155, 160, 165, 170, 175, 180, 185, 190, 195, 200, 205, 210, 215, 220, or greater than 225) mg/mL. The concentration step can include, e.g., tangential flow filtration or a stir cell.

As described herein, the methods allow at least 90 (e.g., at least 91, 92, 93, 94, 95, 96, 97, 98, 99, or even 100) % of the anti-C5 antibody present in the first aqueous solution to be recovered in the high concentration aqueous solution.

Methods for Producing an Antibody

Suitable methods for producing an antibody, or antigen-binding fragments thereof, in accordance with the disclosure are known in the art (see, e.g., U.S. Pat. No. 6,355,245) and described herein. For example, monoclonal anti-C5 antibodies may be generated using complement component C5-expressing cells, a C5 polypeptide, or an antigenic fragment of C5 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to human complement component C5.

Moreover, antibodies derived from recombinant libraries ("phage antibodies") may be selected using C5-expressing cells, or polypeptides derived therefrom, as bait to isolate the antibodies or polypeptides on the basis of target specificity. The production and isolation of non-human and chimeric anti-C5 antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g., *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J Biol Chem* 263:4318-4322; U.S. Pat. Nos. 5,403,484; 5,223,409; WO88/06630; WO92/15679; U.S. Pat. Nos. 5,780,279; 5,571,698; 6,040,136; Davis et al. (1999) *Cancer Metastasis Rev* 18(4):421-5; and Taylor et al. (1992) *Nucleic Acids Res* 20: 6287-6295; Tomizuka et al. (2000) *Proc Natl Acad Sci USA* 97(2): 722-727, the contents of each of which are incorporated herein by reference in their entirety.

The cell culture supernatants are screened for the desired antibodies, preferentially by immunofluorescent staining of complement component C5-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a complement component C5-expressing cell line, or with Protein-A or -G.

Another embodiment provides a process for the preparation of a bacterial cell line secreting antibodies directed against a C5 protein in a suitable mammal. For example a rabbit is immunized with pooled samples from C5-expressing tissue or cells or C5 polypeptide or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a complement component C5 protein. In that process, a suitable mammal, for example a Balb/c mouse, is immunized with one or more polypeptides or antigenic fragments of C5 or with one or more polypeptides or antigenic fragments derived from a C5-expressing cell, the C5-expressing cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a C5-expressing Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally an immunogenic composition containing human C5 protein (or an immunogenic fragment thereof) several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced onto human constant domain gene segments (for example, U.S. Pat. No. 4,816,567). In this manner, non-human antibodies can be modified to make them more suitable for human clinical application (e.g., methods for treating or preventing a complement associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321: 522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc Natl Acad Sci USA* 90:2551; Jakobovits et al. (1993) *Nature* 362:255-258; Bruggemann et al. (1993) *Year in Immunol.* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a complement component C5 protein, fragments thereof, or cells expressing C5 protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227:381; Marks et al. (1991) *J Mol Biol* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132; 6,680,209; and 4,634,666, and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156 and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 20030229905 A1, 20040010810 A1, 20040093622 A1, 20060040363 A1, 20050054055 A1, 20050076395 A1, and 20050287630 A1. See also International Patent Application Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807;

5,545,806; 5,625,825; 5,625,126; 5,633,425; 5,661,016; 5,770,429; 5,789,650; 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Application Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5:647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *Int Immunol* 6: 579-591; Tuaillon et al. (1995) *J Immunol* 154: 6453-65; Fishwild et al. (1996) *Nature Biotechnol* 14: 845; and Tuaillon et al. (2000) *Eur J Immunol* 10: 2998-3005, the disclosures of each of which are hereby incorporated by reference in their entirety.

In certain embodiments, de-immunized anti-C5 antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-C5 antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, and artificially selected antibodies), synthetic antibodies and semi-synthetic antibodies.

In some embodiments, a recombinant DNA comprising an insert coding for a heavy chain variable domain and/or for a light chain variable domain of an anti-C5 antibody or a C5 protein-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-C5 antibodies can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or the CDRs of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-C5 antibody-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or γ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-C5 antibody or antigen-binding fragment (e.g., Fab, Fv, single-chain (scFv), Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA*, 78:2072-2076) or Tn5 neo (Southern and Berg (1982) *J Mol Appl Genet* 1:327-341). The selectable marker gene can be either linked to the DNA gene sequences to be expressed, or introduced into the same cell by co-transfection (Wigler et al. (1979) *Cell* 16:777-785). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147-7151), polyoma virus (Deans et al. (1984) *Proc Natl Acad Sci USA* 81:1292-1296), or SV40 virus (Lusky and Botchan (1981) *Nature* 293:79-81).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280-289; Cepko et al. (1984) *Cell* 37:1053-1062; and Kaufman (1985) *Proc Natl Acad Sci USA* 82:689-693.

As is evident from the disclosure, the anti-C5 antibodies can be used in therapies (e.g., therapies for a complement associated disorder), including combination therapies.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the human complement component C5 antigen and the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods Enzymol* 121:210-228; PCT Publication No. WO 96/27011; Brennan et al. (1985) *Science* 229:81-83; Shalaby et al. *J Exp Med* (1992) 175:217-225; Kostelny et al. (1992) *J Immunol* 148(5):1547-1553; Hollinger et al. (1993) *Proc Nat Acad Sci USA* 90:6444-6448; Gruber et al. (1994) *J Immunol* 152:5368-5474; and Tutt et al. (1991) *J Immunol* 147:60-69. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368-5374. Alternatively, the antibodies can be "linear antibodies" as described in, e.g., Zapata et al. (1995) *Protein Eng* 8(10): 1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024188 and WO 07/024715, the disclosures of each of which are incorporated herein by reference in their entirety.

Methods for Treatment

The above-described compositions (e.g., any of the high concentration antibody solutions) are useful in, inter alia, methods for treating or preventing a variety of complement-associated disorders (e.g., AP-associated disorders or CP-associated disorders) in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intraocular injection, intraarticular injection, or intramuscular injection (IM).

In some embodiments, a high concentration antibody solution described herein is therapeutically delivered to a subject by way of local administration. As used herein, "local administration" or "local delivery," refers to delivery that does not rely upon transport of the composition or active agent (e.g., an anti-C5 antibody) to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

In some embodiments, a high concentration antibody solution can be locally administered to a joint (e.g., an articulated joint). For example, in embodiments where the complement-associated disorder is arthritis, the solution can be administered directly to a joint (e.g., into a joint space) or in the vicinity of a joint. Examples of intraarticular joints to which a high concentration antibody solution described herein can be locally administered include, e.g., the hip, knee, elbow, wrist, sternoclavicular, temporomandibular, carpal, tarsal, ankle, and any other joint subject to arthritic conditions. A high concentration solution described herein can also be administered to bursa such as, e.g., acromial, bicipitoradial, cubitoradial, deltoid, infrapatellar, ischial, and any other bursa known in the art of medicine.

In some embodiments, a high concentration antibody solution described herein can be locally administered to the eye, e.g., to treat patients afflicted with a complement-associated disorder of the eye such as wet or dry AMD. As used herein, the term "eye" refers to any and all anatomical tissues and structures associated with an eye. The eye has a wall composed of three distinct layers: the outer sclera, the middle choroid layer, and the inner retina. The chamber behind the lens is filled with a gelatinous fluid referred to as the vitreous humor. At the back of the eye is the retina, which detects light. The cornea is an optically transparent tissue, which conveys images to the back of the eye. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

In some embodiments, a high concentration antibody solution described herein is administered to the posterior chamber of the eye. In some embodiments, a high concentration antibody solution is administered intravitreally. In some embodiments, a high concentration antibody solution described herein is administered transsclerally.

It is understood that in some embodiments a high concentration antibody solution described herein can be administered systemically for use in treating, e.g., RA, wet or dry AMD, or any other complement-associated disorder described herein.

A suitable dose of a high concentration antibody solution described herein, which dose is capable of treating or preventing a complement-associated disorder in a subject, can depend on a variety of factors including, e.g., the age, sex, and weight of a subject to be treated and the particular inhibitor compound used. For example, a different dose of an anti-C5 antibody (and thus a different concentration of the antibody in solution or a different volume of a high concentration antibody solution) may be required to treat an elderly subject with RA as compared to the dose of an anti-C5 antibody that is required to treat a younger subject. Other factors affecting the dose administered to the subject include, e.g., the type or severity of the complement-associated disorder. For example, a subject having RA may require administration of a different dosage of a high concentration antibody solution described herein than a subject with AMD. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject is generally governed by the judgment of the treating medical practitioner (e.g., doctor or nurse).

An anti-C5 antibody as part of a high concentration antibody solution described herein can be administered as a fixed dose, or in a milligram per kilogram (mg/kg) dose. In some embodiments where local administration is preferred, a dose can be selected that results in local inhibition of C5 cleavage (through the action of the anti-C5 antibody), but with no substantial effect on systemic complement activity. In some embodiments, the dose can also be chosen to reduce or avoid production of antibodies or other host immune responses against the therapeutic antibodies in the composition. While in no way intended to be limiting, exemplary dosages of an anti-C5 antibody locally administered to the eye of a patient afflicted with AMD include 0.5 mg to 5 mg (e.g., at least 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9. or 5 mg) per dose. The dose, or pharmaceutical unit dosage form, can be provided to the eye of the patient in a volume of, e.g., up to 50 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) microliters. Accordingly, the disclosure embraces and features pharmaceutical unit dosage forms of an anti-C5 antibody for use in treating AMD (e.g., wet or dry AMD) in a patient by intravitreal injection, which dosage form includes between 0.5 mg to 5 mg, inclusive in a volume of not more than 50 microliters.

While in no way intended to be limiting, exemplary dosages of an anti-C5 antibody locally administered to a joint (e.g., an articulated joint) of a patient afflicted with rheumatoid arthritis (RA) include 0.5 to 10 mg (e.g., at least 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mg) per dose. The dose, or pharmaceutical unit dosage form, can be provided to a joint of the patient in a volume of, e.g., up to 500 (e.g., one, two, three, four, five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500) microliters. Accordingly, the disclosure embraces and features pharmaceutical unit dosage forms of an anti-C5 antibody for use in treating RA in a patient by intraarticular injection, which dosage form includes between 0.5 mg to 10 mg, inclusive in a volume of not more than 500 microliters.

Methods for detecting systemic hemolytic activity, as well as inhibition of said activity, are well known in the art and are described herein.

In some embodiments, the concentrated solution of an anti-C5 antibody can be diluted into a pharmaceutically-acceptable diluent for, e.g., systemic delivery of the antibody to the subject. While in no way intended to be limiting, exemplary dosages of an anti-C5 antibody to be administered systemically to treat complement-associated disorder include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg.

A therapeutically-effective amount of an anti-C5 antibody described herein can be readily determined by one of ordinary skill in the art based, in part, on the effect of the administered antibody, or the combinatorial effect of the antibody and one or more additional active agents, if more than one agent is used. A therapeutically effective amount of an antibody described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of the complement-associated disorder. For example, a therapeutically effective amount of a C5-binding polypeptide can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the anti-C5 antibodies described herein can further be evaluated in, e.g., Phase 1 dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent (e.g., an anti-C5 antibody) that will elicit the desired biological or medical response (e.g., an improvement in one or more symptoms of a complement-associated disorder). In some embodiments, a high concentration antibody solution described herein contains a therapeutically effective amount of the anti-C5 antibody. In some embodiments, the high concentration antibody solution described herein contains an anti-C5 antibody and one or more (e.g., one, two, three, four, five, six, seven, eight, nine, 10, or 11 or more) additional therapeutic agents such that the composition as a whole is therapeutically effective. For example, a high concentration antibody solution can contain anti-C5 antibody and a VEGF inhibitor (e.g., an anti-VEGF antibody such as bevacizumab), wherein the anti-C5 antibody and VEGF inhibitor are each at a concentration that when combined are therapeutically effective for treating or preventing a complement-associated disorder in a subject.

Toxicity and therapeutic efficacy of such compositions can be determined by known pharmaceutical procedures in cell cultures or experimental animals (e.g., animal models of any of the complement-associated disorders described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-C5 antibody that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies lies generally within a range of circulating concentrations of the anti-C5 antibody that include the $ED_{50}$ with little or no toxicity. The dosage may vary within this range depending upon the dosage form employed and the route of administration utilized. For an anti-C5 antibody used as described herein (e.g., for treating or preventing a complement-associated disorder), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or by ELISA.

In some embodiments, the methods can be performed in conjunction with other therapies for complement-associated disorders. For example, the composition can be administered to a subject at the same time, prior to, or after, plasmapheresis, IVIG therapy, plasma replacement, or plasma exchange. See, e.g., Appel et al. (2005) *J Am Soc Nephrol* 16:1392-1404. In some embodiments, a high concentration antibody solution described herein is not administered in conjunction with IVIG. In some embodiments, e.g., for patients with aHUS, the composition can be administered to a subject at the same time, prior to, or after, a kidney transplant.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a solution comprising a high concentration of an anti-C5 antibody).

As described above, the high concentration antibody solutions described herein can be used to treat a variety of complement-associated disorders such as, e.g., AP-associated disorders and/or CP-associated disorders. Such disorders include, without limitation, rheumatoid arthritis (RA); antiphospholipid antibody syndrome; lupus nephritis; ischemia-reperfusion injury; atypical hemolytic uremic syndrome (aHUS); typical or infectious hemolytic uremic syndrome (tHUS); dense deposit disease (DDD); paroxysmal nocturnal hemoglobinuria (PNH); neuromyelitis optica (NMO); multifocal motor neuropathy (MMN); multiple sclerosis (MS); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; and traumatic brain injury. (See, e.g., Holers (2008) *Immunological Reviews* 223:300-316 and Holers and Thurman (2004) *Molecular Immunology* 41:147-152.) In some embodiments, the complement-associated disorder is a complement-associated vascular disorder such as, but not limited to, a diabetes-associated vascular disorder (e.g., of the eye), central retinal vein occlusion, a cardiovascular disorder, myocarditis, a cerebrovascular disorder, a peripheral (e.g., musculoskeletal) vascular disorder, a renovascular disorder, a mesenteric/enteric vascular disorder, revascularization to transplants and/or replants, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease (arteritis), venous gas embolus (VGE), and restenosis following stent placement, rotational atherectomy, and percutaneous transluminal coronary angioplasty (PTCA). (See, e.g., U.S. patent application publication no. 20070172483.) Additional complement-associated disorders include, without limitation, myasthenia gravis, cold agglutinin disease, dermatomyositis, Graves' disease, atherosclerosis, Alzheimer's disease, Guillain-Barré Syndrome, Degos' disease, graft rejection (e.g., transplant rejection), sepsis, burn (e.g., severe burn), systemic inflammatory response sepsis, septic shock, spinal cord injury, glomerulonephritis, Hashimoto's thyroiditis, type I diabetes, psoriasis, pemphigus, autoimmune hemolytic anemia (AIHA), idiopathic thrombocytopenic purpura (ITP), Goodpasture syndrome, antiphospholipid syndrome (APS), and catastrophic APS (CAPS). In some embodiments, the high concentration antibody solutions described herein can be used in methods for treating thrombotic microangiopathy (TMA), e.g., TMA associated with a complement-associated disorder such as any of the complement-associated disorders described herein.

Complement-associated disorders also include complement-associated pulmonary disorders such as, but not limited to, asthma, bronchitis, a chronic obstructive pulmonary disease (COPD), an interstitial lung disease, α-1 anti-trypsin deficiency, emphysema, bronchiectasis, bronchiolitis obliterans, alveolitis, sarcoidosis, pulmonary fibrosis, and collagen vascular disorders.

As used herein, a subject "at risk for developing a complement-associated disorder" (e.g., an AP-associated disorder or a CP-associated disorder) is a subject having one or more (e.g., two, three, four, five, six, seven, or eight or more) risk factors for developing the disorder. Risk factors will vary depending on the particular complement-associated disorder, but are well known in the art of medicine. For example, risk factors for developing DDD include, e.g., a predisposition to develop the condition, i.e., a family history of the condition or a genetic predisposition to develop the condition such as, e.g., one or more mutations in the gene encoding complement factor H (CFH), complement factor H-related 5 (CFHR5), and/or complement component C3 (C3). Such DDD-associated mutations as well methods for determining whether a subject carries one or more of the mutations are known in the art and described in, e.g., Licht et al. (2006) *Kidney Int* 70:42-50; Zipfel et al. (2006) "The role of complement in membranoproliferative glomerulonephritis," In: Complement and Kidney Disease, Springer, Berlin, pages 199-221; Ault et al. (1997) *J Biol Chem* 272:25168-75; Abrera-Abeleda et al. (2006) *J Med Genet* 43:582-589; Poznansky et al. (1989) *J Immunol* 143:1254-1258; Jansen et al. (1998) *Kidney Int* 53:331-349; and Hegasy et al. (2002) *Am J Pathol* 161:2027-2034. Thus, a human at risk for developing DDD can be, e.g., one who has one or more DDD-associated mutations in the gene encoding CFH or one with a family history of developing the disease.

Risk factors for TTP are well known in the art of medicine and include, e.g., a predisposition to develop the condition, i.e., a family history of the condition or a genetic predisposition to develop the condition such as, e.g., one or more mutations in the ADAMTS13 gene. ADAMTS13 mutations associated with TTP are reviewed in detail in, e.g., Levy et al. (2001) *Nature* 413:488-494; Kokame et al. (2004) *Semin Hematol* 41:34-40; Licht et al. (2004) *Kidney Int* 66:955-958; and Noris et al. (2005) *J Am Soc Nephrol* 6:1177-1183. Risk factors for TTP also include those conditions or agents that are known to precipitate TTP, or TTP recurrence, such as, but not limited to, cancer, bacterial infections (e.g., *Bartonella* sp. infections), viral infections (e.g., HIV and Kaposi's sarcoma virus), pregnancy, or surgery. See, e.g., Avery et al. (1998) *Am J Hematol* 58:148-149 and Tsai, supra. TTP, or recurrence of TTP, has also been associated with the use of certain therapeutic agents (drugs) including, e.g., ticlopidine, FK506, corticosteroids, tamoxifen, or cyclosporin A (see, e.g., Gordon et al. (1997) *Sem in Hematol* 34(2):140-147). Hereinafter, such manifestations of TTP may be, where appropriate, referred to as, e.g., "infection-associated TTP," "pregnancy-associated TTP," or "drug-associated TTP." Thus, a human at risk for developing TTP can be, e.g., one who has one or more TTP-associated mutations in the ADAMTS13 gene. A human at risk for developing a recurrent form of TTP can be one, e.g., who has had TTP and has an infection, is pregnant, or is undergoing surgery.

Risk factors for aHUS are well known in the art of medicine and include, e.g., a predisposition to develop the condition, i.e., a family history of the condition or a genetic predisposition to develop the condition such as, e.g., one or more mutations in complement Factor H (CFH), membrane cofactor protein (MCP; CD46), C4b-binding protein, complement factor B (CFB), or complement factor I (CFI). (See, e.g., Warwicker et al. (1998) *Kidney Int* 53:836-844; Richards et al. (2001) *Am J Hum Genet* 68:485-490; Caprioli et al. (2001) *Am Soc Nephrol* 12:297-307; Neuman et al. (2003) *J Med Genet* 40:676-681; Richards et al. (2006) *Proc Natl Acad Sci USA* 100:12966-12971; Fremeaux-Bacchi et al. (2005) *J Am Soc Nephrol* 17:2017-2025; Esparza-Gordillo et al. (2005) *Hum Mol Genet* 14:703-712; Goicoechea de Jorge et al. (2007) *Proc Natl Acad Sci USA* 104(1):240-245; Blom et al. (2008) *J Immunol* 180(9):6385-91; and Fremeaux-Bacchi et al. (2004) *J Medical Genet* 41:e84). (See also Kavanagh et al. (2006) supra.) Risk factors also include, e.g., infection with *Streptococcus pneumoniae*, pregnancy, cancer, exposure to anti-cancer agents (e.g., quinine, mitomycin C, cisplatin, or bleomycin), exposure to immunotherapeutic agents (e.g., cyclosporine, OKT3, or interferon), exposure to anti-platelet agents (e.g., ticlopidine or clopidogrel), HIV infection, transplantation, autoimmune disease, and combined methylmalonic aciduria and homocystinuria (cblC). See, e.g., Constantinescu et al. (2004) *Am J Kidney Dis* 43:976-982; George (2003) *Curr Opin Hematol* 10:339-344; Gottschall et al. (1994) *Am J Hematol* 47:283-289; Valavaara et al. (1985) *Cancer* 55:47-50; Miralbell et al. (1996) *J Clin Oncol* 14:579-585; Dragon-Durey et al. (2005) *J Am Soc Nephrol* 16:555-63; and Becker et al. (2004) *Clin Infect Dis* 39:S267-S275.

Risk factors for HELLP are well known in the art of medicine and include, e.g., multiparous pregnancy, maternal age over 25 years, Caucasian race, the occurrence of preeclampsia or HELLP in a previous pregnancy, and a history of poor pregnancy outcome. (See, e.g., Sahin et al. (2001) *Nagoya Med J* 44(3):145-152; Sullivan et al. (1994) *Am J Obstet Gynecol* 171:940-943; and Padden et al. (1999) *Am Fam Physician* 60(3):829-836.) For example, a pregnant, Caucasian woman who developed preeclampsia during a first pregnancy can be one at risk for developing HELLP syndrome during, or following, a second pregnancy.

Risk factors for CAD are well known in the art of medicine and include, e.g., conditions or agents that are known to precipitate CAD, or CAD recurrence, such as, but not limited to, neoplasms or infections (e.g., bacterial and viral infections). Conditions known to be associated with the development of CAD include, e.g., HIV infection (and AIDS), hepatitis C infection, *Mycoplasma pneumonia* infection, Epstein-Barr virus (EBV) infection, cytomegalovirus (CMV) infection, rubella, or infectious mononucleosis. Neoplasms associated with CAD include, without limitation, non-Hodgkin's lymphoma. Hereinafter, such manifestations of CAD may be, where appropriate, referred to as, e.g., "infection-associated CAD" or "neoplasm-associated CAD." Thus, a human at risk for developing CAD can be, e.g., one who has an HIV infection, rubella, or a lymphoma. See also, e.g., Gertz (2006) *Hematology* 1:19-23; Horwitz et al. (1977) *Blood* 50:195-202; Finland and Barnes (1958) *AMA Arch Intern Med* 191:462-466; Wang et al. (2004) *Acta Paediatr Taiwan* 45:293-295; Michaux et al. (1998) *Ann Hematol* 76:201-204; and Chang et al. (2004) *Cancer Genet Cytogenet* 152:66-69.

Risk factors for myasthenia gravis (MG) are well known in the art of medicine and include, e.g., a predisposition to develop the condition, i.e., a family history of the condition or a genetic predisposition to develop the condition such as familial MG. For example, some HLA types are associated with an increased risk for developing MG. Risk factors for MG include the ingestion or exposure to certain MG-inducing drugs such as, but not limited to, D-penicillamine. See, e.g., Drosos et al. (1993) *Clin Exp Rheumatol* 11(4): 387-91 and Kaeser et al. (1984) *Acta Neurol Scand Suppl* 100:39-47. As MG can be episodic, a subject who has previously experienced one or more symptoms of having MG can be at risk for relapse. Thus, a human at risk for developing MG can be, e.g., one who has a family history of MG and/or one who has ingested or been administered an MG-inducing drug such as D-penicillamine.

As used herein, a subject "at risk for developing CAPS" is a subject having one or more (e.g., two, three, four, five, six, seven, or eight or more) risk factors for developing the disorder. Approximately 60% of the incidences of CAPS are preceded by a precipitating event such as an infection. Thus, risk factors for CAPS include those conditions known to precipitate CAPS such as, but not limited to, certain cancers (e.g., gastric cancer, ovarian cancer, lymphoma, leukemia, endometrial cancer, adenocarcinoma, and lung cancer), pregnancy, puerperium, transplantation, primary APS, rheumatoid arthritis (RA), systemic lupus erythematosus (SLE), surgery (e.g., eye surgery), and certain infections. Infections include, e.g., parvovirus B19 infection and hepatitis C infection. Hereinafter, such manifestations of CAPS may be referred to as, e.g., "cancer-associated CAPS," "transplantation-associated CAPS," "RA-associated CAPS," "infection-associated CAPS," or "SLE-associated CAPS." See, e.g., Soltész et al. (2000) *Haematologia (Budep)* 30(4):303-311; Ideguchi et al. (2007) *Lupus* 16(1):59-64; Manner et al. (2008) *Am J Med Sci* 335(5):394-7. Miesbach et al. (2006) *Autoimmune Rev* 6(2):94-7; Gómez-Puerta et al. (2006) *Autoimmune Rev* 6(2):85-8; Gómez-Puerta et al. (2006) *Semin Arthritis Rheum* 35(5):322-32; Kasamon et al. (2005) *Haematologia* 90(3):50-53; Atherson et al. (1998) *Medicine* 77(3):195-207; and Canpolat et al. (2008) *Clin Pediatr* 47(6):593-7. Thus, a human at risk for developing CAPS can be, e.g., one who has primary CAPS and/or a cancer that is known to be associated with CAPS.

From the above it will be clear that subjects "at risk for developing a complement-associated disorder" (e.g., an AP-associated disorder or a CP-associated disorder) are not all the subjects within a species of interest.

A subject "suspected of having a complement-associated disorder" (e.g., an alternative complement pathway-associated disorder) is one having one or more (e.g., two, three, four, five, six, seven, eight, nine, or 10 or more) symptoms of the disease. Symptoms of these disorders will vary depending on the particular disorder, but are known to those of skill in the art of medicine. For example, symptoms of DDD include, e.g.: one or both of hematuria and proteinuria; acute nephritic syndrome; drusen development and/or visual impairment; acquired partial lipodystrophy and complications thereof; and the presence of serum C3 nephritic factor (C3NeF), an autoantibody directed against C3bBb, the C3 convertase of the alternative complement pathway. (See, e.g., Appel et al. (2005), supra). Symptoms of aHUS include, e.g., severe hypertension, proteinuria, uremia, lethargy/fatigue, irritability, thrombocytopenia, microangiopathic hemolytic anemia, and renal function impairment (e.g., acute renal failure). Symptoms of TTP include, e.g., microthrombi, thrombocytopenia, fever, low ADAMTS13 metalloproteinase expression or activity, fluctuating central nervous system abnormalities, renal failure, microangiopathic hemolytic anemia, bruising, purpura, nausea and vomiting (e.g., resulting from ischemia in the GI tract or from central nervous system involvement), chest pain due to cardiac ischemia, seizures, and muscle and joint pain. Symptoms of RA can include, e.g., stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing. Symptoms of HELLP are known in the art of medicine and include, e.g., malaise, epigastric pain, nausea, vomiting, headache, right upper quadrant pain, hypertension, proteinuria, blurred vision, gastrointestinal bleeding, hypoglycemia, paresthesia, elevated liver enzymes/liver damage, anemia (hemolytic anemia), and low platelet count, any of which in combination with pregnancy or recent pregnancy. (See, e.g., Tomsen (1995) *Am J Obstet Gynecol* 172:1876-1890; Sibai (1986) *Am J Obstet Gynecol* 162:311-316; and Padden (1999), supra.) Symptoms of PNH include, e.g., hemolytic anemia (a decreased number of red blood cells), hemoglobinuria (the presence of hemoglobin in the urine particularly evident after sleeping), and hemoglobinemia (the presence of hemoglobin in the bloodstream). PNH-afflicted subjects are known to have paroxysms, which are defined here as incidences of dark-colored urine, dysphagia, fatigue, erectile dysfunction, thrombosis, and recurrent abdominal pain.

Symptoms of CAPS are well known in the art of medicine and include, e.g., histopathological evidence of multiple small vessel occlusions; the presence of antiphospholipid antibodies (usually at high titer), vascular thromboses, severe multi-organ dysfunction, malignant hypertension, acute respiratory distress syndrome, disseminated intravascular coagulation, microangiopathic hemolytic anemia, schistocytes, and thrombocytopenia. CAPS can be distinguished from APS in that patients with CAPS generally present with severe multiple organ dysfunction or failure, which is characterized by rapid, diffuse small vessel ischemia and thromboses predominantly affecting the parenchymal organs. In contrast, APS is associated with single venous or arterial medium-to-large blood vessel occlusions. Symptoms of MG include, e.g., fatigability and a range of muscle weakness-related conditions including: ptosis (of one or both eyes), diplopia, unstable gait, depressed or distorted facial expressions, and difficulty chewing, talking, or swallowing. In some instances, a subject can present with partial or complete paralysis of the respiratory muscles. Symptoms of CAD include, e.g., pain, fever, pallor, anemia, reduced blood flow to the extremities (e.g., with gangrene), and renal disease or acute renal failure. In some embodiments, the symptoms can occur following exposure to cold temperatures.

From the above it will be clear that subjects "suspected of having a complement-associated disorder" are not all the subjects within a species of interest.

In some embodiments, the methods can include identifying the subject as one having, suspected of having, or at risk for developing, a complement-associated disorder in a subject. Suitable methods for identifying the subject are known in the art. For example, suitable methods (e.g., sequencing techniques or use of microarrays) for determining whether a human subject has a DDD-associated mutation in a CFH, CFHR5, or C3 gene are described in, e.g., Licht et al. (2006) *Kidney Int* 70:42-50; Zipfel et al. (2006), supra; Ault et al. (1997) *J Biol Chem* 272:25168-75; Abrera-Abeleda et al. (2006) *J Med Genet* 43:582-589; Poznansky et al. (1989) *J Immunol* 143:1254-1258; Jansen et al. (1998) *Kidney Int* 53:331-349; and Hegasy et al. (2002) *Am J Pathol* 161: 2027-2034. Methods for detecting the presence of characteristic DDD-associated electron-dense deposits are also well known in the art. For example, a medical practitioner can obtain a tissue biopsy from the kidney of a patient and subject the tissue to electron microscopy. The medical practitioner may also examine the tissue by immunofluorescence to detect the presence of C3 using an anti-C3 antibody and/or light microscopy to determine if there is membranoproliferative glomerulonephritis. See, e.g., Walker et al. (2007) *Mod Pathol* 20:605-616 and Habib et al. (1975) *Kidney Int* 7:204-215. In some embodiments, the identification of a subject as one having DDD can include assaying a blood sample for the presence of C3NeF. Methods for detecting the presence of C3NeF in blood are described in, e.g., Schwertz et al. (2001) *Pediatr Allergy Immunol* 12:166-172.

In some embodiments, the medical practitioner can determine whether there is increased complement activation in a subject's serum. Indicia of increased complement activation include, e.g., a reduction in CH50, a decrease in C3, and an increase in C3dg/C3d. See, e.g., Appel et al. (2005), supra. In some embodiments, a medical practitioner can examine a subject's eye for evidence of the development of drusen and/or other visual pathologies such as AMD. For example, a medical practitioner can use tests of retinal function such as, but not limited to, dark adaptation, electroretinography, and electrooculography (see, e.g., Colville et al. (2003) *Am J Kidney Dis* 42:E2-5).

Methods for identifying a subject as one having, suspected of having, or at risk for developing, TTP are also known in the art. For example, Miyata et al. describe a variety of assays for measuring ADAMTS13 activity in a biological sample obtained from a subject (*Curr Opin Hematol* (2007) 14(3):277-283). Suitable ADAMTS13 activity assays, as well as phenotypically normal ranges of ADAMTS13 activity in a human subject, are described in, e.g., Tsai (2003)*J Am Soc Nephrol* 14:1072-1081; Furlan et al. (1998) *New Engl J Med* 339:1578-1584; Matsumoto et al. (2004) *Blood* 103:1305-1310; and Mori et al. (2002) *Transfusion* 42:572-580. Methods for detecting the presence of inhibitors of ADAMTS13 (e.g., autoantibodies that bind to ADAMTS13) in a biological sample obtained from a subject are known in the art. For example, a serum sample from a patient can be mixed with a serum sample from a subject without TTP to detect the presence of anti-ADAMTS13 antibodies. In another example, immunoglobulin protein can be isolated from patient serum and used in in vitro ADAMTS13 activity assays to determine if an anti-ADAMTS13 antibody is present. See, e.g., Dong et al. (2008) *Am J Hematol* 83(10):815-817. In some embodiments, risk of developing TTP can be determined by assessing whether a patient carries one or more mutations in the ADAMTS13 gene. Suitable methods (e.g., nucleic acid arrays or DNA sequencing) for detecting a mutation in the ADAMTS13 gene are known in the art and described in, e.g., Levy et al., supra; Kokame et al., supra; Licht et al., supra; and Noris et al., supra.

In addition, methods for identifying a subject as one having, suspected of having, or at risk for developing aHUS are known in the art. For example, laboratory tests can be performed to determine whether a human subject has thrombocytopenia, microangiopathic hemolytic anemia, or acute renal insufficiency. Thrombocytopenia can be diagnosed by a medical professional as one or more of: (i) a platelet count that is less than 150,000/mm$^3$ (e.g., less than 60,000/mm$^3$); (ii) a reduction in platelet survival time, reflecting enhanced platelet disruption in the circulation; and (iii) giant platelets observed in a peripheral smear, which is consistent with secondary activation of thrombocytopoiesis. Microangiopathic hemolytic anemia can be diagnosed by a medical professional as one or more of: (i) hemoglobin concentrations that are less than 10 mg/dL (e.g., less than 6.5 mg/dL); (ii) increased serum lactate dehydrogenase (LDH) concentrations (>460 U/L); (iii) hyperbilirubinemia, reticulocytosis, circulating free hemoglobin, and low or undetectable haptoglobin concentrations; and (iv) the detection of fragmented red blood cells (schistocytes) with the typical aspect of burr or helmet cells in the peripheral smear together with a negative Coombs test. (See, e.g., Kaplan et al. (1992) "Hemolytic Uremic Syndrome and Thrombotic Thrombocytopenic Purpura," Informa Health Care (ISBN 0824786637) and Zipfel (2005) "Complement and Kidney Disease," Springer (ISBN 3764371668).)

A subject can also be identified as having aHUS by evaluating blood concentrations of C3 and C4 as a measure of complement activation or dysregulation. In addition, as is clear from the foregoing disclosure, a subject can be identified as having genetic aHUS by identifying the subject as harboring one or more mutations in a gene associated with aHUS such as CFI, CFB, CFH, or MCP (supra). Suitable methods for detecting a mutation in a gene include, e.g., DNA sequencing and nucleic acid array techniques. (See, e.g., Breslin et al. (2006) *Clin Am Soc Nephrol* 1:88-99 and Goicoechea de Jorge et al. (2007) *Proc Natl Acad Sci USA* 104:240-245.)

Methods for diagnosing a subject as one having, suspected of having, or at risk for developing, RA are also known in the art of medicine. For example, a medical practitioner can examine the small joints of the hands, wrists, feet, and knees to identify inflammation in a symmetrical distribution. The practitioner may also perform a number of tests to exclude other types of joint inflammation including arthritis due to infection or gout. In addition, rheumatoid arthritis is associated with abnormal antibodies in the blood circulation of afflicted patients. For example, an antibody referred to as "rheumatoid factor" is found in approximately 80% of patients. In another example, anti-citrulline antibody is present in many patients with rheumatoid arthritis and thus it is useful in the diagnosis of rheumatoid arthritis when evaluating patients with unexplained joint inflammation. See, e.g., van Venrooij et al. (2008) *Ann NY Acad Sci* 1143:268-285 and Habib et al. (2007) *Immunol Invest* 37(8):849-857. Another antibody called "the antinuclear antibody" (ANA) is also frequently found in patients with rheumatoid arthritis. See, e.g., Benucci et al. (2008) *Clin Rheumatol* 27(1):91-95; Julkunen et al. (2005) *Scan J Rheumatol* 34(2):122-124; and Miyawaki et al. (2005) *J Rheumatol* 32(8):1488-1494.

A medical practitioner can also examine red blood cell sedimentation rate to help in diagnosing RA in a subject. The sedimentation rate can be used as a crude measure of the inflammation of the joints and is usually faster during disease flares and slower during remissions. Another blood test that can be used to measure the degree of inflammation present in the body is the C-reactive protein.

Furthermore, joint x-rays can also be used to diagnose a subject as having rheumatoid arthritis. As RA progresses, the x-rays can show bony erosions typical of rheumatoid arthritis in the joints. Joint x-rays can also be helpful in monitoring the progression of disease and joint damage over time. Bone scanning, a radioactive test procedure, can demonstrate the inflamed joints.

Methods for identifying a subject as one having, suspected of having, or at risk for developing, HELLP are known in the art of medicine. Hallmark symptoms of HELLP syndrome include hemolysis, elevated liver enzymes, and low platelet count. Thus, a variety of tests can be performed on blood from a subject to determine the level of hemolysis, the concentration of any of a variety of liver enzymes, and the platelet level in the blood. For example, the presence of schistocytes and/or elevated free hemoglobin, bilirubin, or serum LDH levels is an indication of intravascular hemolysis. Routine laboratory testing can be used to determine the platelet count as well as the blood level of liver enzymes such as, but not limited to, aspartate aminotransferase (AST) and alanine transaminase (ALT). Suitable methods for identifying a subject as having HELLP syndrome are also described in, e.g., Sibai et al. (1993), supra; Martin et al. (1990), supra; Padden (1999), supra; and Gleicher and Buttino (1998) "Principles & Practice of Medical Therapy in Pregnancy," 3$^{rd}$ Edition, Appleton & Lange (ISBN 083857677X).

Methods for identifying a subject as having, suspected of having, or at risk for developing PNH are known in the art of medicine. The laboratory evaluation of hemolysis normally includes hematologic, serologic, and urine tests. Hematologic tests include an examination of the blood smear for morphologic abnormalities of red blood cells (RBC), and the measurement of the reticulocyte count in whole blood (to determine bone marrow compensation for RBC loss). Serologic tests include lactate dehydrogenase (LDH; widely performed), and free hemoglobin (not widely performed) as a direct measure of hemolysis. LDH levels, in the absence of tissue damage in other organs, can be useful in the diagnosis and monitoring of patients with hemolysis. Other serologic tests include bilirubin or haptoglobin, as measures of breakdown products or scavenging reserve, respectively. Urine tests include bilirubin, hemosiderin, and free hemoglobin, and are generally used to measure gross severity of hemolysis and for differentiation of intravascular vs. extravascular etiologies of hemolysis rather than routine monitoring of hemolysis. Further, RBC numbers, RBC hemoglobin, and hematocrit are generally performed to determine the extent of any accompanying anemia.

Suitable methods for identifying the subject as having MG can be qualitative or quantitative. For example, a medical practitioner can examine the status of a subject's motor functions using a physical examination. Other qualitative tests include, e.g., an ice-pack test, wherein an ice pack is applied to a subject's eye (in a case of ocular MG) to determine if one or more symptoms (e.g., ptosis) are improved by cold (see, e.g., Sethi et al. (1987) *Neurology* 37(8):1383-1385). Other tests include, e.g., the "sleep test," which is based on the tendency for MG symptoms to improve following rest. In some embodiments, quantitative or semi-quantitative tests can be employed by a medical practitioner to determine if a subject has, is suspected of having, or is at risk for developing, MG. For example, a medical practitioner can perform a test to detect the presence or amount of MG-associated autoantibodies in a serum sample obtained from a subject. MG-associated autoantibodies include, e.g., antibodies that bind to, and modulate the activity of, acetylcholine receptor (AChR), muscle-specific receptor tyrosine kinase (MuSK), and/or striational protein. (See, e.g., Conti-Fine et al. (2006), supra). Suitable assays useful for detecting the presence or amount of an MG-associated antibody in a biological sample are known in the art and described in, e.g., Hoch et al. (2001) *Nat Med* 7:365-368; Vincent et al. (2004) *Semin Neurol* 24:125-133; McConville et al. (2004) *Ann Neurol* 55:580-584: Boneva et al. (2006) *J Neuroimmunol* 177:119-131; and Romi et al. (2005) *Arch Neurol* 62:442-446.

Additional methods for diagnosing MG include, e.g., electrodiagnostic tests (e.g., single-fiber electromyography) and the Tensilon (or edrophonium) test, which involves injecting a subject with the acetylcholinesterase inhibitor edrophonium and monitoring the subject for an improvement in one or more symptoms. See, e.g., Pascuzzi (2003) *Semin Neurol* 23(1):83-88; Katirji et al. (2002) *Neurol Clin* 20:557-586; and "Guidelines in Electrodiagnostic Medicine. American Association of Electrodiagnostic Medicine," *Muscle Nerve* 15:229-253.

A subject can be identified as having CAD using an assay to detect the presence or amount (titer) of agglutinating autoantibodies that bind to the I antigen on red blood cells. The antibodies can be monoclonal (e.g., monoclonal IgM or IgA) or polyclonal. Suitable methods for detecting these antibodies are described in, e.g., Christenson and Dacie (1957) *Br J Haematol* 3:153-164 and Christenson et al. (1957) *Br J Haematol* 3:262-275. A subject can also be diagnosed as having CAD using one or more of a complete blood cell count (CBC), urinalysis, biochemical studies, and a Coombs test to test for hemolysis in blood. For example, biochemical studies can be used to detect elevated lactase dehydrogenase levels, elevated unconjugated bilirubin levels, low haptoglobin levels, and/or the presence of free plasma hemoglobin, all of which can be indicative of acute hemolysis. Other tests that can be used to detect CAD include detecting complement levels in the serum. For example, due to consumption during the acute phase of hemolysis, measured plasma complement levels (e.g., C2, C3, and C4) are decreased in CAD.

Typical (or infectious) HUS, unlike aHUS, is often identifiable by a prodrome of diarrhea, often bloody in nature, which results from infection with a shiga-toxin producing microorganism. A subject can be identified as having typical HUS when shiga toxins and/or serum antibodies against shiga toxin or LPS are detected in the stool of an individual. Suitable methods for testing for anti-shiga toxin antibodies or LPS are known in the art. For example, methods for detecting antibodies that bind to shiga toxins Stx1 and Stx2 or LPS in humans are described in, e.g., Ludwig et al. (2001) *J Clin Microbiol* 39(6):2272-2279.

In some embodiments, a high concentration antibody solution described herein can be administered to a subject as a monotherapy. Alternatively, as described above, the solution can be administered to a subject as a combination therapy with another treatment, e.g., another treatment for DDD, TTP, wet or dry AMD, aHUS, PNH, RA, HELLP, MG, CAD, CAPS, tHUS, or any other complement-associated disorder known in the art or described herein. For example, the combination therapy can include administering to the subject (e.g., a human patient) one or more additional agents (e.g., anti-coagulants, anti-hypertensives, or corticosteroids) that provide a therapeutic benefit to the subject who has, or is at risk of developing, DDD. In some embodiments, the combination therapy can include administering to the subject (e.g., a human patient) by way of a high concentration antibody solution an anti-C5 antibody and an immunosuppressive agent such as Remicade® for use in treating RA. In some embodiments, a high concentration antibody solution and the one or more additional active agents are administered at the same time. In other embodiments, a high concentration antibody solution is administered first in time and the one or more additional active agents are administered second in time. In some embodiments, the one or more additional active agents are administered first in time and high concentration antibody solution is administered second in time.

An anti-C5 antibody described herein can replace or augment a previously or currently administered therapy. For example, upon treating with an anti-C5 antibody, administration of the one or more additional active agents can cease or diminish, e.g., be administered at lower levels. In some embodiments, administration of the previous therapy can be maintained. In some embodiments, a previous therapy will be maintained until the level of the anti-C5 antibody reaches a level sufficient to provide a therapeutic effect. The two therapies can be administered in combination.

Monitoring a subject (e.g., a human patient) for an improvement in a complement-associated disorder, as defined herein, means evaluating the subject for a change in a disease parameter, e.g., an improvement in one or more symptoms of the disease (e.g., an improvement in one or more symptoms of a pulmonary disorder). Such symptoms include any of the symptoms of complement-associated disorders known in the art and/or described herein. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for any of the complement-associated disorders described herein.

Therapeutic Kits

The disclosure also features therapeutic kits containing, among other things, one or more of the high concentration solutions described herein. The therapeutic kits can contain, e.g., a suitable means for delivery of one or more solutions to a patient in need thereof, e.g., a patient afflicted with, suspected of having, or at risk for developing, a complement-associated disorder such as AMD (e.g., wet or dry AMD), a diabetes-associated ocular disorder, central retinal vein occlusion, RA, asthma, or any of the additional complement-associated disorders described herein. In some embodiments, the means is suitable for invasive (e.g., intravascular (e.g., intravenous), subcutaneous, intraarticular, intraocular, intravitreal, or intramuscular) delivery of the solution to a patient. In some embodiments, the means is suitable for subcutaneous delivery of the antibody or antigen-binding fragment thereof to the subject. For example, the means can be a syringe or an osmotic pump. In some embodiments, the solution contained in the kit can be formulated as an eye drop, the means being an eye dropper. In some embodiments, the kit contains a means that is pre-loaded with the solution to be administered. For example, a therapeutic kit can contain a syringe pre-filled with an aqueous solution (e.g., a pen device containing the solution) described herein or the kit can contain a pump (e.g., an osmotic pump) and one or more disposable cassettes configured for use with the pump, the cassettes pre-filled with an aqueous solution described herein. In another example, the kit can contain a transscleral or implantable delivery device (e.g., a plug) that is pre-filled with (or otherwise contains) a high concentration solution described herein.

In some embodiments, the means for delivering the high concentration solution is a pen device for drug delivery.

In some embodiments, the means can be suitable for administration of a high concentration antibody solution described herein to the eye of a patient afflicted with a complement-associated disorder of the eye such as AMD. The means can be, e.g., a syringe, a transscleral patch, or even a contact lens containing or soaked in the solution. The means can, in some embodiments, be an eye dropper, wherein the solution is formulated for such administration. The means can also be, e.g., a contact lens case in embodiments in which, e.g., the solution is formulated as part of a contact lens hydrating, cleaning, or soaking solution. Such therapeutic kits can also include, e.g., one or more additional therapeutic agents for use in treating complement-associated disorder of the eye. The therapeutic agents can be, e.g., bevacizumab or the Fab fragment of bevacizumab, ranibizumab, both sold by Roche Pharmaceuticals, Inc., pegaptanib sodium (Mucogen®; Pfizer, Inc.), and verteporfin (Visudyne®; Novartis). Such a kit can also, optionally, include instructions for administering a solution described herein to a patient.

In some embodiments, the means can be suitable for intraarticular administration of a solution described herein to a patient in need thereof, e.g., a patient afflicted with complement-associated disorder affecting the joints such as RA. The means can be, e.g., a syringe or a double-barreled syringe. See, e.g., U.S. Pat. Nos. 6,065,645 and 6,698,622. A double-barreled syringe is useful for administering to a joint two different compositions with only one injection. Two separate syringes may be incorporated for use in administering the therapeutic while drawing off knee fluid for analysis (tapping) in a push-pull fashion. Additional therapeutic agents that can be administered with the high concentration antibody solutions described herein in conjunction with the double-barreled syringe, or which can otherwise be generally included in the therapeutic kits described herein, include, e.g., NSAIDs, corticosteroids, methotrexate, hydroxychloroquine, anti-TNF agents such as etanercept and infliximab, a B cell depleting agent such as rituximab, an interleukin-1 antagonist, or a T cell costimulatory blocking agent such as abatacept. Such a kit can also, optionally, include instructions for administering a solution described herein to a patient.

In some embodiments, the means is suitable for intrapulmonary delivery of the solutions to a subject, e.g., for use in treatment or prevention of a complement-associated pulmonary disorder such as, but not limited to, COPD or asthma. Accordingly, the means can be, e.g., an oral or nasal inhaler (see above). The inhaler can be, e.g., a metered dose inhaler (MDI) or a nebulizer. Such a kit can also, optionally, include instructions for administering (e.g., self-administration of) the anti-C5a antibody or antigen-binding fragment thereof to a subject. The therapeutic kits are designed for use in treating or preventing a complement-associated pulmonary disorder and can include one or more additional active agents including, but not limited to, another antibody therapeutic (e.g., an anti-IgE antibody, an anti-IL-4 antibody, or an anti-IL-5 antibody), a small molecule anti-IgE inhibitor (e.g., montelukast sodium), a sympathomimetic (e.g., albuterol), an antibiotic (e.g., tobramycin), a deoxyribonuclease (e.g., Pulmozyme®), an anticholinergic drug (e.g., ipratropium bromide), a corticosteroid (e.g., dexamethasone), a β-adrenoreceptor agonist, a leukotriene inhibitor (e.g., zileuton), a 5-lipoxygenase inhibitor, a phosphodiesterase (PDE) inhibitor, a CD23 antagonist, an IL-13 antagonist, a cytokine release inhibitor, a histamine H1 receptor antagonist, an anti-histamine, an anti-inflammatory agent (e.g., cromolyn sodium or any other anti-inflammatory agent known in the art or described herein), or a histamine release inhibitor.

The following examples are intended to illustrate, not limit, the invention.

EXAMPLES

Example 1

Process for Formulating and Concentrating Solutions of Eculizumab

Several high concentration formulations of the anti-C5 antibody, eculizumab, were prepared as follows.

Materials and Methods

Instrumentation

The formulation process utilized a Millipore Pellicon® XL tangential flow filter (TFF), Biomax™ 50K Polyethersulfone membrane having a 50 $cm^2$ surface area. Also used was a Millipore Sterivex 0.22 micron filter unit (catalogue number SVGV010RS).

Reagents

The formulation process also utilized a number of buffers as follows: (a) Formulation Buffer: 20 mM histidine, 50 mM serine, 2.5% sorbitol, 1.5% mannitol, pH 7.4; (b) Phosphate Buffer: 20 mM sodium phosphate, 80 mM NaCl, pH 6.4; (c) Regeneration Buffer: 0.5 M sodium hydroxide; and (d) Storage Buffer: 0.1 M sodium hydroxide. Also used was a buffer containing eculizumab in the above-described Phosphate Buffer.

Formulation

The tangential flow filter (TFF) was prepared by washing from it the storage buffer using 500 mL of deionized water at a feed flow rate (FR) of 50 mL/minute. The permeate outlet was left open during this process. The TFF was equilibrated using 100 mL of the Phosphate Buffer at a feed flow rate of 50 mL/minute with the permeate outlet open. All of these steps were performed at room temperature.

For all subsequent steps, the pressure was maintained at 40 psi by adjusting the permeate outlet flow rate with a clamp. Eculizumab, initially present at approximately 10 mg/mL in Phosphate Buffer (as described above), was concentrated to 50 mg/mL (for the first run and 40 mg/ml for the second run) at a feed flow rate of 50 mL/minute. The concentrated solution was then diafiltered with six equivalent volumes, for the first run, or four equivalent volumes, for the second run, of the Formulation Buffer. Concentration was continued by gradually reducing the feed flow rate to maintain column pressure at 40 psi, until the feed flow rate reached 2 mL/minute.

Recovery Method

To recover the concentrated eculizumab solution from the column, the permeate outlet was closed and the antibody allowed to circulate for five minutes. The TFF was then flushed out with air, while the permeate outlet was closed. The volume of the recovered solution was measured and recorded. A sample of the high concentration antibody solution was filtered through a 0.22 micron Sterivex filter, diluted 1:100 in formulation buffer. The concentration of the antibody in the diluted sample was determined by measuring $A_{280}$ and using an extinction coefficient of 1.46.

Results

The first run process, described above, required 5.3 hours to complete. A detailed description of the physical and chemical parameters of the TFF flow-through (permeate) and retained (retentate) fractions by time is shown in Table 1.

TABLE 1

| Time (min) | Time (hrs) | Pressure (psi) | Feed FR (ml/min) | Permeate FR (ml/min) | Retentate Volume (ml) | Permeate Volume (ml) | Permeate Conc. (mg/ml) | Est. Retentate Conc. (mg/ml) | Details |
|---|---|---|---|---|---|---|---|---|---|
| 0 | 0.0 | 40 | 50 | 0.0 | 550 | 0 | 0.05 | 10.3 | $X^a$ |
| 24 | 0.4 | 40 | 50 | 7.5 | 370 | 180 | 0.05 | 15 | |
| 52 | 0.9 | 40 | 50 | 6.1 | 200 | 350 | 0.05 | 29 | |
| 68 | 1.1 | 40 | 50 | 4.7 | 120 | 425 | 0.05 | 46 | Diafiltr. |
| 104 | 1.7 | 40 | 50 | 3.9 | 120 | 140 | 0.05 | 47 | Diafiltr. |
| 118 | 2.0 | 40 | 50 | 3.6 | 120 | 190 | 0.05 | 47 | Diafiltr. |
| 126 | 2.1 | 40 | 50 | 3.8 | 120 | 220 | 0.05 | 47 | Diafiltr. |
| 146 | 2.4 | 40 | 50 | 4.0 | 120 | 300 | 0.05 | 47 | Diafiltr. |
| 226 | 3.8 | 40 | 50 | 3.8 | 120 | 600 | 0.05 | 47 | Diafiltr. |
| 241 | 4.0 | 40 | 47 | 2.5 | 70 | 38 | 0.05 | 81 | |
| 247 | 4.1 | 40 | 41 | 1.7 | 60 | 48 | 0.05 | 95 | |
| 254 | 4.2 | 40 | 35 | 1.0 | 53 | 55 | 0.05 | 107 | |
| 261 | 4.4 | 40 | 27 | 0.7 | 48 | 60 | 0.05 | 116 | $X^b$ |
| 275 | 4.6 | 40 | 15 | 0.7 | 38 | 70 | 0.05 | 150 | |
| 294 | 4.9 | 40 | 6 | 0.3 | 33 | 75 | 0.05 | 172 | |
| 318 | 5.3 | 35 | 2 | 0.2 | 28 | 80 | 0.05 | 186 | $X^c$ |

$x^a$: 5.7 g at 100% purity; actual measured retentate concentration.

$x^b$: Recovered 98% at 100% purity; actual measured retentate concentration.

$x^c$: Recovered 75% at 100% purity; actual measured retentate concentration.

"Diafiltr." refers to diafiltration.

"FR" refers to flow rate.

The "conc." refers to the concentration of eculizumab in each respective fraction (permeate or retentate).

The initial concentration of eculizumab in the Phosphate Buffer was approximately 10 mg/mL (10.3 mg/mL). Following buffer exchange and diafiltration, the concentration of the solution was initially increased to 116 mg/mL with 98% recovery (100% purity) of the antibody starting material. Further concentration to 186 mg/mL resulted in a 75% recovery (at 100% purity) of the antibody starting material.

The second run process, described above, required 8.8 hours to complete. A detailed description of the physical and chemical parameters of the TFF flow-through (permeate) and retained (retentate) fractions by time is shown in Table 2.

TABLE 2

| Time (min) | Time (hrs) | Pressure (psi) | Feed FR (ml/min) | Permeate FR (ml/min) | Retentate Volume (ml) | Permeate Volume (ml) | Permeate Conc. (mg/ml) | Est. Retentate Conc. (mg/ml) | Details |
|---|---|---|---|---|---|---|---|---|---|
| 0 | 0.0 | 40 | 50 | 0.0 | 620 | 0 | 0.06 | 8 | $X^a$ |
| 10 | 0.2 | 40 | 50 | 7.5 | 545 | 75 | 0.06 | 10 | |
| 33 | 0.6 | 40 | 50 | 6.5 | 395 | 225 | 0.06 | 14 | |
| 50 | 0.8 | 40 | 50 | 5.6 | 300 | 320 | 0.06 | 18 | |
| 70 | 1.2 | 40 | 50 | 4.8 | 205 | 415 | 0.06 | 26 | |
| 85 | 1.4 | 40 | 50 | 3.7 | 150 | 470 | 0.06 | 35 | |
| 137 | 2.3 | 40 | 50 | 3.8 | 150 | 200 | 0.06 | 37 | Diafiltr. |
| 237 | 4.0 | 40 | 50 | 3.0 | 150 | 500 | 0.06 | 37 | Diafiltr. |
| 303 | 5.1 | 40 | 50 | 3.0 | 150 | 700 | 0.06 | 37 | Diafiltr. |
| 367 | 6.1 | 40 | 50 | 3.1 | 150 | 900 | 0.06 | 37 | Diafiltr. |
| 377 | 6.3 | 40 | 50 | 2.6 | 119 | 26 | 0.06 | 45 | |
| 382 | 6.4 | 40 | 50 | 2.8 | 105 | 40 | 0.06 | 51 | |
| 388 | 6.5 | 40 | 50 | 2.0 | 93 | 52 | 0.06 | 58 | |
| 397 | 6.6 | 40 | 50 | 1.8 | 77 | 68 | 0.06 | 70 | |
| 410 | 6.8 | 40 | 50 | 1.1 | 63 | 82 | 0.06 | 86 | |
| 422 | 7.0 | 40 | 40 | 0.8 | 53 | 92 | 0.06 | 101 | |
| 431 | 7.2 | 40 | 30 | 0.7 | 47 | 98 | 0.06 | 114 | |
| 444 | 7.4 | 40 | 21 | 0.5 | 41 | 104 | 0.06 | 131 | |
| 451 | 7.5 | 40 | 16 | 0.3 | 39 | 106 | 0.06 | 138 | |
| 456 | 7.6 | 40 | 15 | 0.4 | 37 | 108 | 0.06 | 145 | |
| 468 | 7.8 | 40 | 9 | 0.2 | 35 | 110 | 0.06 | 151 | $X^b$ |
| 489 | 8.2 | 40 | 5 | 0.1 | 33 | 112 | 0.06 | 163 | |
| 527 | 8.8 | 40 | 2 | 0.2 | 25 | 120 | 0.06 | 208 | $X^c$ |

$x^a$: 5.37 g at 100% purity; actual measured retentate concentration.

$x^b$: Recovered 38% at 100% purity; actual measured retentate concentration.

$x^c$: Recovered 85% at 100% purity; actual measured retentate concentration.

"Diafiltr." refers to diafiltration.

"FR" refers to flow rate.

The "conc." refers to the concentration of eculizumab in each respective fraction (permeate or retentate).

The initial concentration of eculizumab in the Phosphate Buffer was approximately 10 mg/mL (8.4 mg/mL). Following buffer exchange and diafiltration, the concentration of the solution was initially increased to 151 mg/mL with 98% recovery (100% purity as determined by SEC-HPLC) of the antibody starting material. Further concentration to 208 mg/mL resulted in an 85% recovery (at 100% purity) of the antibody starting material.

From the results of the first and second run, diafiltering at 40 mg/mL not only improved the final recovery by 10%, but also allowed for the production of high concentration solution having an even higher final concentration of eculizumab (208 mg/mL).

Example 2

Production of Additional Exemplary Eculizumab Formulations

Two additional formulations were developed and evaluated as to their ability to support high concentration solutions of eculizumab. One of the formulations was a histidine/serine/sorbitol/mannitol (HSSM) formulation and the other, a histidine/trehalose/Tween®-20 (HTT) formulation (see below). Two concentrations of eculizumab, approximately 30 mg/mL and approximately 100 mg/mL, were evaluated in each formulation buffer. A third, phosphate-based buffer was also evaluated. A detailed description of the five different antibody solutions (solutions I to V) evaluated is set forth below.

I. 105 mg/mL eculizumab;
20 mM histidine HCl;
50 mM serine;
3% sorbitol; and
1.5% mannitol; at pH 7.0.
II. 30 mg/mL eculizumab;
20 mM histidine HCl;
50 mM serine;
3% sorbitol; and
1.5% mannitol; at pH 7.0.
III. 105 mg/mL eculizumab;
10 mM histidine HCl;
10% alpha-trehalose dihydrate; and
0.01% polysorbate 20; at pH 7.0.
IV. 30.2 mg/mL eculizumab;
10 mM histidine HCl;
10% alpha-trehalose dehydrate; and
0.01% polysorbate 20; at pH 7.0.
V. 10 mg/mL eculizumab;
10 mM sodium phosphate;
150 mM sodium chloride; and
0.02% polysorbate 80; at pH 7.0.

Solutions I-V were prepared by way of concentration and formulation as described above in Example 1, or with only routine and minor modifications to the procedures. Briefly, to prepare solutions I and II, a 10 mg/mL solution of eculizumab in a phosphate-based buffer was concentrated to 30 mg/mL using a TFF. Next, the 30 mg/mL concentrate was subjected to six rounds of diafiltration (as described above in Example 1) into the HSSM formulation (20 mM histidine, 50 mM serine, 3% sorbitol, and 1.5% mannitol, at pH 7.0) to thereby produce solution II. A portion of solution II was further concentrated as described in Example 1 to 100 mg/mL, to produce solution I (the retentate).

Solution IV was prepared by diafiltration of the 30 mg/mL, phosphate-based eculizumab solution in the HTT buffer (10 mM histidine HCl; 10% alpha-trehalose dihydrate and 0.01% polysorbate 20, at pH 7.0), followed by the addition of Tween 20 to 0.01%. To prepare solution III, the 30 mg/mL, phosphate-based eculizumab solution was dia- filtered in HTT buffer and then further concentrated using the TFF as described in Example 1. Tween 20 was added to the retentate to a concentration of 0.01%. A flow chart depicting the steps for formulation of the five solutions is shown in FIG. 1. Each of the solutions was passed through a 0.22 µM filter.

Example 3

Stability of an Anti-C5 Antibody Formulated at High Concentration

A series of experiments was performed to evaluate the structural and functional stability of eculizumab formulated at high concentrations in aqueous solution (as prepared in Example 2). Sample aliquots of 2 mL were stored at −20° C., 2-8° C., and 37° C., and then evaluated at specified time intervals (e.g., one month, two months, three months, six months, nine months, 12 months, 18 months, and 24 months). The solutions were subjected to a number of chemical evaluations: appearance (visual inspection), osmolality, concentration (using a UV spectrophotometer), purity (by size exclusion chromatography-HPLC), isoelectric focusing (IEF), and sodium dodecyl sulfate polyacrylamide gel electrophoresis (SDS-PAGE). The functional stability of the antibody in each solution was tested using a human C5-binding assay. The results of each of the evaluations are provided below in the following tables (Roman numerals I to V in the tables correspond to the five named solutions above).

Methods and Results

A. Appearance (Visual Color, Clarity, Particles)

The appearance of each solution (under the varied storage conditions) was evaluated visually by observation of the vial against both a white and a black background. The test was performed at the intervals recited in the following tables for samples maintained at 2-8° C., −20° C., and 37° C. All solutions stored at 2-8° C. were found to be clear, colorless, and particulate free even after 24 months of storage.

All solutions stored at −20° C. were found to be clear, colorless, and particulate free at one month of storage. Solution V was not tested beyond 1 month, but solutions I to IV were clear, colorless, and particulate free for up to 6 months of storage. At 12 months, solution II contained small white particles. At 24 months solution I also contained small white particles. Solutions III and IV remained clear, colorless, and particulate free for at least 24 months.

All solutions stored at 37° C. were found to be clear, colorless, and particulate free for at least 1 month. After two months of storage at 37° C., solutions I and III appeared pale yellow in color. After three months of storage at 37° C., solutions I, II, III, and IV all appeared pale yellow in color and remained unchanged through six months.

B. Osmolality

The osmolality of each solution was measured using freezing point depression. The test was performed at the time intervals recited in the tables below for samples stored at 2-8° C., −20° C., and 37° C. Samples were tested in triplicate and the value reported herein is the mean of the three results.

All solutions stored at 2-8° C. had initial (To) osmolalities ranging from 299 to 365 mOsm/kg. After 24 months of storage at 2-8° C., the osmolality for each solution showed slight fluctuations, which were within the error of the method. The measured osmolalities for solutions I, II, and IV stored at 2-8° C. remained within ±15% of the initial measured osmolality, which is typically the osmolality specification for solutions in the earliest stage of development.

All solutions stored at −20° C. had initially-measured osmolalities ranging from 299 to 365 mOsm/kg. The osmolality for each solution stored up to 24 months at −20° C. showed slight fluctuations, which are within the error of the method. The osmolalities for all solutions remained within ±15% of the initially-measured osmolalities.

All solutions stored at 37° C. had initial ($T_0$) osmolalities ranging from 299 to 365 mOsm/kg. The osmolality of solutions I, II, and IV showed slight fluctuations during the first six months measurement, all of which were within the error of the method. The osmolalities for all solutions remained within ±15% of the initial osmolality. Solution III, however, had a measured osmolality of 863 mOsm/kg at 6 months, well above ±15% of the initial osmolality. While the disclosure is not bound by any particular theory or mechanism of action, it is believed that the solution by six months storage at 37° C. had undergone significant degradation, which resulted in an aberrant measurement at this time point.

C. Protein Concentration

Absorbance at 280 nm was used to determine the protein concentration in each test sample using an extinction coefficient of 1.46. The test sample was diluted to give an absorbance reading in the linear range of the assay (0.2 to 1.0 absorbance units). The absorbance of triplicate samples was measured by one operator, and then repeated independently by a second operator. The value reported is determined from the absorbance mean of the six measurements and the applied extinction coefficient.

D. Purity by HPLC Gel Permeation

The relative percents of monomeric IgG, aggregate, and fragments of the anti-C5 antibody were determined using SEC-HPLC (also referred to as gel permeation (GP)-HPLC). Test samples were injected onto a TSKgel G3000 SWXL column (Sigma-Aldrich) equilibrated with phosphate buffered saline (PBS), pH 7.0. The isocratic elution of the proteins is accomplished with a 20 minute run using the PBS, pH 7.0, at a flow rate of 1.0 mL/minute. Protein peaks were monitored by spectrophotometry at a wavelength of 214 nm and the percent purity of the monomeric IgG is expressed as a percentage of the total integrated peak area. Detection of the larger mass multimers was by observation of peaks eluting prior to the monomer peak. A measurement was made at each of the intervals recited in the following tables for samples stored at 2-8° C., −20° C., and 37° C.

All solutions stored at 2-8° C. had an initially-measured (To) purity of 99.1% monomer or greater. The purity for most of the solutions at up to six months of storage at 2-8° C. showed slight fluctuations equal to the variability of the method throughout the study. The purity for all solutions remained equal to or greater than 98.0% for up to 24 months of storage. The stability profile of solution II (in the so-called "HSSM" formulation) most closely resembled the profile of the control (Solution IV—10 mg/mL in 10 mM sodium phosphate, 150 mM sodium chloride, 0.02% polysorbate 80, pH 7.0).

All solutions stored at −20° C. had a purity of 99.1% monomer or greater at T=0. From T=0 through T=24 months, the purity for most of the solutions showed slight fluctuations equal to the variability of the method throughout the study. The purity of Solutions 1 and 2 remained virtually unchanged through T=24 months. The purity of Solution 3 remained above 98.7% through 12 months, and then dropped to 97.3% at 24 months. Solution 4 had a purity of 98.5% through 24 months. Solutions 1, 2, and 4 all remained at above 98.0% through 24 months. Solution 3 remained above 95.0% through 24 months.

All solutions stored at 37° C. had a purity of 99.1% monomer or greater at T=0. Beginning at the 1 month time point, significant increases in aggregate and fragments were seen in all solutions. The purity of solutions I, II, and III remained above 90.5% through six months. Solution IV had a purity of ≥97.4% through six months.

Solutions II and IV contained detectable amounts of fragment at $T_0$ (0.3 and 0.7%, respectively) which then increased in all storage conditions during the study.

E. SDS-PAGE (Non-Reduced Coomassie)

Samples of the stored solutions were denatured by heating in the presence of sodium dodecyl sulfate (SDS). The polypeptides present in the samples were separated according to molecular size by electrophoresis through a gradient 4% to 20% w/v pre-cast Tris-glycine SDS-polyacrylamide gel. The proteins within the gel were visualized by staining the gel with Coomassie Blue.

Polypeptide bands within the gels were quantified using laser densitometry. The limit of quantitation of the staining procedure was approximately 0.08 μg/polypeptide band. That is, when an 8 μg test sample was applied, the limit of quantitation of a single discrete impurity is equivalent to approximately 1.0% of the total protein. The reproducibility of the method expressed as a coefficient of variation is approximately 1.8%. The test was performed at the intervals in the following tables (below) for samples stored at 2-8° C., −20° C., and 37° C.

All solutions stored at 2-8° C. had an initially-measured (To) relative percentage of at least 90% IgG. The percent IgG for all solutions stored at 2-8° C. was ≥90% at 24 months. All solutions stored at −20° C. also had an initially-measured relative percentage of 90% IgG. The percent IgG for solutions I and IV was ≥90% at 24 months. Solutions II and III had percentage of IgG of 89% and 88%, respectively, at 24 months. As the percentage of IgG at $T_0$ was 90%, 88% and 89% were within the error of the method and did not necessarily represent a significant change in quality.

All solutions stored at 37° C. had a relative percent IgG of 90% at $T_0$. The percentage of IgG for solution IV remained ≥90% through 3 months of storage. Solution I contained 88% IgG at 3 months, which was within the error of the method, and did not necessarily represent a significant change in quality. At 6 months of storage at 37° C., all solutions were ≤73% IgG, indicating significant degradation of the antibody.

F. SDS-PAGE (Reduced Coomassie)

Samples were prepared and analyzed as described under Section E "SDS-PAGE (Non-reduced Coomassie)"; however, the samples were further denatured in the presence of 50 mM dithiothreitol (DTT) to disrupt disulfide bonds within the antibody structure. The test was performed at the intervals in the following tables (below) for samples stored at 2-8° C., −20° C., and 37° C.

All solutions stored at 2-8° C. had a relative percent of IgG as heavy and light chain of 100% at $T_0$. The percent of IgG as heavy and light chain for all of the solutions stored at 2-8° C. remained at 100% throughout the study. All solutions stored at −20° C. also had a relative percent of IgG as heavy and light chain of 100% throughout the study.

All solutions stored at 37° C. had a relative percent of IgG as heavy and light chain of 100% at $T_0$. At 1 month, the relative percentage of IgG as heavy and light chain remained at 100% for solutions III and IV. The percentage of IgG as heavy and light chains for solution I fell to 99% and for Solution II fell to 98% after one month of storage at 37° C.

After two months of storage at 37° C., all solutions were ≤98.0% IgG as heavy and light chains. The percentage of IgG as heavy and light chains continued to fall through six months of storage at 37° C. for each solution, indicating significant degradation of the antibody.

G. Isoelectric Focusing

The isoelectric focusing studies used a flat bed electrophoresis system. Pre-cast agarose gels covering a pH range of 3.0 to 10.0 were employed. Samples of the stored samples were loaded onto the gel at a predetermined optimized load position along with commercially available pI marker standards. Following focusing for a set number of volt-hours, separated charge variants were visualized by staining with a Coomassie Blue staining solution. The banding pattern of samples on the stained gel was analyzed using laser densitometry. The pI of the separated isoforms and the relative mass of each isoform (as a percentage of total mass) was also determined. pIs are calculated by interpolation from a standard curve established by the pI marker standards. The relative mass of each isoform as a percent of total mass is calculated from its response relative to the total response of the sample load. The measurements were performed at the intervals in the following tables (below) for samples stored at 2-8° C., −20° C., and 37° C.

All solutions stored at 2-8° C. had banding patterns comparable to a reference antibody standard and pI ranges of approximately 5.66 to 6.35 at $T_0$. Minor variations in pI were seen throughout the study, which are within the variability of the method. After up to 12 months of storage, banding patterns of the antibody present in the samples were comparable to the reference antibody standard and the pI of all bands remained between 5.48 and 6.60 for all of the solutions. Solutions I and II had banding patterns which remained comparable to the reference antibody material and the pI of all bands between 5.48 and 6.60 through 24 months of storage at 2-8° C. Solutions III and IV did exhibit a change in the banding pattern beginning at the 18 month time point. That is, the most basic band was not detected.

All solutions stored at −20° C. had banding patterns comparable to the reference antibody material and pI ranges of ~5.66 to 6.35 at $T_0$. Minor variations in pI were seen throughout the study, which are within the variability of the method. Throughout 24 months of storage at −20° C., banding patterns were comparable to the reference antibody material and the pI of all bands was between 5.61 and 6.44 for all of the solutions.

All solutions stored at 37° C. had banding patterns comparable to the reference antibody and pI ranges of ~5.66 to 6.35 at T=0. After up to 1 month of storage, banding patterns were comparable to reference material and the pI of all bands was between 5.45 and 6.43 for all of the solutions. After two months of storage, smearing between the bands appeared, an additional acidic band appeared, and the intensities of the bands diminished. No significant difference was seen between the four solutions tested at this temperature condition. The appearance of smearing, development of more acidic bands, and changes in intensity of the main band continued for the duration of the 24 month study.

H. Potency by C5 Binding Assay

The C5 binding assay used to test the functional characteristics of the stored solutions was a quantitative immunoassay. A standard curve was prepared from a reference anti-C5 antibody standard to include concentrations at 500, 250, 125, 62.5 and 31.3 binding units (BU)/mL. A four-parameter fit was applied to the standard curve and test sample results were interpolated from the curve. Each sample was diluted and tested in triplicate at each of three dilutions predetermined to fall within the linear range of the assay. Results were averaged and observed test results in units of BU/mL were divided by the product concentration in mg/mL to obtain results in BU/mg. The measurements were performed at the intervals in the following tables (below) for samples stored at 2-8° C., −20° C., and 37° C.

All solutions stored at 2-8° C. exhibited binding activity ranging from 946,875 to 1,063,353 BU/mg at $T_0$. Throughout the 24 month study, the purity for all of the tested solutions remained between 855,801 and 1,194,123 BU/mg. At 12 months, solution I contained 1,306,497 BU/mg, but at 18 and 24 months solution I contained 1,013,876 and 920,747 BU/mg, respectively. All solutions stored at −20° C. contained 946,875 to 1,063,353 BU/mg at $T_0$. Throughout the 24 month study, the activity present in all solutions stored at −20° C. remained between 778,672 and 1,148,100 BU/mg.

All solutions stored at 37° C. exhibited initially-measured binding activity ranging from 946,875 to 1,063,353 BU/mg. After six months of storage at 37° C., solutions I and IV exhibiting activity of between 827,206 and 1,202,435 BU/mg. Solutions II and III exhibited binding activity between 1,019,401 and 1,243,601 BU/mg after 3 months, whereas, at six months, the activity of the antibody maintained at 37° C. in solution II and III was 1,679,080 and 1,976,400 BU/mg respectively. Again, while the disclosure is not bound by any particular theory or mechanism of action, it is believed that the solution by six months storage at 37° C. had undergone significant degradation, which resulted in an aberrant measurement at this time point.

TABLE 3

Appearance and Osmolality of Eculizumab Solutions at 2 to 8° C. for 24 Months

| Analytical method | Time Point (months) | 2-8° C. | | | | |
| --- | --- | --- | --- | --- | --- | --- |
| | | I | II | III | IV | V |
| Appearance | 0 | Clear and colorless, Particulate free | Clear and colorless, Particulate free | Clear and colorless, Particulate free | Clear and colorless, Particulate free | Clear and colorless, Particulate free |
| | 1 | Clear and colorless, Particulate free | Clear and colorless, Particulate free | Clear and colorless, Particulate free | Clear and colorless, Particulate free | Clear and colorless, Particulate free |
| | 2 | Clear and colorless, Particulate free | Clear and colorless, Particulate free | Clear and colorless, Particulate free | Clear and colorless, Particulate free | Clear and colorless, Particulate free |

TABLE 3-continued

Appearance and Osmolality of Eculizumab Solutions at 2 to 8° C. for 24 Months

| Analytical method | Time Point (months) | 2-8° C. | | | | |
|---|---|---|---|---|---|---|
| | | I | II | III | IV | V |
| | 3 | Clear and colorless, Particulate free | Clear and colorless, Particulate free | Clear and colorless, Particulate free | Clear and colorless, Particulate free | Clear and colorless, Particulate free |
| | 6 | Clear and colorless, Particulate free | Clear and colorless, Particulate free | Clear and colorless, Particulate free | Clear and colorless, Particulate free | Clear and colorless, Particulate free |
| | 9 | Clear and colorless, Particulate free | Clear and colorless, Particulate free | Clear and colorless, Particulate free | Clear and colorless, Particulate free | Clear and colorless, Particulate free |
| | 12 | Clear and colorless, Particulate free | Clear and colorless, Particulate free | Clear and colorless, Particulate free | Clear and colorless, Particulate free | Clear and colorless, Particulate free |
| | 18 | Clear and colorless, Particulate free | Clear and colorless, Particulate free | Clear and colorless, Particulate free | Clear and colorless, Particulate free | Clear and colorless, Particulate free |
| | 24 | Clear and colorless, Particulate free | Clear and colorless, Particulate free | Clear and colorless, Particulate free | Clear and colorless, Particulate free | Clear and colorless, Particulate free |
| Osmolality | 0 | 365 mOsm/kg | 333 mOsm/kg | 356 mOsm/kg | 313 mOsm/kg | 299 mOsm/kg |
| | 1 | | | | | |
| | 2 | | | | | |
| | 3 | | | | | |
| | 6 | 367 mOsm/kg | 336 mOsm/kg | 364 mOsm/kg | 326 mOsm/kg | 300 mOsm/kg |
| | 9 | | | | | |
| | 12 | 371 mOsm/kg | 335 mOsm/kg | 366 mOsm/kg | 310 mOsm/kg | 305 mOsm/kg |
| | 18 | 366 mOsm/kg | 337 mOsm/kg | 358 mOsm/kg | 324 mOsm/kg | 303 mOsm/kg |
| | 24 | 372 mOsm/kg | 338 mOsm/kg | 382 mOsm/kg | 321 mOsm/kg | 306 mOsm/kg |

TABLE 4

Protein Concentration and SEC-HPLC Evaluation of Eculizumab Solutions Stored at 2 to 8° C. for 24 Months

| Analytical method | Time Point (months) | 2-8° C. | | | | |
|---|---|---|---|---|---|---|
| | | I | II | III | IV | V |
| Protein Concentration | 0 | 105.9 mg/mL | 29.3 mg/mL | 107.6 mg/mL | 31.1 mg/mL | 10.0 mg/mL |
| | 1 | 108.4 mg/mL | 29.9 mg/mL | 108.6 mg/mL | 31.2 mg/mL | 10.2 mg/mL |
| | 2 | 104.0 mg/mL | 29.1 mg/mL | 101.6 mg/mL | 30.0 mg/mL | 10.0 mg/mL |
| | 3 | 102.8 mg/mL | 29.0 mg/mL | 104.3 mg/mL | 30.2 mg/mL | 9.8 mg/mL |
| | 6 | 104.0 mg/mL | 29.1 mg/mL | 103.1 mg/mL | 30.4 mg/mL | 9.9 mg/mL |
| | 9 | 110.0 mg/mL | 30.8 mg/mL | 112.1 mg/mL | 31.6 mg/mL | 10.0 mg/mL |
| | 12 | 106.2 mg/mL | 30.2 mg/mL | 109.8 mg/mL | 31.3 mg/mL | 10.1 mg/mL |
| | 18 | 108.7 mg/mL | 30.6 mg/mL | 110.9 mg/mL | 31.2 mg/mL | 10.1 mg/mL |
| | 24 | 106.4 mg/mL | 30.7 mg/mL | 111.8 mg/mL | 32.5 mg/mL | 10.3 mg/mL |
| SEC-HPLC | 0 | 0.3% aggregates 99.7% monomer 0% fragments | 0.2% aggregates 99.8% monomer 0% fragments | 0.3% aggregates 99.5% monomer 0.3% fragments | 0.2% aggregates 99.1% monomer 0.7% fragments | 0.2% aggregates 99.8% monomer 0% fragments |
| | 1 | 0.4% aggregates 99.6% monomer 0% fragments | 0.3% aggregates 99.7% monomer 0% fragments | 0.4% aggregates 98.7% monomer 0.9% fragments | 0.4% aggregates 98.7% monomer 0.9% fragments | 0.3% aggregates 99.7% monomer 0% fragments |
| | 2 | 0.5% aggregates 99.5% | 0.4% aggregates 99.6% | 0.4% aggregates 98.6% | 0.3% aggregates 98.6% | 0.3% aggregates 99.7% |

TABLE 4-continued

Protein Concentration and SEC-HPLC Evaluation of Eculizumab Solutions Stored at 2 to 8° C. for 24 Months

| Analytical method | Time Point (months) | 2-8° C. | | | | |
|---|---|---|---|---|---|---|
| | | I | II | III | IV | V |
| | 3 | monomer 0% fragments 0.5% aggregates 99.5% | monomer 0% fragments 0.4% aggregates 99.6% | monomer 1.0% fragments 0.3% aggregates 98.7% | monomer 1.2% fragments 0.2% aggregates 98.5% | monomer 0% fragments 0.3% aggregates 99.7% |
| | 6 | monomer 0% fragments 0.6% aggregates 99.4% | monomer 0% fragments 0.4% aggregates 99.6% | monomer 1.0% fragments 0.4% aggregates 98.8% | monomer 1.3% fragments 0.3% aggregates 98.8% | monomer 0% fragments 0.3% aggregates 99.6% |
| | 9 | monomer 0% fragments 0.9% aggregates 99.2% | monomer 0% fragments 0.3% aggregates 99.7% | monomer 0.7% fragments 0.5% aggregates 99.3% | monomer 1.0% fragments 0.3% aggregates 99.4% | monomer 0.1% fragments 0.4% aggregates 99.7% |
| | 12 | monomer 0% fragments 1.3% aggregates 98.7% | monomer 0% fragments 0.7% aggregates 99.3% | monomer 0.2% fragments 0.5% aggregates 98.9% | monomer 0.3% fragments 0.4% aggregates 98.8% | monomer 0% fragments 0.6% aggregates 99.5% |
| | 18 | monomer 0% fragments 1.6% aggregates 98.4% | monomer 0% fragments 0.8% aggregates 99.2% | monomer 0.6% fragments 0.6% aggregates 99.2% | monomer 0.9% fragments 0.3% aggregates 99.3% | monomer 0% fragments 0.5% aggregates 99.5% |
| | 24 | monomer 0% fragments 2.0% aggregates 98.0% monomer 0% fragments | monomer 0% fragments 0.9% aggregates 99.1% monomer 0% fragments | monomer 0.2% fragments 0.7% aggregates 99.1% monomer 0.2% fragments | monomer 0.3% fragments 0.3% aggregates 99.4% monomer 0.3% fragments | monomer 0% fragments 0.6% aggregates 99.4% monomer 0% fragments |

TABLE 5

SDS-PAGE Analysis of Eculizumab Solutions Stored at 2 to 8° C. for 24 Months

| Analytical method | Time Point (months) | 2-8° C. | | | | |
|---|---|---|---|---|---|---|
| | | I | II | III | IV | V |
| SDS-PAGE Non-reduced | 0 | 90% IgG | 90% IgG | 90% IgG | 90% IgG | 90% IgG |
| | 1 | 92% IgG | 92% IgG | 92% IgG | 92% IgG | 92% IgG |
| | 2 | 91% IgG | 91% IgG | 92% IgG | 90% IgG | 93% IgG |
| | 3 | 92% IgG | 92% IgG | 92% IgG | 92% IgG | 91% IgG |
| | 6 | 89% IgG | 89% IgG | 90% IgG | 90% IgG | 90% IgG |
| | 9 | 91% IgG | 91% IgG | 91% IgG | 91% IgG | 90% IgG |
| | 12 | 90% IgG | 90% IgG | 90% IgG | 90% IgG | 91% IgG |
| | 18 | 90% IgG | 90% IgG | 91% IgG | 90% IgG | 91% IgG |
| | 24 | 91% IgG | 90% IgG | 91% IgG | 90% IgG | 91% IgG |
| SDS-PAGE Reduced | 0 | 100% IgG as heavy and light chains | 100% IgG as heavy and light chains | 100% IgG as heavy and light chains | 100% IgG as heavy and light chains | 100% IgG as heavy and light chains |
| | 1 | 100% IgG as heavy and light chains | 100% IgG as heavy and light chains | 100% IgG as heavy and light chains | 100% IgG as heavy and light chains | 100% IgG as heavy and light chains |
| | 2 | 100% IgG as heavy and light chains | 100% IgG as heavy and light chains | 99% IgG as heavy and light chains | 99% IgG as heavy and light chains | 100% IgG as heavy and light chains |

TABLE 5-continued

SDS-PAGE Analysis of Eculizumab Solutions Stored at 2 to 8° C. for 24 Months

| Analytical method | Time Point (months) | 2-8° C. I | II | III | IV | V |
|---|---|---|---|---|---|---|
| | 3 | 100% IgG as heavy and light chains | 100% IgG as heavy and light chains | 100% IgG as heavy and light chains | 100% IgG as heavy and light chains | 100% IgG as heavy and light chains |
| | 6 | 100% IgG as heavy and light chains | 100% IgG as heavy and light chains | 100% IgG as heavy and light chains | 100% IgG as heavy and light chains | 100% IgG as heavy and light chains |
| | 9 | 100% IgG as heavy and light chains | 100% IgG as heavy and light chains | 100% IgG as heavy and light chains | 100% IgG as heavy and light chains | 100% IgG as heavy and light chains |
| | 12 | 100% IgG as heavy and light chains | 100% IgG as heavy and light chains | 100% IgG as heavy and light chains | 100% IgG as heavy and light chains | 100% IgG as heavy and light chains |
| | 18 | 100% IgG as heavy and light chains | 100% IgG as heavy and light chains | 100% IgG as heavy and light chains | 100% IgG as heavy and light chains | 100% IgG as heavy and light chains |
| | 24 | 100% IgG as heavy and light chains | 100% IgG as heavy and light chains | 100% IgG as heavy and light chains | 100% IgG as heavy and light chains | 100% IgG as heavy and light chains |

TABLE 6

IEF and C5-binding Analysis of Eculizumab Solutions Stored at 2 to 8° C. for 24 Months

| Analytical method | Time Point (months) | 2-8° C. I | II | III | IV | V |
|---|---|---|---|---|---|---|
| IEF | 0 | 3 major bands All major and minor bands resolved between pI 5.68 and 6.35 | 3 major bands All major and minor bands resolved between pI 5.67 and 6.35 | 3 major bands All major and minor bands resolved between pI 5.67 and 6.35 | 3 major bands All major and minor bands resolved between pI 5.66 and 6.35 | 3 major bands All major and minor bands resolved between pI 5.72 and 6.35 |
| | 1 | 3 major bands All major and minor bands resolved between pI 5.68 and 6.44 | 3 major bands All major and minor bands resolved between pI 5.69 and 6.57 | 3 major bands All major and minor bands resolved between pI 5.68 and 6.54 | 3 major bands All major and minor bands resolved between pI 5.69 and 6.54 | 3 major bands All major and minor bands resolved between pI 5.67 and 6.40 |
| | 2 | 3 major bands All major and minor bands resolved between pI 5.50 and 6.42 | 3 major bands All major and minor bands resolved between pI 5.48 and 6.40 | 3 major bands All major and minor bands resolved between pI 5.51 and 6.43 | 3 major bands All major and minor bands resolved between pI 5.53 and 6.46 | 3 major bands All major and minor bands resolved between pI 5.54 and 6.48 |
| | 3 | 3 major bands All major and minor bands resolved between pI 5.69 and 6.42 | 3 major bands All major and minor bands resolved between pI 5.68 and 6.41 | 3 major bands All major and minor bands resolved between pI 5.68 and 6.41 | 3 major bands All major and minor bands resolved between pI 5.69 and 6.41 | 3 major bands All major and minor bands resolved between pI 5.69 and 6.41 |
| | 6 | 3 major bands All major and minor bands resolved between pI 5.79 and 6.40 | 3 major bands All major and minor bands resolved between pI 5.79 and 6.39 | 3 major bands All major and minor bands resolved between pI 5.78 and 6.40 | 3 major bands All major and minor bands resolved between pI 5.81 and 6.42 | 3 major bands All major and minor bands resolved between pI 5.82 and 6.44 |
| | 9 | 3 major bands All major and minor bands resolved between pI 5.83 and 6.40 | 3 major bands All major and minor bands resolved between pI 5.83 and 6.41 | 3 major bands All major and minor bands resolved between pI 5.85 and 6.42 | 3 major bands All major and minor bands resolved between pI 5.77 and 6.35 | 3 major bands All major and minor bands resolved between pI 5.80 and 6.36 |
| | 12 | 3 major bands All major and minor bands resolved between pI 5.83 and 6.47 | 3 major bands All major and minor bands resolved between pI 5.84 and 6.51 | 3 major bands All major and minor bands resolved between pI 5.87 and 6.60 | 3 major bands All major and minor bands resolved between pI 5.87 and 6.54 | 3 major bands All major and minor bands resolved between pI 5.85 and 6.52 |

TABLE 6-continued

IEF and C5-binding Analysis of Eculizumab Solutions Stored at 2 to 8° C. for 24 Months

| Analytical method | Time Point (months) | 2-8° C. I | II | III | IV | V |
|---|---|---|---|---|---|---|
| | 18 | 3 major bands All major and minor bands resolved between pI 5.60 and 6.31 | 3 major bands All major and minor bands resolved between pI 5.58 and 6.30 | 2 major bands All major and minor bands resolved between pI 5.58 and 6.30 (Does not compare to Reference). | 2 major bands All major and minor bands resolved between pI 5.60 and 6.33 (Does not compare to Reference). | 3 major bands All major and minor bands resolved between pI 5.61 and 6.34 |
| | 24 | 3 major bands All major and minor bands resolved between pI 5.64 to 6.29 | 3 major bands All major and minor bands resolved between pI 5.63 to 6.26 | 2 major bands All Major and minor bands between pI 5.60 to 6.24 Does not compare to Reference. | 2 major bands All Major and minor bands between pI 5.75 to 6.25 Does not compare to Reference. | 3 major bands All Major and minor bands between pI 5.62 to 6.26 |
| C5 Binding | 0 | 1,026,912 BU/mg | 1,063,353 BU/mg | 1,019,401 BU/mg | 967,645 BU/mg | 946,875 BU/mg |
| | 1 | 1,067,612 BU/mg | 1,025,293 BU/mg | 981,238 BU/mg | 1,078,726 BU/mg | 960,989 BU/mg |
| | 2 | 1,038,662 BU/mg | 1,172,680 BU/mg | 1,103,182 BU/mg | 1,052,083 BU/mg | 1,097,917 BU/mg |
| | 3 | 1,031,534 BU/mg | 1,127,155 BU/mg | 1,074,624 BU/mg | 968,543 BU/mg | 1,140,519 BU/mg |
| | 6 | 879,407 BU/mg | 856,959 BU/mg | 1,121,484 BU/mg | 860,403 BU/mg | 894,360 BU/mg |
| | 9 | 1,009,470 BU/mg | 1,015,625 BU/mg | 965,470 BU/mg | 973,674 BU/mg | 1,026,042 BU/mg |
| | 12 | 1,306,497 BU/mg | 1,194,123 BU/mg | 1,107,127 BU/mg | 1,097,244 BU/mg | 1,127,269 BU/mg |
| | 18 | 1,013,876 BU/mg | 855,801 BU/mg | 958,070 BU/mg | 948,518 BU/mg | 898,309 BU/mg |
| | 24 | 920,747 BU/mg | 958,880 BU/mg | 1,036,747 BU/mg | 848,043 BU/mg | 914,522 BU/mg |

"BU" refers to binding units.

TABLE 7

Appearance, Osmolality, and Protein Concentration of Eculizumab Solutions Stored at 37° C. for Up to 24 Months

| Analytical method | Time Point (months) | 37° C. I | II | III | IV | V |
|---|---|---|---|---|---|---|
| Appearance | 0 | Clear and colorless, Particulate free | Clear and colorless, Particulate free | Clear and colorless, Particulate free | Clear and colorless, Particulate free | Clear and colorless, Particulate free |
| | 1 | Clear and colorless, Particulate free | Clear and colorless, Particulate free | Clear and colorless, Particulate free | Clear and colorless, Particulate free | n/a |
| | 2 | Clear, pale yellow, Particulate free | Clear and colorless, Particulate free | Clear, pale yellow, Particulate free | Clear and colorless, Particulate free | n/a |
| | 3 | Clear, pale yellow, Particulate free | Clear, pale yellow, Particulate free | Clear, pale yellow, Particulate free | Clear, pale yellow, Particulate free | n/a |
| | 6 | Clear, pale yellow, Particulate free | Clear, pale yellow, Particulate free | Clear, pale yellow, Particulate free | Clear, pale yellow, Particulate free | n/a |
| Osmolality | 0 | 365 mOsm/kg | 333 mOsm/kg | 356 mOsm/kg | 313 mOsm/kg | n/a |
| | 1 | | | | | |
| | 2 | | | | | |
| | 3 | | | | | |
| | 6 | 394 mOsm/kg | 349 mOsm/kg | 863 mOsm/kg | 332 mOsm/kg | 300 mOsm/kg |
| Protein Concentration | 0 | 105.9 mg/mL | 29.3 mg/mL | 107.6 mg/mL | 31.1 mg/mL | 10.0 mg/mL |
| | 1 | 99.0 mg/mL | 30.1 mg/mL | 111.7 mg/mL | 31.8 mg/mL | n/a |
| | 2 | 115.1 mg/mL | 29.8 mg/mL | 114.3 mg/mL | 31.7 mg/mL | n/a |
| | 3 | 106.2 mg/mL | 30.1 mg/mL | 113.7 mg/mL | 31.5 mg/mL | n/a |
| | 6 | 109.5 mg/mL | 38.6 mg/mL | 139.3 mg/mL | 35.7 mg/mL | n/a |

TABLE 8

SEC-HPLC and SDS-PAGE Analysis of Eculizumab Solutions Stored at 37° C. for Up to 24 Months

| Analytical method | Time Point (months) | 37° C. I | II | III | IV | V |
|---|---|---|---|---|---|---|
| SEC-HPLC | 0 | 0.3% aggregates 99.7% monomer 0% fragments | 0.2% aggregates 99.8% monomer 0% fragments | 0.3% aggregates 99.5% monomer 0.3% fragments | 0.2% aggregates 99.1% monomer 0.7% fragments | 0.2% aggregates 99.8% monomer 0% fragments |
| | 1 | 2.3% aggregates 97.6% monomer 0.1% fragments | 1.4% aggregates 98.5% monomer 0.1% fragments | 1.4% aggregates 97.9% monomer 0.7% fragments | 0.7% aggregates 98.3% monomer 1.0% fragments | n/a |
| | 2 | 4.1% aggregates 95.7% monomer 0.2% fragments | 2.5% aggregates 97.3% monomer 0.2% fragments | 2.2% aggregates 97.1% monomer 0.7% fragments | 1.0% aggregates 98.0% monomer 1.0% fragments | n/a |
| | 3 | 5.4% aggregates 94.5% monomer 0.2% fragments | 3.2% aggregates 96.5% monomer 0.3% fragments | 5.6% aggregates 96.1% monomer 1.4% fragments | 1.1% aggregates 97.9% monomer 1.0% fragments | n/a |
| | 6 | 9.1% aggregates 90.5% monomer 0.4% fragments | 6.0% aggregates 93.4% monomer 0.5% fragments | 3.8% aggregates 94.9% monomer 1.3% fragments | 1.8% aggregates 97.4% monomer 0.8% fragments | n/a |
| SDS-PAGE Non-reduced | 0 | 90% IgG | 90% IgG | 90% IgG | 90% IgG | n/a |
| | 1 | 92% IgG | 91% IgG | 92% IgG | 92% IgG | n/a |
| | 2 | 91% IgG | 92% IgG | 91% IgG | 92% IgG | n/a |
| | 3 | 88% IgG | 79% IgG | 84% IgG | 91% IgG | n/a |
| | 6 | 62% IgG | 60% IgG | 70% IgG | 73% IgG | n/a |
| SDS-PAGE Reduced | 0 | 100% IgG as heavy and light chains | 100% IgG as heavy and light chains | 100% IgG as heavy and light chains | 100% IgG as heavy and light chains | 100% IgG as heavy and light chains |
| | 1 | 99% IgG as heavy and light chains | 98% IgG as heavy and light chains | 100% IgG as heavy and light chains | 100% IgG as heavy and light chains | n/a |
| | 2 | 96% IgG as heavy and light chains | 96% IgG as heavy and light chains | 98% IgG as heavy and light chains | 97% IgG as heavy and light chains | n/a |
| | 3 | 95% IgG as heavy and light chains | 94% IgG as heavy and light chains | 97% IgG as heavy and light chains | 97% IgG as heavy and light chains | n/a |
| | 6 | 88% IgG as heavy and light chains | 85% IgG as heavy and light chains | 93% IgG as heavy and light chains | 91% IgG as heavy and light chains | n/a |

TABLE 9

IEF and C5-Binding Analysis of Eculizumab Solutions Stored at 37° C. for Up to 24 Months

| Analytical method | Time Point (months) | 37° C. I | II | III | IV | V |
|---|---|---|---|---|---|---|
| IEF | 0 | 3 major bands All major and minor bands resolved between pI 5.68 and 6.35 | 3 major bands All major and minor bands resolved between pI 5.67 and 6.35 | 3 major bands All major and minor bands resolved between pI 5.67 and 6.35 | 3 major bands All major and minor bands resolved between pI 5.66 and 6.35 | 3 major bands All major and minor bands resolved between pI 5.72 and 6.35 |
| | 1 | 3 major bands All major and minor bands | 3 major bands All major and minor bands | 3 major bands All major and minor bands | 3 major bands All major and minor bands | n/a |

TABLE 9-continued

IEF and C5-Binding Analysis of Eculizumab Solutions Stored at 37° C. for Up to 24 Months

| Analytical method | Time Point (months) | 37° C. | | | | |
|---|---|---|---|---|---|---|
| | | I | II | III | IV | V |
| | 2 | resolved between pI 5.58 and 6.42 3 major bands All major and minor bands resolved between pI 5.21 and 6.33 | resolved between pI 5.56 and 6.43 3 major bands All major and minor bands resolved between pI 5.17 and 6.32 | resolved between pI 5.55 and 6.43 3 major bands All major and minor bands resolved between pI 5.18 and 6.31 | resolved between pI 5.56 and 6.41 3 major bands All major and minor bands resolved between pI 5.19 and 6.31 | n/a |
| | 3 | 3 major bands All major and minor bands resolved between pI 5.49 and 6.39 | 3 major bands All major and minor bands resolved between pI 5.49 and 6.39 | 3 major bands All major and minor bands resolved between pI 5.50 and 6.43 | 3 major bands All major and minor bands resolved between pI 5.49 and 6.42 | n/a |
| | 6 | 6 major bands 2 minor bands All major and minor bands resolved between pI 5.62 and 6.44 | 6 major bands 1 minor bands All major and minor bands resolved between pI 5.61 and 6.28 | 5 major bands 2 minor bands All major and minor bands resolved between pI 5.70 and 6.40 | 5 major bands 3 minor bands All major and minor bands resolved between pI 5.62 and 6.41 | n/a |
| C5 Binding | 0 | 1,026,912 BU/mg | 1,063,353 BU/mg | 1,019,401 BU/mg | 967,645 BU/mg | 946,875 BU/mg |
| | 1 | 1,153,199 BU/mg | 1,122,301 BU/mg | 1,076,171 BU/mg | 950,275 BU/mg | n/a |
| | 2 | 1,157,508 BU/mg | 1,243,601 BU/mg | 1,056,248 BU/mg | 1,042,981 BU/mg | n/a |
| | 3 | 1,126,020 BU/mg | 1,167,982 BU/mg | 1085,642 BU/mg | 1,013,889 BU/mg | n/a |
| | 6 | 1,202,435 BU/mg | 1,679,080 BU/mg | 1,976,400 BU/mg | 827,206 BU/mg | n/a |

TABLE 10

Appearance, Osmolality, and Protein Concentration Determinations for Eculizumab Solutions Stored at −20° C. for Up to 24 Months

| Analytical method | Time Point (months) | −20° C. | | | | |
|---|---|---|---|---|---|---|
| | | I | II | III | IV | V |
| Appearance | 0 | Clear and colorless, Particulate free | Clear and colorless, Particulate free | Clear and colorless, Particulate free | Clear and colorless, Particulate free | Clear and colorless, Particulate free |
| | 1 | Clear and colorless, Particulate free | Clear and colorless, Particulate free | Clear and colorless, Particulate free | Clear and colorless, Particulate free | n/a |
| | 6 | Clear and colorless, Particulate free | Clear and colorless, Particulate free | Clear and colorless, Particulate free | Clear and colorless, Particulate free | n/a |
| | 12 | Clear and colorless, Particulate free | Clear and colorless, Small, white particles observed | Clear and colorless, Particulate free | Clear and colorless, Particulate free | n/a |
| | 24 | Clear and colorless, Small, white particles observed | Clear and colorless, Small, white particles observed | Clear and colorless, Particulate free | Clear and colorless, Particulate free | n/a |
| Osmolality | 0 | 365 mOsm/kg | 333 mOsm/kg | 356 mOsm/kg | 313 mOsm/kg | 299 mOsm/kg |
| | 1 | | | | | |
| | 6 | 361 mOsm/kg | 336 mOsm/kg | 356 mOsm/kg | 316 mOsm/kg | n/a |
| | 12 | 366 mOsm/kg | 337 mOsm/kg | 362 mOsm/kg | 316 mOsm/kg | n/a |
| | 24 | 369 mOsm/kg | 339 mOsm/kg | 368 mOsm/kg | 316 mOsm/kg | n/a |
| Protein Concentration | 0 | 105.9 mg/mL | 29.3 mg/mL | 107.6 mg/mL | 31.1 mg/mL | 10.0 mg/mL |
| | 1 | 107.5 mg/mL | 29.3 mg/mL | 109.1 mg/mL | 31.2 mg/mL | n/a |
| | 6 | 104.3 mg/mL | 28.8 mg/mL | 104.9 mg/mL | 30.3 mg/mL | n/a |

TABLE 10-continued

Appearance, Osmolality, and Protein Concentration Determinations for Eculizumab Solutions Stored at −20° C. for Up to 24 Months

| Analytical method | Time Point (months) | −20° C. | | | | |
|---|---|---|---|---|---|---|
| | | I | II | III | IV | V |
| | 12 | 105.7 mg/mL | 30.2 mg/mL | 105.6 mg/mL | 31.2 mg/mL | n/a |
| | 24 | 107.3 mg/mL | 30.6 mg/mL | 110.1 mg/mL | 32.2 mg/mL | n/a |

TABLE 11

SEC-HPLC, SDS-PAGE, IEF and C5-binding Analyses for Eculizumab Solutions Stored at −20° C. for Up to 24 Months

| Analytical method | Time Point | −20° C. | | | | |
|---|---|---|---|---|---|---|
| | | I | II | III | IV | V |
| SEC-HPLC | 0 | 0.3% aggregates 99.7% monomer 0% fragments | 0.2% aggregates 99.8% monomer 0% fragments | 0.3% aggregates 99.5% monomer 0.3% fragments | 0.2% aggregates 99.1% monomer 0.7% fragments | 0.2% aggregates 99.8% monomer 0% fragments |
| | 1 | 0.4% aggregates 99.6% monomer 0% fragments | 0.3% aggregates 99.7% monomer 0% fragments | 0.4% aggregates 98.7% monomer 1.0% fragments | 0.3% aggregates 98.6% monomer 1.2% fragments | n/a |
| | 6 | 0.3% aggregates 99.7% monomer 0% fragments | 0.3% aggregates 99.7% monomer 0% fragments | 0.9% aggregates 99.3% monomer 0.1% fragments | 0.2% aggregates 98.7% monomer 1.1% fragments | n/a |
| | 12 | 0.4% aggregates 99.6% monomer 0% fragments | 0.3% aggregates 99.7% monomer 0% fragments | 0.4% aggregates 98.7% monomer 1.0% fragments | 0.3% aggregates 98.5% monomer 1.3% fragments | n/a |
| | 24 | 0.4% aggregates 99.6% monomer 0% fragments | 0.3% aggregates 99.7% monomer 0% fragments | 1.7% aggregates 97.3% monomer 1.0% fragments | 0.2% aggregates 98.6% monomer 1.1% fragments | n/a |
| SDS-PAGE Non-reduced | 0 | 90% IgG | 90% IgG | 90% IgG | 90% IgG | n/a |
| | 1 | 92% IgG | 91% IgG | 92% IgG | 92% IgG | n/a |
| | 6 | 90% IgG | 89% IgG | 89% IgG | 89% IgG | n/a |
| | 12 | 90% IgG | 90% IgG | 90% IgG | 90% IgG | n/a |
| | 24 | 90% IgG | 89% IgG | 88% IgG | 91% IgG | n/a |
| SDS-PAGE Reduced | 0 | 100% IgG as heavy and light chains | 100% IgG as heavy and light chains | 100% IgG as heavy and light chains | 100% IgG as heavy and light chains | n/a |
| | 1 | 100% IgG as heavy and light chains | 100% IgG as heavy and light chains | 100% IgG as heavy and light chains | 100% IgG as heavy and light chains | n/a |
| | 6 | 100% IgG as heavy and light chains | 100% IgG as heavy and light chains | 100% IgG as heavy and light chains | 100% IgG as heavy and light chains | n/a |
| | 12 | 100% IgG as heavy and light chains | 100% IgG as heavy and light chains | 100% IgG as heavy and light chains | 100% IgG as heavy and light chains | n/a |
| | 24 | 100% IgG as heavy and light chains | 100% IgG as heavy and light chains | 100% IgG as heavy and light chains | 100% IgG as heavy and light chains | n/a |
| IEF | 0 | 3 major bands All major and minor bands resolved between pI 5.68 and 6.35 | 3 major bands All major and minor bands resolved between pI 5.67 and 6.35 | 3 major bands All major and minor bands resolved between pI 5.67 and 6.35 | 3 major bands All major and minor bands resolved between pI 5.66 and 6.35 | 3 major bands All major and minor bands resolved between pI 5.72 and 6.35 |

TABLE 11-continued

SEC-HPLC, SDS-PAGE, IEF and C5-binding Analyses for Eculizumab
Solutions Stored at −20° C. for Up to 24 Months

| Analytical method | Time Point | −20° C. | | | | |
|---|---|---|---|---|---|---|
| | | I | II | III | IV | V |
| | 1 | 3 major bands All major and minor bands resolved between pI 5.67 and 6.41 | 3 major bands All major and minor bands resolved between pI 5.64 and 6.37 | 3 major bands All major and minor bands resolved between pI 5.61 and 6.36 | 3 major bands All major and minor bands resolved between pI 5.63 and 6.35 | n/a |
| | 6 | 3 major bands All major and minor bands resolved between pI 5.76 and 6.44 | 3 major bands All major and minor bands resolved between pI 5.75 and 6.42 | 3 major bands All major and minor bands resolved between pI 5.72 and 6.41 | 3 major bands All major and minor bands resolved between pI 5.73 and 6.42 | n/a |
| | 12 | 3 major bands All major and minor bands resolved between pI 5.83 and 6.38 | 3 major bands All major and minor bands resolved between pI 5.82 and 6.37 | 3 major bands All major and minor bands resolved between pI 5.83 and 6.38 | 3 major bands All major and minor bands resolved between pI 5.81 and 6.37 | n/a |
| | 24 | 3 major bands All major and minor bands resolved between pI 5.64 to 6.27 | 3 major bands All major and minor bands resolved between pI 5.62 to 6.26 | 3 major bands All major and minor bands resolved between pI 5.63 to 6.27 | 3 major bands All major and minor bands resolved between pI 5.63 to 6.26 | n/a |
| C5 Binding | 0 | 1,026,912 BU/mg | 1,063,353 BU/mg | 1,019,401 BU/mg | 967,645 BU/mg | 946,875 BU/mg |
| | 1 | 1,032,946 BU/mg | 1,071,886 BU/mg | 903,223 BU/mg | 806,290 BU/mg | n/a |
| | 6 | 1,067,633 BU/mg | 904,948 BU/mg | 912,575 BU/mg | 778,672 BU/mg | n/a |
| | 12 | 1,148,100 BU/mg | 1,081,333 BU/mg | 1,144,255 BU/mg | 1,068,710 BU/mg | n/a |
| | 24 | 894,507 BU/mg | 918,210 BU/mg | 954,360 BU/mg | 790,264 BU/mg | n/a |

Discussion

As set forth in Tables 3 to 6, the high concentration antibody formulations described herein were markedly stable over a two year period. Each of solutions I to IV remained clear, colorless, and particulate-free over the course of the study, which indicated that no visible precipitation occurred during a two-year storage period. There was also no significant change in osmolality or protein concentration of these solutions, even at 24 months.

Moreover, the antibody present in solutions I and III (105 mg/mL antibody) remained at least 98% monomeric. As shown in Table 5, the antibody present in solution III remained over 99% monomeric even at the 2 year testing. Each of the solutions maintained the anti-C5 antibody as over 99% monomer when stored at 2° C. to 8° C. for up to 9 months. The highly-concentrated solutions not only maintained a high percentage of monomeric antibody, but contained very few aggregates or degradation or fragmentation products. For example, solutions I and II contained no detectable fragmentation products as determined by SEC-HPLC, even at 24 months of storage at 2° C. to 8° C. Solutions III and IV contained less than 0.5% fragments at 24 months (0.2% antibody fragments in solution III at 24 months and 0.3% antibody fragments in solution IV at 24 months). None of the solutions contains more than 2% aggregates at 24 months, with solutions II, III, and IV containing less than 1% aggregates at 24 months. These results indicate that the formulations described herein are capable of substantially maintaining the structural integrity of the anti-C5 antibody dissolved therein for at least 24 months storage at 2° C. to 8° C.

The solutions were also evaluated for retention of functional activity by measuring C5-binding activity. As set forth in Table 6, each of the solutions tested retained approximately 90% or more of their C5-binding activity after 24 months of storage at 2° C. to 8° C. The antibody formulated in solution II retained 100% of its C5-binding ability at 24 months. Virtually no change in the binding activity of the antibody to C5 was detected in any of the formulations tested at one year. These results indicate that the formulations described herein maintain the functional as well as structural stability of the anti-C5 antibodies dissolved therein for at least 2 years at 2° C. to 8° C.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A kit for treating Paroxysmal Nocturnal Hemoglobinuria (PNH) in a human patient, the kit comprising:
   (a) a stable aqueous solution comprising an anti-C5 antibody at a concentration of about 100 mg/mL to about 200 mg/mL, about 20 mM histidine, about 50 mM serine, about 3% (w/v) sorbitol, about 1.5% (w/v) mannitol; and
   (b) instructions for use,
   wherein the anti-C5 antibody comprises CDR1, CDR2, and CDR3 domains of a heavy chain comprising the amino acid sequence set forth in SEQ ID NO:13 and CDR1, CDR2, and CDR3 domains of a light chain comprising the amino acid sequence set forth in SEQ ID NO:12.

2. A kit for treating atypical hemolytic uremic syndrome (aHUS) in a human patient, the kit comprising:
(a) a stable aqueous solution comprising an anti-C5 antibody at a concentration of about 100 mg/mL to about 200 mg/mL, about 20 mM histidine, about 50 mM serine, about 3% (w/v) sorbitol, about 1.5% (w/v) mannitol; and
(b) instructions for use,
wherein the anti-C5 antibody comprises CDR1, CDR2, and CDR3 domains of a heavy chain comprising the amino acid sequence set forth in SEQ ID NO:13 and CDR1, CDR2, and CDR3 domains of a light chain comprising the amino acid sequence set forth in SEQ ID NO:12.

3. The kit of claim 1 or 2, wherein the anti-C5 antibody comprises a heavy chain comprising the amino acid sequence set forth in SEQ ID NO:13 and a light chain comprising the amino acid sequence set forth in SEQ ID NO:12.

4. The kit of claim 1 or 2, wherein the anti-C5 antibody is eculizumab.

5. The kit of claim 1 or 2, wherein the pH of the solution is between 6.5 and 7.5.

6. The kit of claim 1 or 2, wherein the anti-C5 antibody is at a concentration of 100 mg/mL.

7. The kit of claim 1 or 2, wherein the anti-C5 antibody remains at least 97% monomeric during storage at 2° C. to 8° C. for at least six months as determined by SEC-HPLC.

8. The kit of claim 1 or 2, wherein the anti-C5 antibody remains at least 97% monomeric during storage at 2° C. to 8° C. for at least one year as determined by SEC-HPLC.

9. The kit of claim 1 or 2, wherein less than 2% of the anti-C5 antibody in the solution is aggregated as determined by SEC-HPLC.

10. The kit of claim 1 or 2, wherein less than 1% of the anti-C5 antibody in the solution is fragmented as determined by SEC-HPLC.

11. The kit of claim 1 or 2, wherein during storage at 2° C. to 8° C. for at least six months the anti-C5 antibody retains at least 90% of its C5-binding activity, as compared to a reference anti-C5 antibody corresponding to the anti-C5 antibody prior to storage.

12. The kit of claim 1 or 2, wherein during storage at 2° C. to 8° C. for at least six months the anti-C5 antibody retains at least 95% of its ability to inhibit hemolysis, as compared to a reference anti-C5 antibody corresponding to the anti-C5 antibody prior to storage.

13. A kit for treating PNH or aHUS in a human patient, the kit comprising:
(a) a stable aqueous solution comprising eculizumab, about 20 mM histidine, about 50 mM serine, about 3% (w/v) sorbitol, about 1.5% (w/v) mannitol; and instructions for use.

* * * * *

UNITED STATES PATENT AND TRADEMARK OFFICE
CERTIFICATE OF CORRECTION

PATENT NO. : 9,925,262 B2
APPLICATION NO. : 15/384788
DATED : March 27, 2018
INVENTOR(S) : Xiao-Hong Zhou et al.

It is certified that error appears in the above-identified patent and that said Letters Patent is hereby corrected as shown below:

On the Title Page

In item (57), in Column 2, in "Abstract", Line 9, after "need" insert -- of --.

On page 2, in Column 2, under "Other Publications", Line 62, delete "Brochial" and insert -- Bronchial --, therefor.

On page 2, in Column 2, under "Other Publications", Line 62, delete "Hyperactivity,"" and insert -- Hyperreactivity," --, therefor.

On page 2, in Column 2, under "Other Publications", Line 67, delete "antiobodies:" and insert -- antibodies: --, therefor.

In the Specification

In Column 2, Line 41, delete "Miller-" and insert -- Müller- --, therefor.

In Column 3, Line 29, delete "Nat" and insert -- Natl --, therefor.

In Column 12, Line 38, delete "intrabodics" and insert -- intrabodies --, therefor.

In Column 12, Line 63, delete "DRAWINGS" and insert -- DRAWING --, therefor.

In Column 15, Line 36, after "$10^{11}$" insert -- , --.

In Column 20, Line 62, delete "7.7, 7.7" and insert -- 7.7, 7.8 --, therefor.

In Column 22, Line 46, delete "Pharm Sci 5(2:" and insert -- PharmSci 5(2): --, therefor.

In Column 23, Line 8, delete "lauroamidopropyl-," and insert -- lauramidopropyl-, --, therefor.

Signed and Sealed this
Nineteenth Day of June, 2018

Andrei Iancu
*Director of the United States Patent and Trademark Office*

CERTIFICATE OF CORRECTION (continued)
U.S. Pat. No. 9,925,262 B2

In Column 23, Line 10, delete "lauroamidopropyl);" and insert -- lauramidopropyl); --, therefor.

In Column 25, Line 45, delete "delivery," and insert -- delivery --, therefor.

In Column 34, Line 48, after "Nos." insert -- : --.

In Column 34, Line 67, after "Nos." insert -- : --.

In Column 36, Line 49, delete "$\gamma$," and insert -- $\lambda$, --, therefor.

In Column 38, Line 5, delete "Nat" and insert -- Natl --, therefor.

In Column 38, Line 46, delete "Nat" and insert -- Natl --, therefor.

In Column 41, Line 23, delete "jµg/kg," and insert -- µg/kg, --, therefor.

In Column 44, Line 26, delete "6:" and insert -- 16: --, therefor.

In Column 46, Line 11, delete "7." and insert -- 7; --, therefor.

In Column 50, Line 48, delete "Nat" and insert -- Natl --, therefor.

In Column 50, Line 51, delete "584:" and insert -- 584; --, therefor.

In Column 50, Line 66, delete "autoantibodics" and insert -- autoantibodies --, therefor.

In Column 56, Line 57, delete "38%" and insert -- 98% --, therefor.

In Column 58, Line 62, delete "(To)" and insert -- ($T_0$) --, therefor.

In Column 59, Line 10, delete "(To)" and insert -- ($T_0$) --, therefor.

In Column 59, Line 49, delete "(To)" and insert -- ($T_0$) --, therefor.

In Column 59, Line 67, before "98.5%" insert -- $\geq$ --.

In Column 60, Line 9, delete "II" and insert -- III --, therefor.

In Column 78, Line 43, delete "II" and insert -- III --, therefor.

In the Claims

In Column 114, Line 28, in Claim 13, before "instructions" insert -- (b) --.